(12) United States Patent
Hyde et al.

(10) Patent No.: US 7,335,213 B1
(45) Date of Patent: Feb. 26, 2008

(54) APPARATUS AND METHODS FOR HEART VALVE REPAIR

(75) Inventors: Gregory Matthew Hyde, Menlo Park, CA (US); Mark Juravic, San Francisco, CA (US); Stephanie A. Szobota, Burlingame, CA (US); Brad David Bisson, Pearland, TX (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 636 days.

(21) Appl. No.: 10/298,133

(22) Filed: Nov. 15, 2002

(51) Int. Cl.
*A61B 17/08* (2006.01)
(52) U.S. Cl. ................................ 606/151
(58) Field of Classification Search ............ 606/60, 606/63, 68, 71, 72, 139, 142, 151, 157, 158
See application file for complete search history.

(56) References Cited

U.S. PATENT DOCUMENTS

| | | |
|---|---|---|
| 3,716,058 A | 2/1973 | Tanner, Jr. |
| 4,719,924 A | 1/1988 | Crittenden et al. |
| 4,781,186 A | 11/1988 | Simpson et al. |
| 4,830,023 A | 5/1989 | de Toledo et al. |
| 4,920,980 A | 5/1990 | Jackowski |
| 4,994,067 A | 2/1991 | Summers |
| 5,040,548 A | 8/1991 | Yock |
| 5,061,273 A | 10/1991 | Yock |
| 5,100,418 A * | 3/1992 | Yoon et al. ............ 606/139 |
| 5,171,233 A | 12/1992 | Amplatz et al. |
| 5,234,443 A | 8/1993 | Phan et al. |
| 5,242,456 A | 9/1993 | Nash et al. |
| 5,350,395 A | 9/1994 | Yock |
| 5,358,479 A | 10/1994 | Wilson |
| 5,383,260 A | 1/1995 | Deschenes et al. |
| 5,431,673 A | 7/1995 | Summers et al. |
| 5,441,483 A | 8/1995 | Avitall |
| 5,451,233 A | 9/1995 | Yock |
| 5,487,757 A | 1/1996 | Truckai et al. |
| 5,495,974 A | 3/1996 | Deschenes et al. |
| 5,518,162 A | 5/1996 | Deschenes et al. |
| 5,522,873 A | 6/1996 | Jackman et al. |
| 5,531,686 A | 7/1996 | Lundquist et al. |
| 5,554,184 A | 9/1996 | Machiraju |

(Continued)

FOREIGN PATENT DOCUMENTS

DE   10161543 A1   6/2003

(Continued)

OTHER PUBLICATIONS

Messas, et al., "Chordal Cutting a New Therapeutic Approach for Ischmic Mitral Regurgitaion," 2001, American Heart Association Inc., pp. 1958-1963.

(Continued)

*Primary Examiner*—Anhtuan T. Nguyen
*Assistant Examiner*—Tuan V. Nguyen
(74) *Attorney, Agent, or Firm*—Blakely, Sokoloff, Taylor & Zafman LLP

(57) ABSTRACT

Embodiments of a medical device and methods for percutaneously treating a heart valve. In one embodiment, the medical device has a first cardiac tissue fastener having a first lock, a second cardiac tissue fastener having a second lock, and a chord coupled to the first and second fasteners. Pulling the chord engages the first lock with the second lock.

19 Claims, 37 Drawing Sheets

U.S. PATENT DOCUMENTS

| | | |
|---|---|---|
| 5,569,277 A | 10/1996 | Evans et al. |
| 5,571,215 A | 11/1996 | Sterman et al. |
| 5,609,598 A | 3/1997 | Laufer et al. |
| 5,613,937 A | 3/1997 | Garrison et al. |
| 5,617,854 A | 4/1997 | Munsif |
| 5,632,754 A | 5/1997 | Farley et al. |
| 5,640,955 A | 6/1997 | Ockuly et al. |
| 5,642,736 A | 7/1997 | Avitall |
| 5,681,280 A | 10/1997 | Rusk et al. |
| 5,681,346 A | 10/1997 | Orth et al. |
| 5,682,906 A | 11/1997 | Sterman et al. |
| 5,687,723 A | 11/1997 | Avitall |
| 5,728,129 A | 3/1998 | Summers |
| 5,782,828 A | 7/1998 | Chen et al. |
| 5,810,882 A | 9/1998 | Bolduc et al. |
| 5,823,955 A | 10/1998 | Kuck et al. |
| 5,824,008 A | 10/1998 | Bolduc et al. |
| 5,865,800 A | 2/1999 | Mirarchi et al. |
| 5,868,733 A | 2/1999 | Ockuly et al. |
| 5,868,767 A | 2/1999 | Farley et al. |
| 5,916,213 A | 6/1999 | Haissaguerre et al. |
| 5,961,440 A | 10/1999 | Schweich, Jr. et al. |
| 5,964,772 A | 10/1999 | Bolduc et al. |
| 5,972,022 A | 10/1999 | Huxel |
| 5,989,284 A | 11/1999 | Laufer |
| 6,001,095 A | 12/1999 | de la Rama et al. |
| 6,001,104 A | 12/1999 | Benderev et al. |
| 6,001,127 A | 12/1999 | Schoon et al. |
| 6,004,332 A | 12/1999 | Yoon et al. |
| 6,017,358 A | 1/2000 | Yoon et al. |
| 6,021,340 A | 2/2000 | Randolph et al. |
| 6,027,514 A | 2/2000 | Stine |
| 6,036,715 A | 3/2000 | Yock |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,077,214 A | 6/2000 | Mortier et al. |
| 6,090,096 A | 7/2000 | St. Goar et al. |
| 6,093,199 A | 7/2000 | Brown et al. |
| 6,110,100 A | 8/2000 | Talpade |
| 6,113,609 A * | 9/2000 | Adams ................ 606/139 |
| 6,117,176 A | 9/2000 | Chen |
| 6,123,699 A | 9/2000 | Webster, Jr. |
| 6,149,669 A | 11/2000 | Li |
| 6,161,543 A | 12/2000 | Cox et al. |
| 6,162,168 A | 12/2000 | Schweich, Jr. et al. |
| 6,164,283 A | 12/2000 | Lesh |
| 6,165,119 A | 12/2000 | Schweich, Jr. et al. |
| 6,165,120 A | 12/2000 | Schweich, Jr. et al. |
| 6,165,164 A | 12/2000 | Hill et al. |
| 6,165,183 A | 12/2000 | Kuehn et al. |
| 6,165,197 A | 12/2000 | Yock |
| 6,174,323 B1 | 1/2001 | Biggs et al. |
| 6,178,346 B1 | 1/2001 | Amundson et al. |
| 6,182,664 B1 | 2/2001 | Cosgrove |
| 6,183,411 B1 | 2/2001 | Mortier et al. |
| 6,187,040 B1 | 2/2001 | Wright |
| 6,190,401 B1 | 2/2001 | Green et al. |
| 6,190,408 B1 | 2/2001 | Melvin |
| 6,203,531 B1 | 3/2001 | Ockuly et al. |
| 6,210,407 B1 | 4/2001 | Webster, Jr. |
| 6,210,432 B1 | 4/2001 | Solem et al. |
| 6,231,587 B1 | 5/2001 | Makower |
| 6,241,728 B1 | 6/2001 | Gaiser et al. |
| 6,254,568 B1 | 7/2001 | Ponzi |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,267,781 B1 | 7/2001 | Tu |
| 6,269,819 B1 | 8/2001 | Oz et al. |
| 6,270,526 B1 | 8/2001 | Cox |
| 6,283,127 B1 | 9/2001 | Sterman et al. |
| 6,283,962 B1 | 9/2001 | Tu et al. |
| 6,299,622 B1 | 10/2001 | Snow et al. |
| 6,306,133 B1 | 10/2001 | Tu et al. |
| 6,312,447 B1 | 11/2001 | Grimes |
| 6,325,823 B1 | 12/2001 | Horzewski et al. |
| 6,355,030 B1 | 3/2002 | Aldrich et al. |
| 6,371,978 B1 | 4/2002 | Wilson |
| 6,374,476 B1 | 4/2002 | Ponzi et al. |
| 6,402,780 B2 | 6/2002 | Williamson, IV et al. |
| 6,402,781 B1 | 6/2002 | Langberg et al. |
| 6,408,214 B1 | 6/2002 | Williams et al. |
| 6,419,696 B1 | 7/2002 | Ortiz et al. |
| 6,461,366 B1 | 10/2002 | Seguin |
| 6,482,224 B1 | 11/2002 | Michler et al. |
| 6,488,689 B1 | 12/2002 | Kaplan et al. |
| 6,493,575 B1 | 12/2002 | Kesten et al. |
| 6,497,707 B1 | 12/2002 | Bowman et al. |
| 6,500,167 B1 | 12/2002 | Webster, Jr. |
| 6,537,198 B1 | 3/2003 | Vidlund et al. |
| 6,537,314 B2 | 3/2003 | Langberg et al. |
| 6,551,271 B2 | 4/2003 | Nguyen |
| 6,554,794 B1 | 4/2003 | Mueller et al. |
| 6,585,718 B2 | 7/2003 | Hayzelden et al. |
| 6,599,311 B1 | 7/2003 | Biggs et al. |
| 6,605,086 B2 | 8/2003 | Hayzelden et al. |
| 6,610,058 B2 | 8/2003 | Flores |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,638,286 B1 | 10/2003 | Burbank et al. |
| 6,648,903 B1 | 11/2003 | Pierson, III |
| 6,656,221 B2 | 12/2003 | Taylor et al. |
| 6,676,702 B2 | 1/2004 | Mathis |
| 6,706,065 B2 | 3/2004 | Langberg et al. |
| 6,709,442 B2 | 3/2004 | Miller et al. |
| 6,709,456 B2 | 3/2004 | Langberg et al. |
| 6,712,804 B2 | 3/2004 | Roue et al. |
| 6,718,985 B2 * | 4/2004 | Hlavka et al. ............ 128/898 |
| 6,719,767 B1 * | 4/2004 | Kimblad ................ 606/151 |
| 6,723,038 B1 | 4/2004 | Schroeder |
| 6,733,500 B2 | 5/2004 | Kelley et al. |
| 6,755,812 B2 | 6/2004 | Peterson et al. |
| 6,761,734 B2 | 7/2004 | Suhr |
| 6,764,510 B2 | 7/2004 | Vidlund et al. |
| 6,790,231 B2 | 9/2004 | Liddicoat et al. |
| 6,800,090 B2 | 10/2004 | Alferness et al. |
| 6,810,882 B2 | 11/2004 | Langberg |
| 6,824,562 B2 | 11/2004 | Mathis et al. |
| 6,852,124 B2 | 2/2005 | Cox et al. |
| 6,890,353 B2 | 5/2005 | Cohn et al. |
| 6,905,476 B2 | 6/2005 | Ponzi |
| 6,960,229 B2 | 11/2005 | Mathis et al. |
| 6,964,683 B2 | 11/2005 | Kowalsky et al. |
| 6,966,926 B2 | 11/2005 | Mathis |
| 6,989,028 B2 | 1/2006 | Lashinski et al. |
| 6,997,951 B2 | 2/2006 | Solem et al. |
| 7,073,504 B2 | 7/2006 | Callister et al. |
| 2001/0003986 A1 | 6/2001 | Cosgrove |
| 2001/0005787 A1 | 6/2001 | Oz et al. |
| 2001/0018611 A1 | 8/2001 | Solem et al. |
| 2001/0044568 A1 | 11/2001 | Langberg et al. |
| 2002/0010483 A1 | 1/2002 | Folmer et al. |
| 2002/0010486 A1 | 1/2002 | Hirt |
| 2002/0013571 A1 | 1/2002 | Goldfarb et al. |
| 2002/0016628 A1 | 2/2002 | Langberg et al. |
| 2002/0026216 A1 | 2/2002 | Grimes |
| 2002/0035361 A1 | 3/2002 | Houser et al. |
| 2002/0042651 A1 | 4/2002 | Liddicoat et al. |
| 2002/0077647 A1 | 6/2002 | Snow et al. |
| 2002/0087169 A1 | 7/2002 | Brock et al. |
| 2002/0087173 A1 | 7/2002 | Alferness et al. |

| | | |
|---|---|---|
| 2002/0103492 A1 | 8/2002 | Kaplan et al. |
| 2002/0103532 A1 | 8/2002 | Langberg et al. |
| 2002/0103533 A1 | 8/2002 | Langberg et al. |
| 2002/0111637 A1 | 8/2002 | Kaplan et al. |
| 2002/0161330 A1 | 10/2002 | Nguyen |
| 2002/0165484 A1 | 11/2002 | Bowe et al. |
| 2002/0165533 A1 | 11/2002 | Flores |
| 2002/0165534 A1 | 11/2002 | Hayzelden et al. |
| 2002/0169502 A1 | 11/2002 | Mathis |
| 2002/0169504 A1 | 11/2002 | Alferness et al. |
| 2002/0183836 A1 | 12/2002 | Liddicoat et al. |
| 2002/0183837 A1 | 12/2002 | Streeter et al. |
| 2002/0183841 A1 | 12/2002 | Cohn et al. |
| 2002/0188170 A1 | 12/2002 | Santamore et al. |
| 2003/0050598 A1 | 3/2003 | Hayzelden et al. |
| 2003/0069593 A1 | 4/2003 | Tremulis et al. |
| 2003/0078465 A1 | 4/2003 | Pai et al. |
| 2003/0083538 A1 | 5/2003 | Adams et al.. |
| 2003/0093071 A1 | 5/2003 | Hauck et al. |
| 2003/0105520 A1 | 6/2003 | Alferness et al. |
| 2003/0120340 A1 | 6/2003 | Liska et al. |
| 2003/0120341 A1 | 6/2003 | Shennib et al. |
| 2003/0130731 A1 | 7/2003 | Vidlund et al. |
| 2003/0144697 A1 | 7/2003 | Mathis |
| 2003/0144732 A1 | 7/2003 | Cosgrove et al. |
| 2003/0167071 A1 | 9/2003 | Martin et al. |
| 2003/0171776 A1 | 9/2003 | Adams et al. |
| 2003/0212453 A1 | 11/2003 | Mathis et al. |
| 2003/0216764 A1 | 11/2003 | Tu et al. |
| 2004/0010231 A1 | 1/2004 | Leonhardt et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0059531 A1 | 3/2004 | Eigler et al. |
| 2004/0098092 A1 | 5/2004 | Butaric et al. |
| 2004/0138683 A1 | 7/2004 | Shelton et al. |
| 2004/0138744 A1 | 7/2004 | Lashinski et al. |
| 2004/0148020 A1 | 7/2004 | Vidlund et al. |
| 2004/0153147 A1 | 8/2004 | Mathis |
| 2005/0045183 A1 | 3/2005 | Callister et al. |
| 2005/0055089 A1 | 3/2005 | Macoviak et al. |
| 2005/0085844 A1 | 4/2005 | Tremulis et al. |
| 2005/0209633 A1 | 9/2005 | Callister et al. |
| 2005/0267571 A1 | 12/2005 | Spence et al. |
| 2005/0267573 A9 | 12/2005 | Macoviak et al. |
| 2006/0041306 A1 | 2/2006 | Vidlund et al. |
| 2006/0095025 A1 | 5/2006 | Levine et al. |

FOREIGN PATENT DOCUMENTS

| | | |
|---|---|---|
| EP | 0 377 269 A | 7/1990 |
| WO | WO 98/29041 A1 | 7/1998 |
| WO | WO 99/00059 | 1/1999 |
| WO | WO 99/13777 | 3/1999 |
| WO | WO 99/30647 A1 | 6/1999 |
| WO | WO 99/44534 A1 | 9/1999 |
| WO | WO 00/03759 | 1/2000 |
| WO | WO 00/06026 A2 | 2/2000 |
| WO | WO 00/06028 A1 | 2/2000 |
| WO | WO 00/66027 A2 | 2/2000 |
| WO | WO 00/16700 A1 | 3/2000 |
| WO | WO 00/60995 | 10/2000 |
| WO | WO 01/00111 A1 | 1/2001 |
| WO | WO 01/00114 A1 | 1/2001 |
| WO | WO 01/26557 A1 | 4/2001 |
| WO | WO 01/28432 A1 | 4/2001 |
| WO | WO 01/28455 A1 | 4/2001 |
| WO | WO 01/49213 A2 | 7/2001 |
| WO | WO 01/49213 A3 | 7/2001 |
| WO | WO 01/54618 A1 | 8/2001 |
| WO | WO 01/89440 A2 | 11/2001 |
| WO | WO 02/00099 A2 | 1/2002 |
| WO | WO 02/01999 A2 | 1/2002 |
| WO | WO 02/34167 A2 | 5/2002 |
| WO | WO 02/39925 A2 | 5/2002 |
| WO | WO 02/053206 A2 | 7/2002 |
| WO | WO 02/060352 | 8/2002 |
| WO | WO 02/062263 A2 | 8/2002 |
| WO | WO 02/062263 A3 | 8/2002 |
| WO | WO 02/062270 A1 | 8/2002 |
| WO | WO 02/062408 A2 | 8/2002 |
| WO | WO 02/063533 | 8/2002 |
| WO | WO 02/078576 | 10/2002 |
| WO | WO 03/049619 A2 | 6/2003 |
| WO | WO 03/073913 A2 | 9/2003 |
| WO | WO 2004/012789 A2 | 2/2004 |
| WO | WO 2004/014282 A2 | 2/2004 |

OTHER PUBLICATIONS

PCT Invitation to Pay Additional fees for PCT International Appln. No. US03/36633, mailed May 19, 2004 (5 pages).

Bonow, R., et al., "Guidelines for the Management of Patients With Valvular Heart Disease," Executive Summary, A Report of the American College of Cardiology/American Heart Association Task Force on Practice Guidelines (Committee on Management of Patients With Valvular Heart Disease), ACC/AHA Practice Guidelines, pp. 1949-1984.

PCT International Search Report for PCT Application No. US2004/031403. Mailed on Feb. 15, 2005 (5 Pages).

* cited by examiner

APPARATUS AND METHODS FOR HEART VALVE REPAIR

TECHNICAL FIELD

The disclosure, in one embodiment, relates generally to the treatment of heart related diseases, and more particularly, in one embodiment, to the treatment of defective heart valves.

BACKGROUND

FIG. 1A illustrates a heart 10 with a partial internal view and arrows indicating the direction of blood flow within the heart. Four valves in the heart 10 direct the flow of blood within the left and right sides of the heart. The four valves include a mitral valve 20, an aortic valve 18, a tricuspid valve 60, and a pulmonary valve 62 as illustrated in FIG. 1A. The mitral valve 20 is located between the left atrium 12 and the left ventricle 14. The aortic valve 18 is located between the left ventricle 14 and the aorta 16. These two valves direct oxygenated blood coming from the lungs, through the left side of the heart, into the aorta 16 for distribution to the body. The tricuspid valve 60 is located between the right atrium 22 and the right ventricle 24. The pulmonary valve 62 is located between the right ventricle 24 and the pulmonary artery 26. These two valves direct de-oxygenated blood coming from the body, through the right side of the heart, into the pulmonary artery 26 for distribution to the lungs, where it again becomes re-oxygenated and distributed to the mitral valve 20 and the aortic valve 18.

The heart valves are complex structures. Each valve has "leaflets" that open and close to regulate the direction of blood flow. The mitral valve 20 has two leaflets and the tricuspid valve 60 has three leaflets. The aortic 18 and pulmonary 62 valves have leaflets that are referred to as "cusps," because of their half-moon like shapes. The aortic 18 and pulmonary 62 valves each have three cusps.

During diastole, the leaflets of the mitral valve 20 open, allowing blood to flow from the left atrium 12 to fill the left ventricle 14. During systole, the left ventricle 14 contracts, the mitral valve 20 closes (i.e., the leaflets of the mitral valve 20 re-approximate), and the aortic valve 18 opens allowing oxygenated blood to be pumped from the left ventricle 14 into the aorta 16. A properly functioning mitral valve 20 allows blood to flow into the left ventricle and prevents leakage or regurgitation of blood back into the left atrium (and subsequently back into the lungs). The aortic valve 18 allows blood to flow into the aorta 16 and prevents leakage (or regurgitation) of blood back into the left ventricle 14. The tricuspid valve 60 functions similarly to the mitral valve 20 to allow deoxygenated blood to flow into the right ventricle 24. The pulmonary valve 62 functions in the same manner as the aortic valve 18 in response to relaxation and contraction of the right ventricle 24 (i.e., to move de-oxygenated blood into the pulmonary artery 26 and subsequently to the lungs for re-oxygenation).

During relaxation and expansion of the ventricles 14, 24, (i.e., diastole), the mitral 20 and tricuspid 60 valves open, while the aortic 18 and pulmonary 62 valves close. When the ventricles 14, 24, contract (i.e., systole), the mitral 20 and tricuspid 60 valves close and the aortic 18 and pulmonary 62 valves open. In this manner, blood is propelled through both sides of the heart (as indicated by the arrows of FIG. 1A).

Regurgitation is a condition in which leaflets of a heart valve do not close completely, resulting in the backflow of blood. For instance, in a condition typically referred to as mitral valve prolapse (also known as mitral valve regurgitation), the leaflets of the mitral valve do not close completely during systole and blood leaks back into the left atrium. The heart is then forced to work harder to pump enough oxygenated blood to the body. This may lead to heart damage over a period of time. Regurgitation is common, occurring in approximately 7% of the population. Mitral valve regurgitation may be caused by a number of conditions, including genetic defects, infections, coronary artery disease (CAD), myocardial infarction (MI), or congestive heart failure (CHF).

Faulty or defective valves may be treated with various surgical procedures. Annuloplasty, illustrated in FIG. 1B, is one type of a surgical procedure that has been used to treat regurgitation. Annuloplasty 30 involves a synthetic ring 32 that is placed around a valve rim (annulus) 34 of a heart valve. Sutures 38 attach the valve annulus 34 to the synthetic ring 32. Synthetic ring 32 reduces the size of valve opening 36, causing the valve to close properly. FIG. 1C illustrates another surgical procedure in which a heart valve such as the mitral valve 20 is repaired by reconstruction. First, at step A, a section P2 from the posterior leaflet 40 of the mitral valve 20 is excised. Then, sequentially at steps B, C, D, and E, sections P1 and P3 of the posterior leaflet 40 are sutured together. The reconstruction shrinks the size of the valve opening 36. In some instances, a faulty or defective valve must be surgically replaced with a new valve. Examples of new valves include homograft valves (valves harvested from human cadavers), artificial mitral valves, and mechanical valves.

The procedures discussed above are typically major, invasive surgical procedures that may require opening the chest by sternotomy, making incisions in the chest wall, heart-lung bypass and suspending the beating of the heart. These invasive procedures subject patients to a tremendous amount of pain and discomfort. Moreover, these procedures require lengthy recovery and/or hospitalization periods. Patients with congestive heart failure may not be able to tolerate the surgical procedures described above, leaving them with little or no alternative to treat their defective heart valves.

SUMMARY

Embodiments of a medical device and methods for percutaneously treating a heart valve are described. In one embodiment, the medical device has a first cardiac tissue fastener having a first lock, a second cardiac tissue fastener having a second lock, and a chord coupled to the first and second fasteners. Pulling the chord engages the first lock with the second lock.

Additional embodiments, features and advantages of the medical device will be apparent from the accompanying drawings, and from the detailed description that follows below.

BRIEF DESCRIPTION OF THE DRAWINGS

The present disclosure is illustrated by way of example, and not limitation, in the figures of the accompanying drawings in which.

DETAILED DESCRIPTION

Figure 1A:
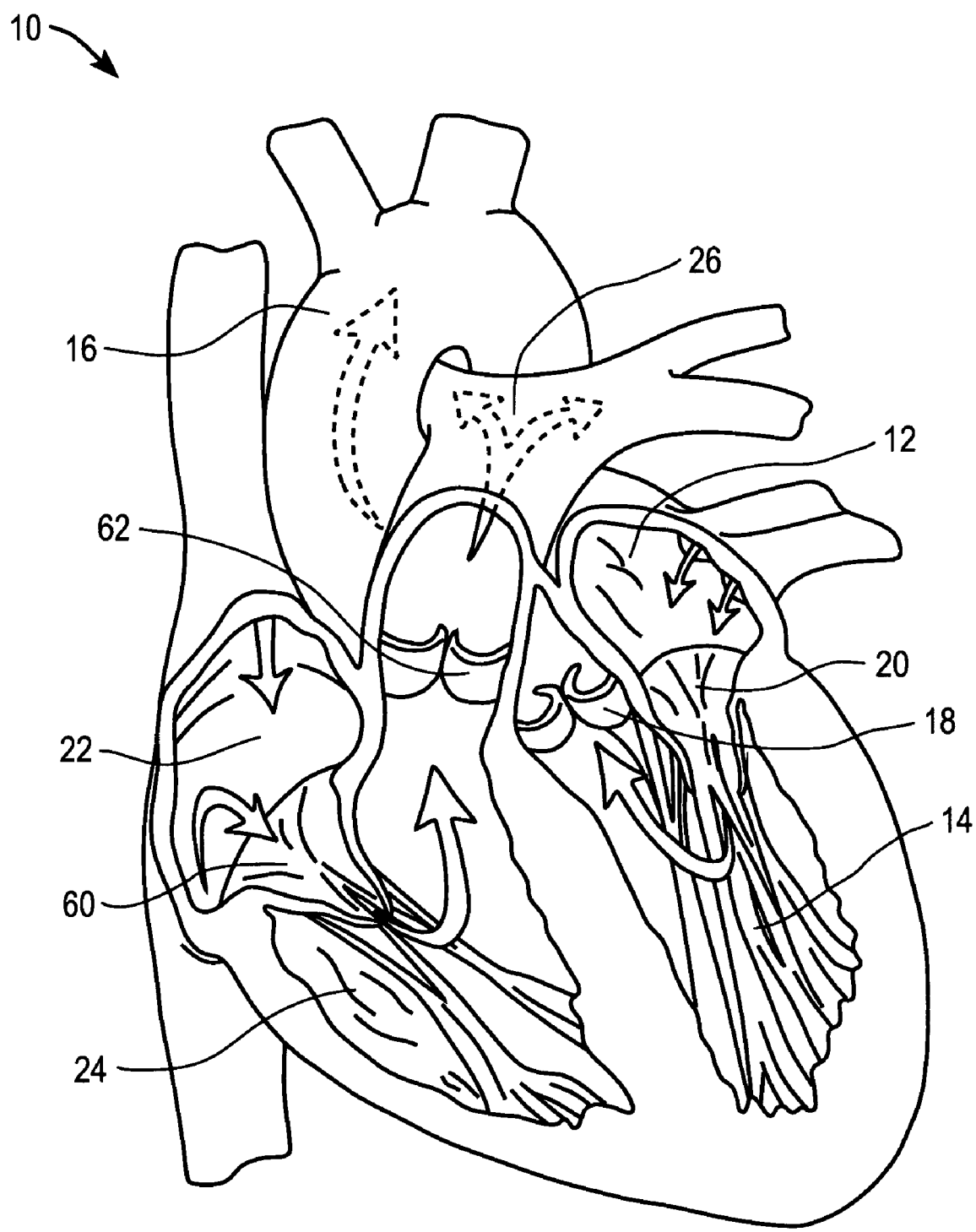
FIG. 1A illustrates a heart.
Figure 1B:
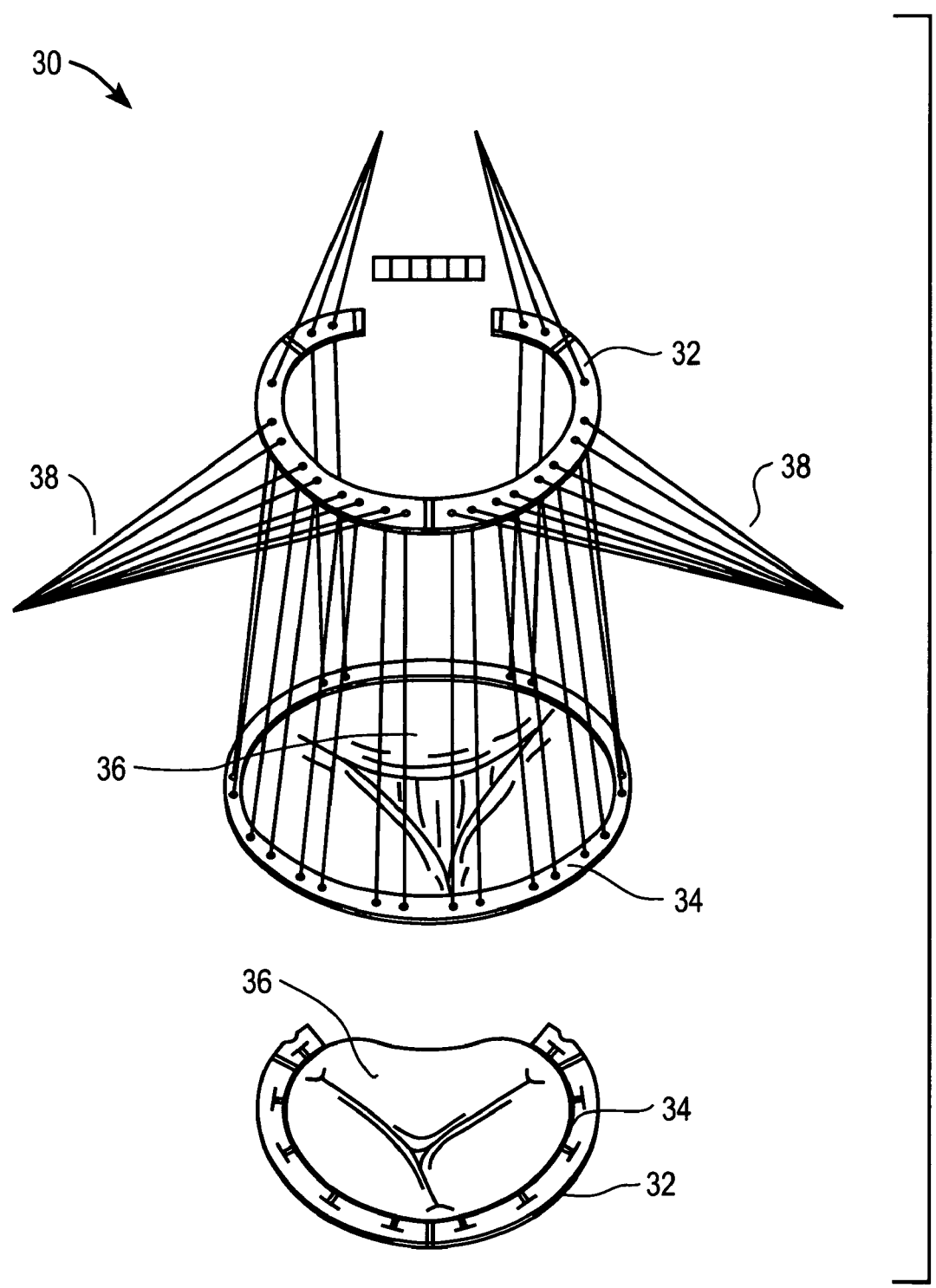
FIG. 1B illustrates an annuloplasty procedure to constrict a defective valve.
Figure 1C:
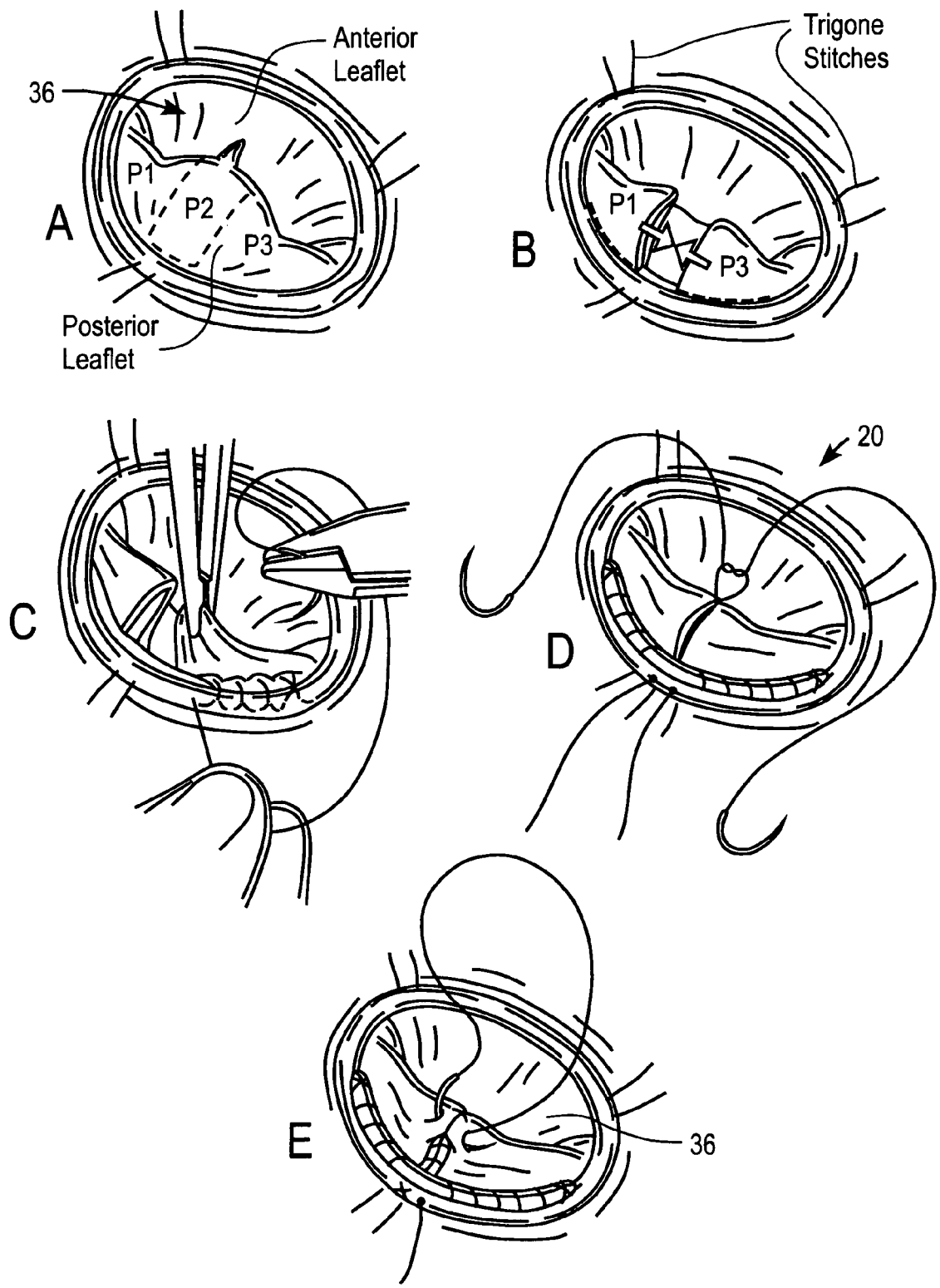
FIG. 1C illustrates a reconstruction procedure to reduce the size of a defective valve.

In the following description, numerous specific details are set forth such as examples of specific materials or components in order to provide a thorough understanding of the present disclosure. It will be apparent, however, to one skilled in the art that these specific details need not be employed to practice the disclosure. In other instances, well known components or methods have not been described in detail in order to avoid unnecessarily obscuring the present disclosure. Embodiments of a medical device discussed below are described with respect to the treatment of a valve such as a mitral valve. It may be appreciated, however, that other heart valves or body tissue may be treated, and embodiments of the medical device are not limited in their applicability to treating the heart.

Embodiments of a medical device and methods for treating a heart valve, such as the mitral valve, percutaneously are described. A medical device, in one embodiment, may be used to treat mitral valve regurgitation or prolapse. In one embodiment, the medical device includes a first cardiac tissue fastener having a first lock, a second cardiac fastener having a second lock, and a chord coupling the first and second fasteners together. Pulling the chord engages the first and second locks together to adjust a distance between the first and second fasteners. In one embodiment, first lock may be an elongated tubing extending from the first clip, and second lock may also be an elongated tubing extending from the second clip. A surface of the first lock has a series of ridges that may engage an inner surface of the second lock to enable the two locks to move with respect to each other in one direction only.

In one embodiment of a method for treating a heart valve, a first clip is percutaneously advanced (e.g., through a guiding catheter) to a heart valve region (e.g., the mitral valve) and attached to a desired tissue (e.g., mitral valve leaflet). Next, a second clip is percutaneously advanced to the heart valve and similarly attached to another desired tissue (e.g., another mitral valve leaflet). A first lock extends proximally from the first clip and a second lock extends proximally from the second clip such that the two clips face away from each other. A chord extends from the first clip, through the first and second locks, to the second clip and back near a proximal portion of the guiding catheter. The chord is pulled (e.g., by a user or operator) to bring the first and second locks toward each other. An outer surface of the first lock may fit inside and secure itself within an inner surface of the second lock.

In another embodiment, a medical device is described. The medical device includes a support annulus including a length corresponding to a circumference of one of an interior portion of an atrium and an atrioventricular valve annulus (e.g. a mitral valve). In one embodiment, the support annulus has a circular, ring shape. The support annulus is suitable for percutaneous delivery to a patient offering an improvement in atrioventricular valve modification over more invasive surgical procedures.

Figure 2:
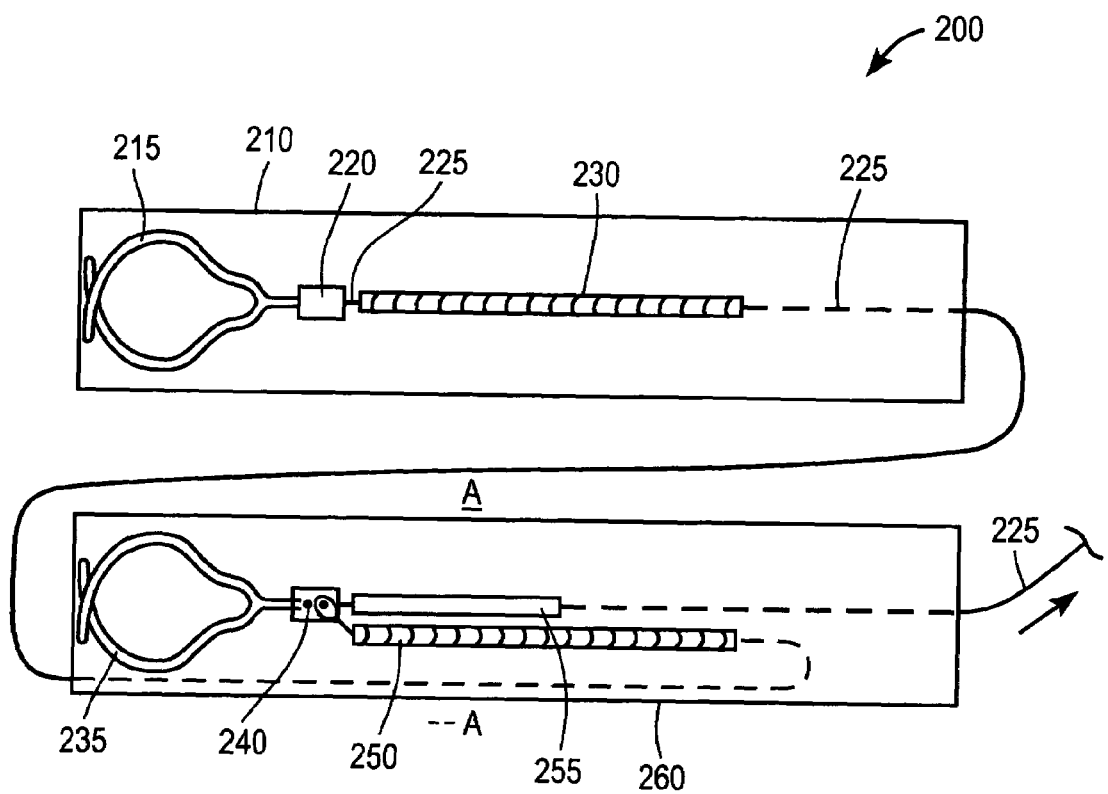
FIG. 2 illustrates one embodiment of a percutaneous medical device having dual clips before deployment.

FIG. 2 illustrates an exemplary embodiment of a medical device which may be used to treat a defective heart valve by controlling or stabilizing tissue in the valve region. For example, in one embodiment, the opening and closing of the two mitral valve leaflets may be controlled by clipping them together. The medical device 200 has a first clip 215 that may be deployed from sheath 210. First clip 215 may be, in one embodiment, a self expanding clip made from a shape memory alloy or metal such as Nitinol. First clip 215 remains in a compressed position while in sheath 210. In one embodiment, first clip 215 has a c-shape structure. In an alternative embodiment, first clip 215 may have helical or spiral structure (not shown). A clip connector 220 may be formed near a proximal end of clip 215, to which a chord 225 is coupled. A first lock 230 is disposed proximal to first clip 215, with chord 225 tracked within it and extending out of sheath 210. As described in greater detail below, first lock 230 engages a second lock 250 disposed near second clip 235.

Second clip 235 is illustrated disposed and in a compressed position within second sheath 260. Second clip 235 may be structurally similar to first clip 215, having a second clip connector 240 coupled near a proximal end of second clip 235. Second clip lock 250 and a mandrel 255 are also disposed near a proximal end of second clip 235. In one embodiment, mandrel 255 may be used to extend second clip 235 from sheath 260. Chord 225 may be tracked through second lock 250, through second clip connector 240, through mandrel 255, and extending out of second sheath 260. As such, chord 225, in one embodiment, is in contact with the various elements of medical device 200. When clips 215, 235 have been deployed from sheaths 210, 260 respectively, and clipped to a desired body tissue (e.g., mitral valve leaflets), chord 225 may be pulled in the direction of the arrow as shown (i.e., in a proximal direction), to bring first lock 230 towards second lock 250. First and second locks 230, 250 mechanically engage each other to secure a desired, user adjustable, distance between first and second clips 215, 235. These first and second locks form an embodiment of an adjustable connector which has an adjustable length.

Figure 37:
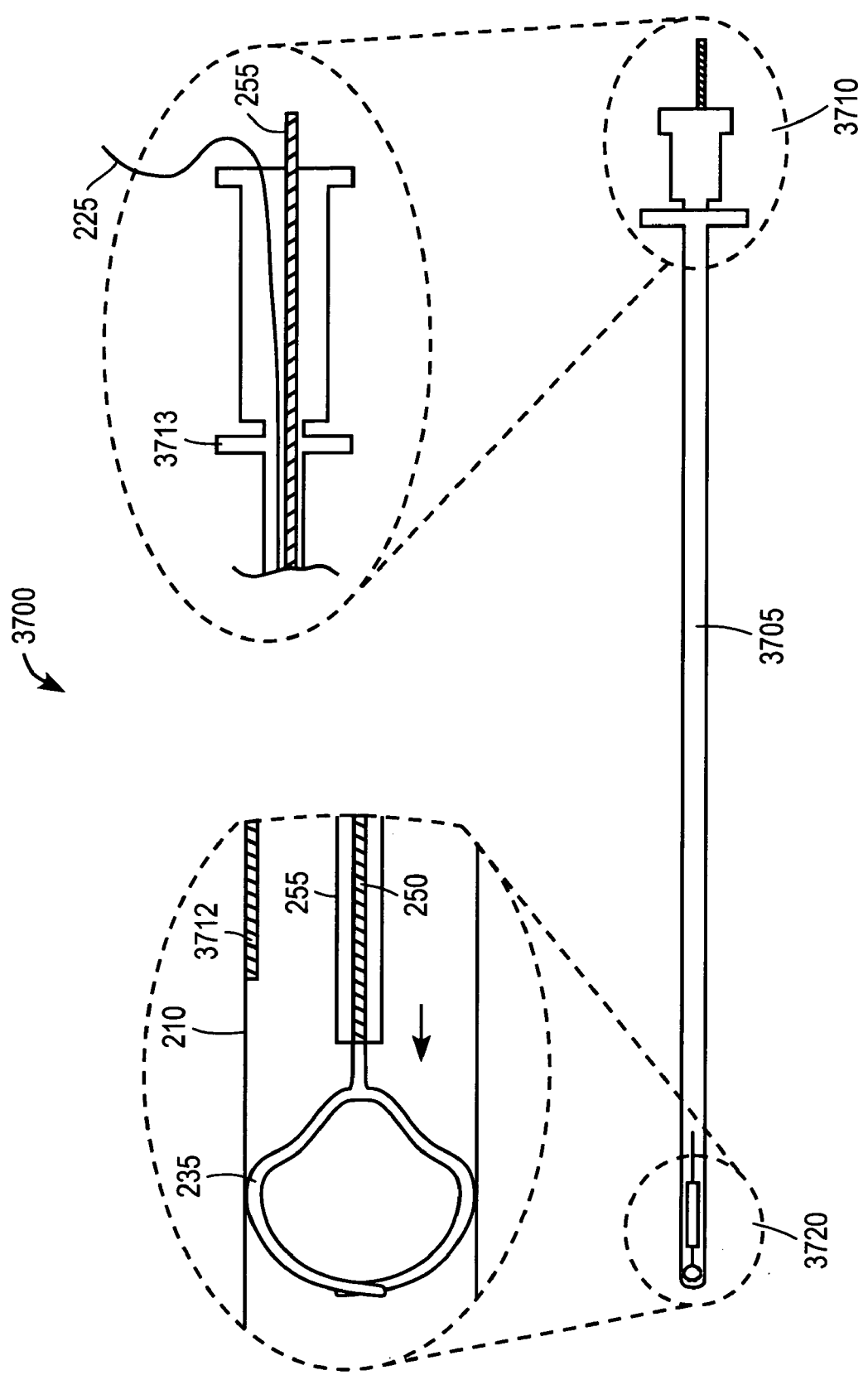
FIG. 37 illustrates a schematic side view of an embodiment of a medical device 3700 that may be used to deliver clip near a mitral valve percutaneously.

FIG. 37 illustrates one embodiment of a side view of a medical device 3700 that may be use to deliver clip 235 percutaneously. Device 3700 has a proximal portion 3710, a distal portion 3720, and an elongated catheter portion 3705. Proximal portion 3710 may be, in one embodiment, a control mechanism or handle for an operator to control distal portion 3720 when treating a patient. The enlarged view of distal portion 3720 shows clip 235 compressed within a lumen formed within sheath 210. Clip 235 is coupled to clip lock 250 that extends proximally away from clip 235. A mandrel or push rod 255 may disposed over clip lock 250. As discussed above, mandrel 255 may be used to release clip 235 from sheath 210. Mandrel 255 extends all the way back to proximal portion 3710 as shown in the enlarged view of proximal portion 3710. An operator may push mandrel 255 in the distal direction to release clip 235 from sheath 210. A steering tendon 3712 may also be disposed within catheter 3705 extending towards distal portion 3720. Steering tendons for catheters are well known in the art. Control knob 3713 disposed near proximal portion 3710 may be used to steer tendon 3712 to guide distal portion 3720 through tortuous vessels to a target region within a patient's heart. A clip chord is coupled to clip 235 and is tracked through lock 250 and mandrel 255 back to proximal portion 3710.

Figure 3:
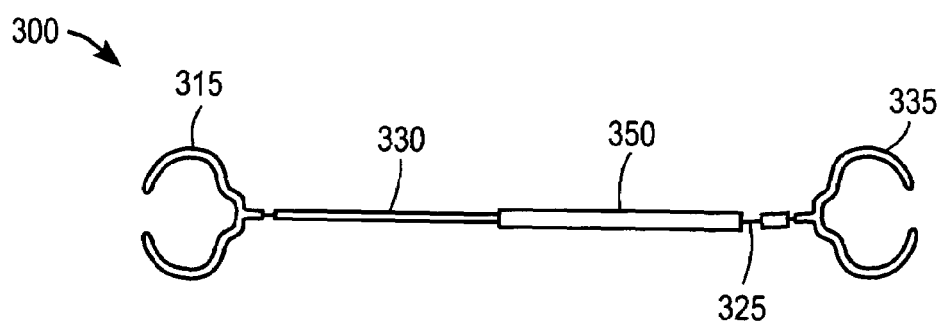
FIG. 3 illustrates one embodiment of a percutaneous medical device having dual clips after deployment.

FIG. 3 illustrates one embodiment of a medical device 300 that has been fully deployed, and having a user adjustable distance between the clips 315, 335 set and locked. For example, medical device 300 may have been deployed from the sheaths (210, 260) described above with respect to FIG. 2. In one embodiment, first lock 330 is secured within second lock 350, with chord 325 tracked within the locks and coupled to first and second clips 315, 335.

Figure 4A:
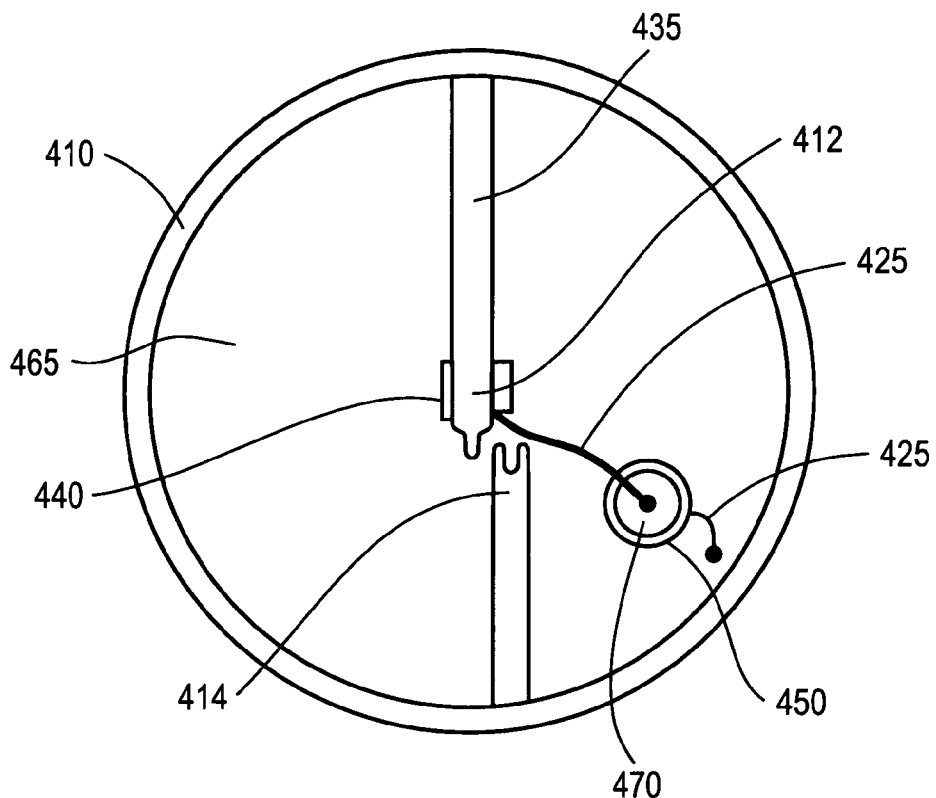
FIG. 4A illustrates one embodiment of an end view of a percutaneous clip prior to deployment.

FIG. 4A illustrates an end view of a second clip 435 disposed within sheath 410 of a catheter. In one embodiment, the view illustrated in FIG. 4A may be understood with respect to second clip 235 of FIG. 2. Sheath 410 forms a lumen 465 that maintains first and second clip ends 412, 414 of clip 435 compressed within sheath 410. Clip ends 412, 414 extend back towards clip connector 440. Also disposed within lumen 465 are lock 450 (e.g., second lock 240 of FIG. 2) and chord 425 (which corresponds to chord 225 of FIG. 2). Chord 425 is coupled to clip connector 440 and is tracked through a lumen 470 formed within lock 450. In one embodiment, chord 425 may be tracked by entering sheath 410 from its distal end to a rear end of lock 450 and through lumen 470 of lock 450 towards clip connector 440. Chord 425 may then continue to be tracked away from clip 435.

Figure 4B:
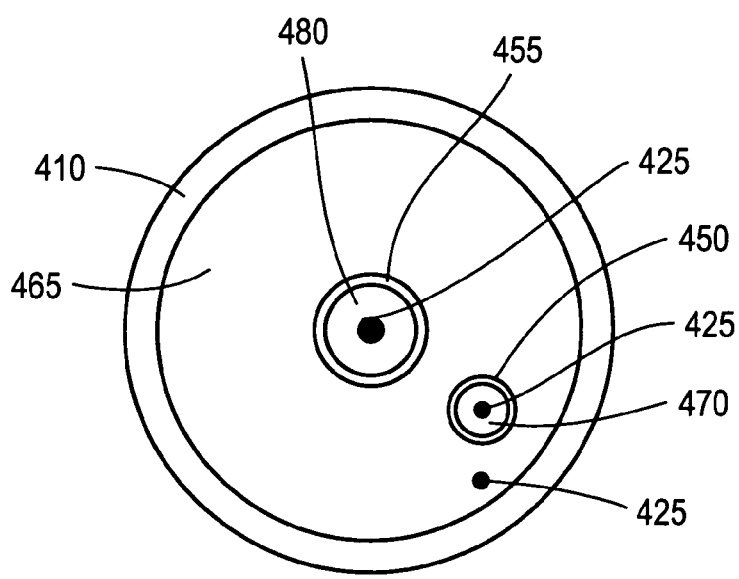
FIG. 4B illustrates a cross-sectional view taken along line A-A of FIG. 2.

FIG. 4B illustrates a cross-sectional view of a clip assembly taken along line A-A of FIG. 2. Sheath 410 forms a lumen 465 that contains a mandrel 455 disposed near a center portion of lumen 465. Mandrel 455 may form a lumen 480 within it. Lock 450 is also disposed within lumen 465 of sheath 410. Chord 425 is illustrated disposed within lumen 465 of sheath 410, lumen 480 of mandrel 455, and lumen 470 of lock 450.

Figure 5A:
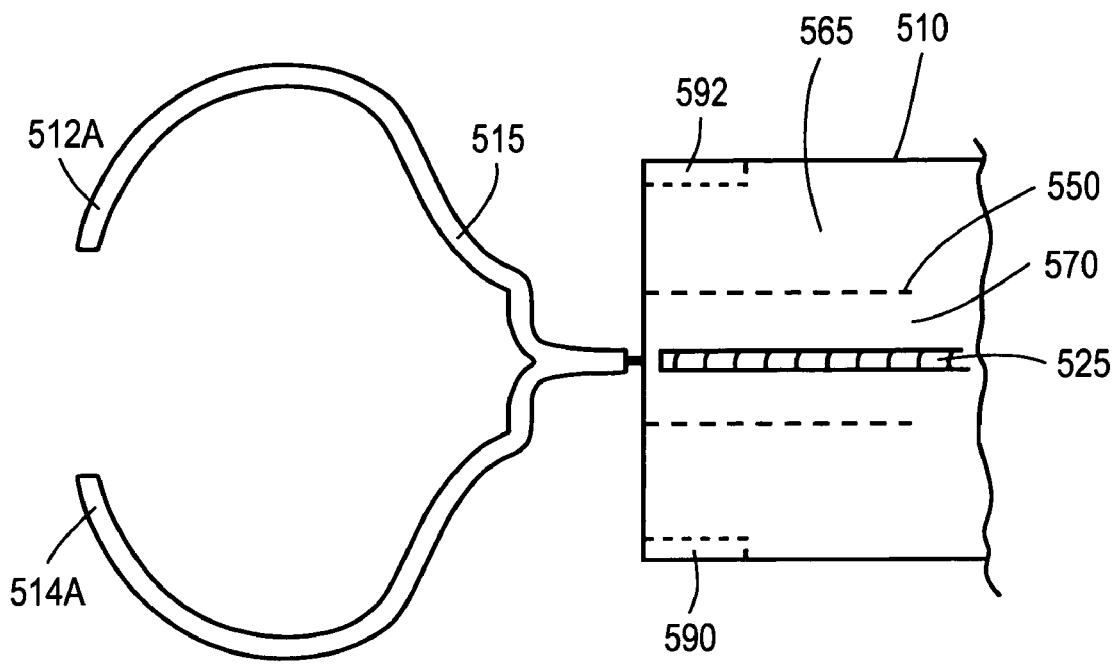
FIG. 5A illustrates one embodiment of a clip extended from a sheath.
Figure 5B:
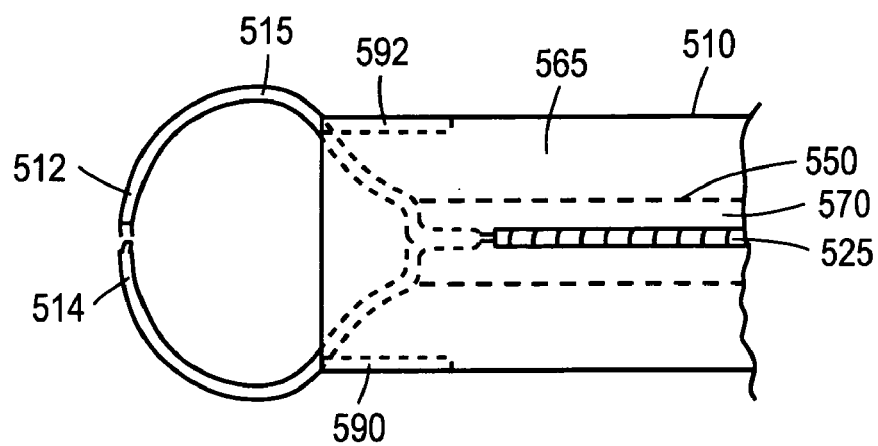
FIG. 5B illustrates one embodiment of a clip that has been partially retracted to bring the ends of the clip together.

FIGS. 5A-5B illustrate a partial see-through view of one embodiment of the mechanical motion of a clip (e.g., clip 215) for grasping or engaging a body tissue or mitral valve. FIG. 5A illustrates clip 515 (corresponding to clip 215), having first and second ends 512, 514 extended from sheath 510 (which corresponds to sheath 210). The embodiment of clip 515 as shown has a c-shape, but other shapes or structural designs may be envisioned for clip 515 to one of skill in the art. When extended from sheath 510, ends 512, 514 spread apart to create sufficient space to orient themselves on opposite sides of target body tissue. Chord 525 is coupled to clip 515 near a proximal end of clip 515 and extends through a lumen 570 (corresponding to lumen 470) formed by lock 550 (e.g., first lock 250). Lock 550 may be disposed within lumen 565 (corresponding to lumen 465) of sheath 510 (corresponding to sheath 410). Clip 515 may be made of a material rigid enough to penetrate a body tissue. In one embodiment, the entire structure of clip 515 or just first and second ends 512, 514 may be made of stainless steel. In another embodiment, all or portions of clip 515A may be made of comparable metallic material to that of stainless steel known to one of skill in the art, including shape memory alloys (e.g., nickel-titanium, also referred to as "NiTi" or "NiTinol"). In another alternative embodiment, all or portions of clip 515 may be made of ceramic or material which are compatible with MRI (magnetic resonance imaging) in that the materials do not introduce artifacts in MRI images. Lumen 565 of sheath 510 may also have one or more aligners 590, 592 that help align clip 515 as it is retracted to bring ends 512 and 514 closer together to grasp a desired tissue.

FIG. 5B illustrates clip 515 partially retracted within sheath 510, thereby bringing ends 512, 514 together. In one embodiment, sheath 510 may be advanced towards a relatively stationary clip 515 to contact aligner 590 with one end of clip 515, and aligner 592 with the other end of clip 515. Alternatively, the clip 515 may be pulled towards the sheath 510 while the sheath is relatively stationary. Aligners 590, 592 straighten clip 515 so that ends 512, 514 may apply a substantially equal force toward each other. It may be understood that after clip 515 extends from sheath 510, clip 515 may move or rotate freely. Thus, achieving a proper orientation of clip 515 may be important to attach a desired body tissue securely. Alternatively, ends 512, 514 of clip 515 may be compressed toward each other by pulling on chord 525 coupled to clip 515. This would produce the same effect on clip 515 as advancing sheath 510 towards clip 515.

Figure 5C:
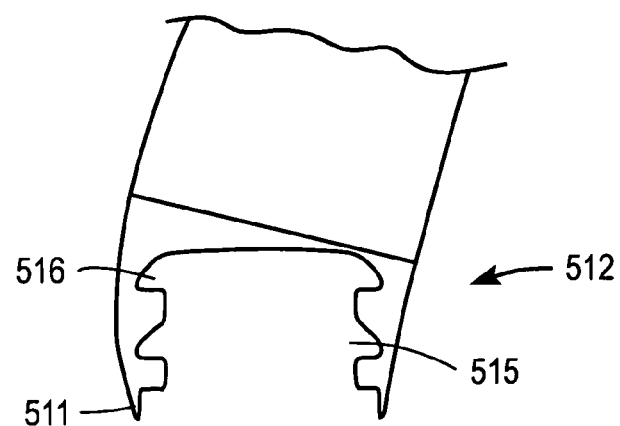
FIG. 5C illustrates one embodiment of clip ends.
Figure 5C:
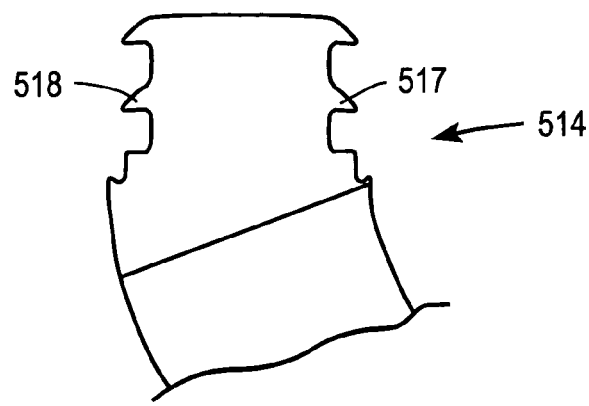
Figure 5D:
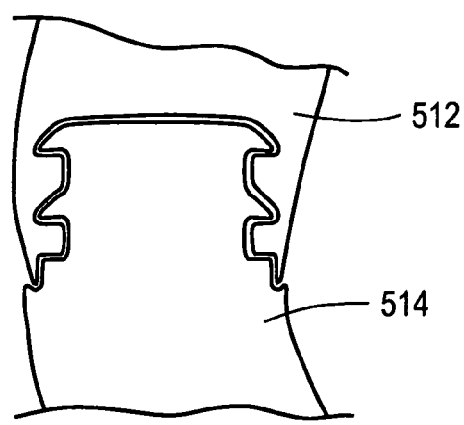
FIG. 5D illustrates another embodiment of clip ends in a locked position.

FIGS. 5C-5D illustrate one exemplary embodiment of a structure for clip ends (e.g., ends 512, 514), and the mechanics by which they engage to lock with each other. As discussed above, a sheath (e.g., sheath 510B) is moved relative to the clip (e.g., the sheath is advanced toward the clip) to force the clip ends together. As illustrated by FIG. 5C, clip end 512 is shaped to be compatible with the opposing clip end 514. Clip end 512 may have grooves 515, 516 adapted to receive ridges 517, 518 of opposing clip end 514. Clip 512 may be referred to as the "female" clip end and clip 514 may be referred to as the "male" clip end. Female clip end 512 may have one or more barbs 511 to facilitate the piercing of a body tissue or mitral valve leaflet. FIG. 5D illustrates clip ends 512, 514 locked with each other. The structure of the clip ends may be analogous to a ratchet such that once the ridges or teeth from clip end 514 have nested within the grooves of opposing clip end 512, the cannot be separated from each other. The mechanics of the clip ends securely attaches the clip to a desired body tissue. At this point, the clip sheath may be retracted, leaving the clip in the locked position.

Figure 6A:
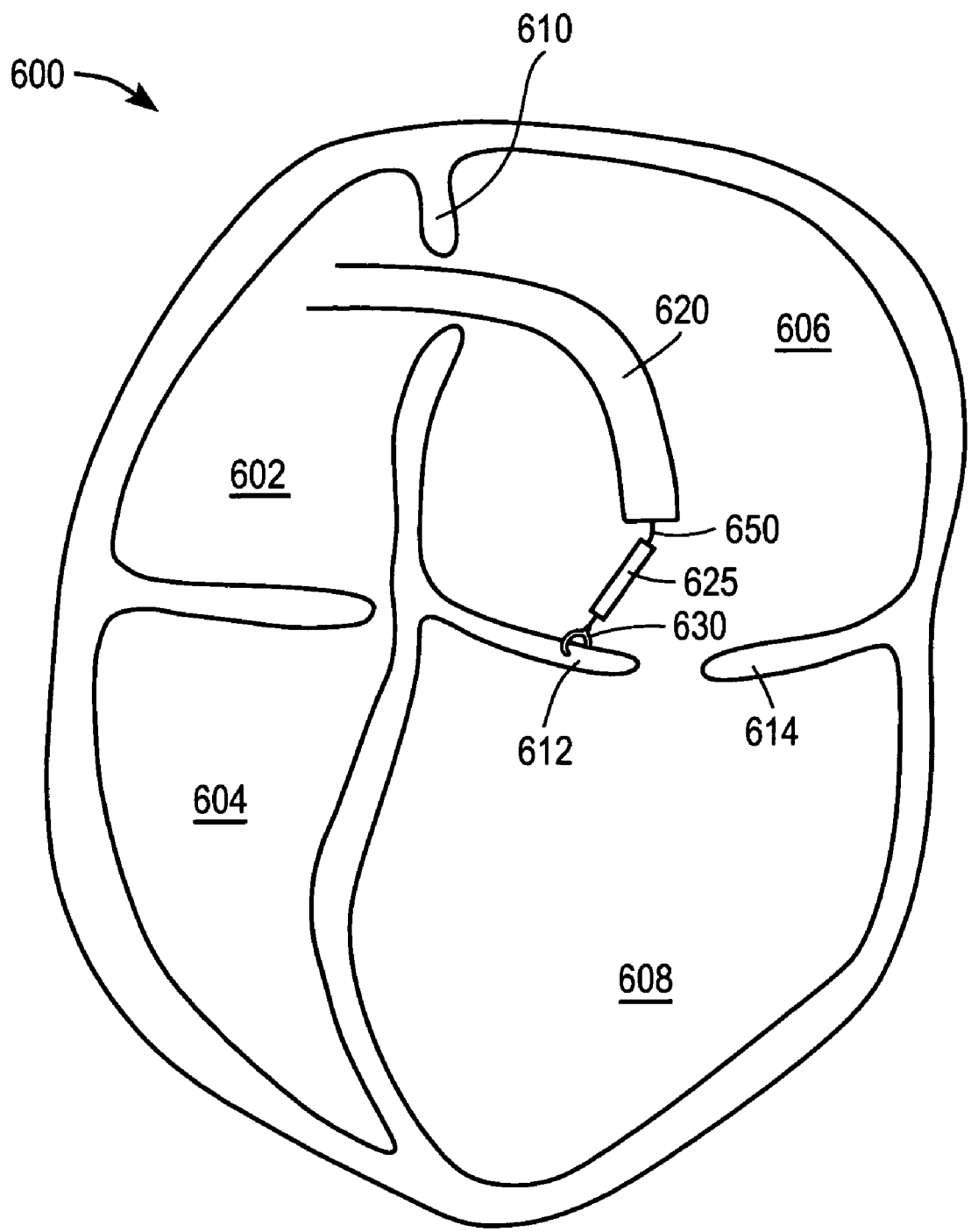
FIG. 6A illustrates one embodiment of a first clip percutaneously deployed and attached to a first mitral valve leaflet.
Figure 6B:
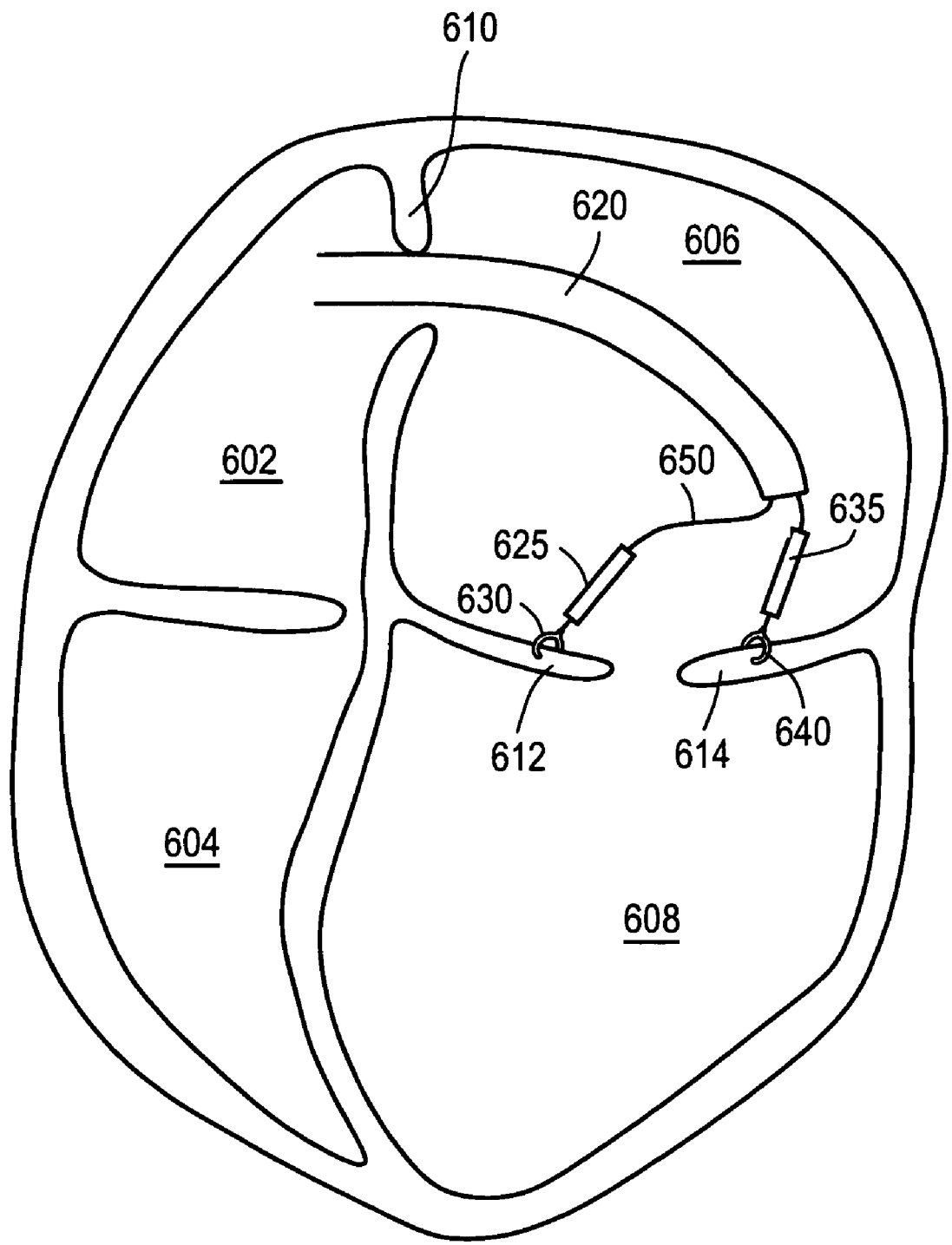
FIG. 6B illustrates one embodiment of a second clip percutaneously deployed and attached to a second mitral valve leaflet.
Figure 6C:
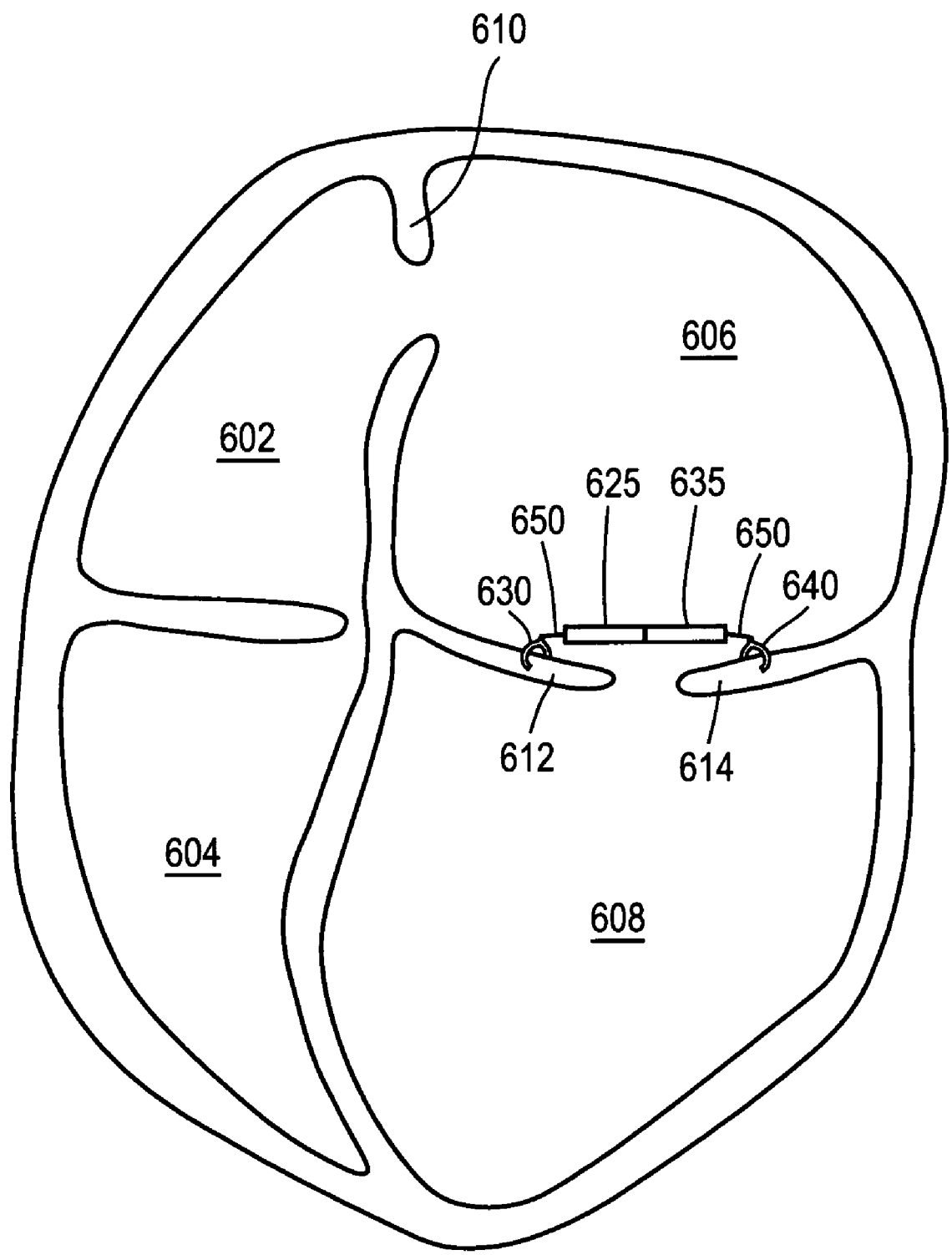
FIG. 6C illustrates one embodiment of a first and second clip deployed and locked between two mitral valve leaflets.

FIGS. 6A-6C illustrate one exemplary method of deploying clip connectors to each leaflet of a mitral valve, with a distance between the leaflets adjusted and locked with a locking mechanism integrated with the clips. FIG. 6A illustrates a simplified view of the heart having four chambers including right atrium 602, right ventricle 604, left atrium 606, and left ventricle 608. Septum 610 separates right atrium 602 from left atrium 608. A distal catheter portion 620 (e.g., a catheter containing the medical device 200) of a medical device is percutaneously advanced, through the venuous vasculature, to near mitral valve leaflets 612, 614 by crossing/piercing septum 610 from the right atrium 602 to the left atrium 608. A guidewire, such as a guidewire catheter, (not shown) may be initially positioned within the left atrium. Catheter portion 620 may be loaded and tracked with the guidewire to be positioned near leaflets 612, 614. The guidewire may, in one embodiment, have a steerable end which includes on or more pull tendons, extending from near the distal end of the guidewire to a proximal end which includes a control mechanism, coupled to the one or more pull tendons, for selectively pulling the pull tendons in order to steer the distal end of the guidewire. Each pull tendon of the one or more pull tendons are disposed with a lumen which allows the respective pull tendon to be pulled. The guidewire allows for control of the positioning of the distal end of catheter 620. The catheter 620 includes a lumen to hold at least a distal portion of the guidewire near a distal portion of the catheter 620. Alternatively, the catheter 620, may include one or more pull down tendons, each within a lumen, that allow for steering of the distal end of catheter 620 from a control mechanism, at the proximal end of catheter 620, which control mechanism is coupled to each of the pull tendons. In other embodiments, catheter portion 620 may be any of the catheter types used in the art, including but not limited to "rapid exchange" (RX) catheters, "over-the-wire" (OTW) catheters, or a "tip RX" catheters. Methods for puncturing and accessing the left atrium with a catheter are well known in the art; accordingly, a detailed description is not provided. Various imaging techniques known in the art may also be used to locate the mitral valve leaflets. For example, echo imaging, infrared illumination, x-ray, and magnetic resonance imaging methods may be utilized. These imaging techniques are known in the art; accordingly, a detailed description is not provided.

First clip 630 (such as clip 215) is illustrated having been deployed and attached to mitral valve leaflet 612. First lock 625 (such as lock 230) may be disposed near first clip 630, with chord 650 (such as chord 225) tracked through first lock 625 and coupled to first clip 630. The mechanics of first clip 630 may operate, in one embodiment, as described above with respect to FIGS. 5A-5D.

FIG. 6B illustrates another simplified view of a heart with chambers right atrium 602, right ventricle 604, left atrium 606, and left ventricle 608. The description of FIG. 6B may be understood, in one embodiment, to have followed the deployment of first clip 630 of FIG. 6A. FIG. 6B shows a first clip 630 attached to a first mitral valve leaflet 612. A distal portion of catheter 620 extends across septum 610 and is positioned over second mitral valve leaflet 614. A second clip 640 (such as clip 235) extends from catheter 620, with second lock 635 (such as lock 250 of FIG. 2) disposed near second clip 640. A chord 650 coupled to first clip 630 extends through first lock 625 (such as lock 230 of FIG. 2) and back within catheter portion 620. As described in greater detail below, chord 650 is tracked back down catheter 620 and coupled to second clip 640 through second lock 635. The second clip 640 is attached to the second mitral valve leaflet 614, and after attachment, the length of the connector may be adjusted in accordance with the description.

FIG. 6C illustrates another simplified view of a heart with chambers right atrium 602, right ventricle 604, left atrium 606, and left ventricle 608. The description of FIG. 6C may be understood, in one embodiment, to have followed the deployment of first clip 630 and second clip 640 of FIG. 6B. The catheter (e.g., catheter 620) that deployed first and second clips 630, 640 has been removed after having adjusted the length of the connection between the two clips. First clip 630 is secured to first mitral valve leaflet 612 and second clip 640 is secured to second mitral valve leaflet 614. A distance between first and second clips have been adjusted and set by engaging first lock 625 with second lock 635. In one embodiment, first and second locks 625, 635 operate analogously to a ratchet, to allow movement in one direction only (e.g., towards each other). Chord 650 is coupled to first and second clips 630, 640 and is tracked within first and second locks 625, 635.

In an alternative embodiment, first and second clips 630, 640 may be deployed to attach a mitral valve leaflet to a portion of the left ventricular tissue. For example, first clip 630 may be attached to leaflet 614 and second clip 640 may be attached to a papillary muscle (not shown) within the left ventricle 608. This form of attachment enables the clip assembly to serve as a tether or chordae. It may be appreciated that other types of attachment variations within the heart chambers may be formed with first and second clips 630, 640.

Figure 7A:
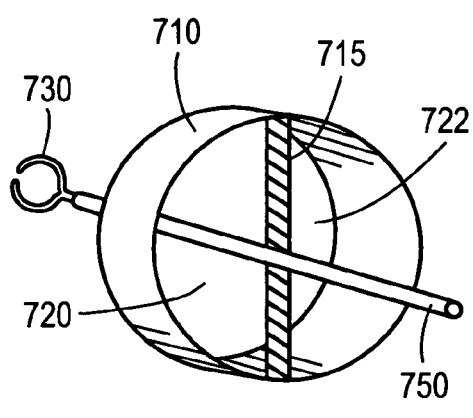
FIG. 7A illustrates one embodiment of a proximal end view of a catheter to deliver a first clip.
Figure 7B:
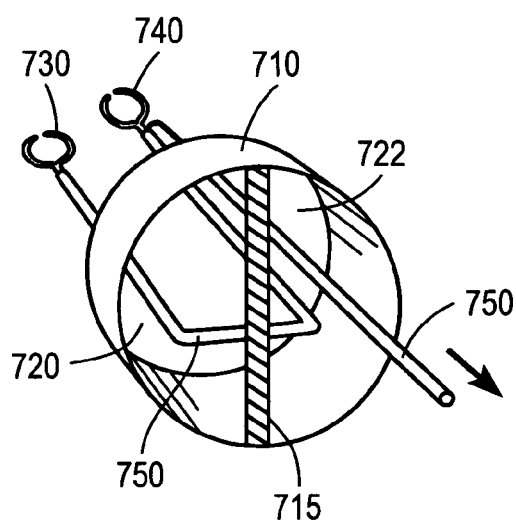
FIG. 7B illustrates another embodiment of a proximal end view of a catheter to deliver a first clip and a second clip.

FIGS. 7A-7B illustrate a proximal portion of a catheter to deliver first and second clips percutaneously. As illustrated by FIG. 7A, catheter 710, in one embodiment, may have a partition 715 that forms a first lumen 720 and a second lumen 722. Partition 715 does not necessarily have to extend down the entire length of the catheter 710. In one embodiment, partition 715 may be a bar having a length approximately equal to a diameter of catheter 710, and disposed near a proximal end of catheter 710. A first clip assembly 730 (shown in a simplified form) (such as clip 215 compressed within sheath 210 along with first lock 230 as illustrated in FIG. 2) may be percutaneously advanced down lumen 720 and deployed (e.g., according to the method described above). It should be noted that clip assembly 730 is represented in a simplified form with the clip assumed to be deployed from its sheath and locked to a target tissue. However, clip assembly 730 would be advanced down one side of catheter 710 in the form illustrated in FIG. 2. Chord 750 (such as chord 225) coupled to first clip 730 may be tracked back to the proximal portion of catheter 710 and be coupled to a control mechanism at the proximal end of the catheter 710.

Figure 7C:
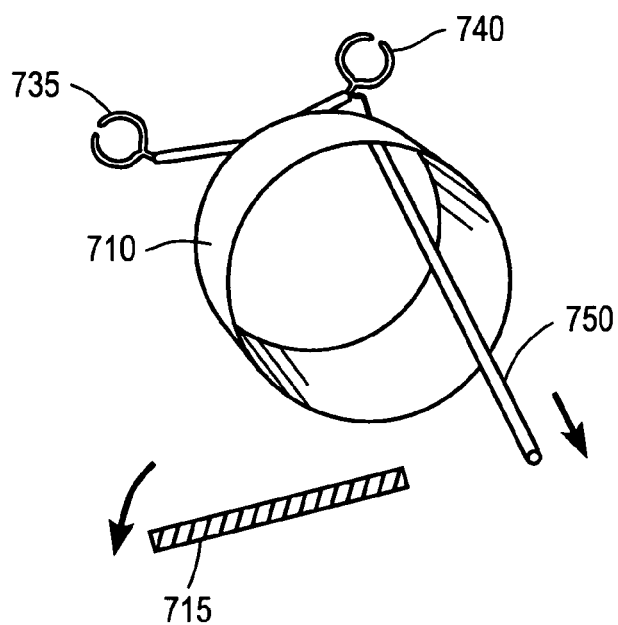
FIG. 7C illustrates another embodiment of a proximal end view of a catheter to lock a distance between a first and a second clip.

FIG. 7B illustrates a second clip 740 (such as clip 235) deployed through a second lumen 722 in addition to a first clip 735 deployed through first lumen 720. Chord 750 is tracked continuously from first clip 730 back through lumen 720 and down lumen 722 to coupled second clip 740, and back again through lumen 722 past a proximal portion of catheter 710. Again, it should be understood that second clip 740 is illustrated in a simplified form. In practice, second clip 740 would be advanced down lumen 722 of catheter 710 in the form illustrated in FIG. 2. Then, as illustrated by FIG. 7C, by continuing to pull on chord 750, first clip 730 is pulled towards second clip 740. The shortening of chord 750 between the first and second clips 730, 740 dislodges partition 715 from within catheter 710 as shown. Once a desired distance between first and second clips 730, 740 has been achieved (e.g., with first and second locks 625, 635 locked together as discussed above), chord 750 may be severed and removed from catheter 710. As such, partition 715 enables first and second clips 730, 740 to be independently deployed and then locked together while tethered with chord 750. In one embodiment, chord 750 may be severed by advancing a catheter having a cutting element disposed near its distal end to the portion of the chord to be cut. Such cutting catheters are known in the art.

Figure 8A:
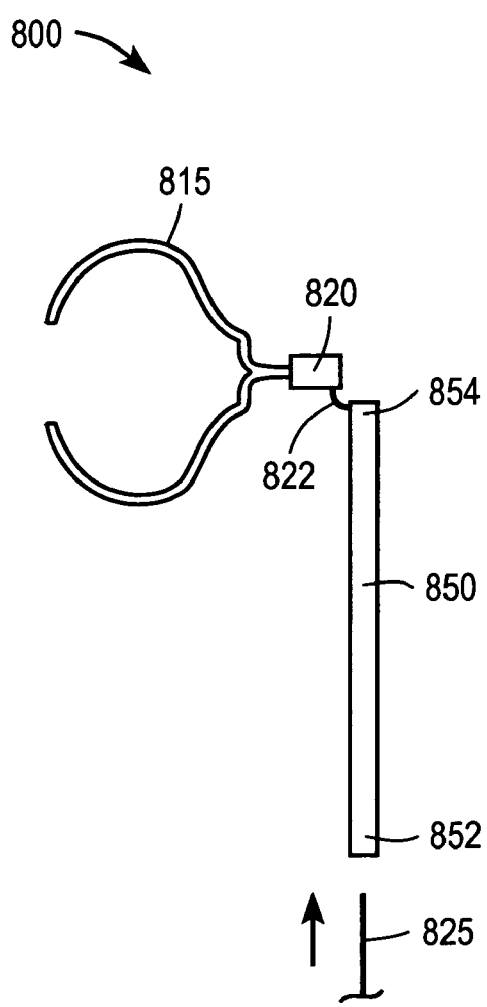
FIG. 8A illustrates one embodiment of tracking a chord to the second clip.
Figure 8B:
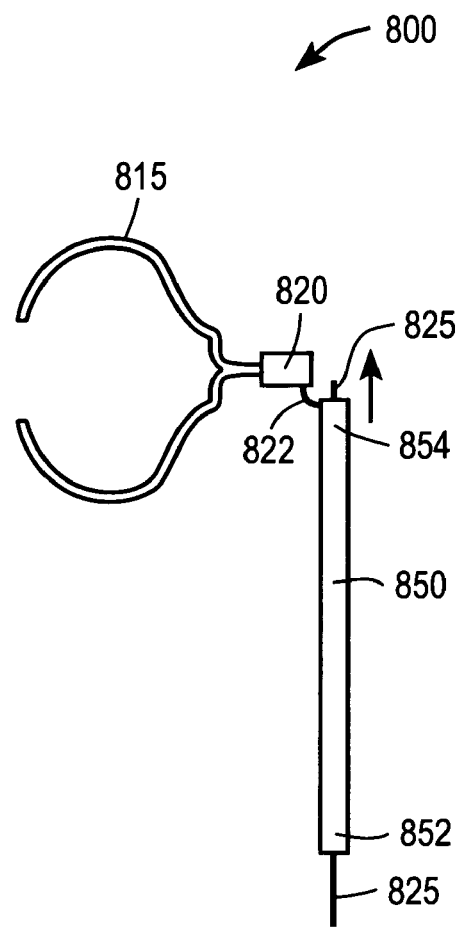
FIG. 8B illustrates another embodiment of tracking a chord to the second clip.

FIGS. 8A-9B illustrate the process by which a chord is tracked from a first clip, after it has been deployed, to a second clip. As discussed above, in one embodiment, a chord tethers the first and second clips such that a pulling of the chord locks them together. In one embodiment, a chord is tethered from a first clip to a second clip after the first clip has been deployed but before the second clip is deployed. A simplified representation of second clip 800 is shown without a sheath or housing member (e.g., second clip 235 compressed in sheath 260 of FIG. 2). For the purposes of describing the actions represented by FIGS. 8A-9B, it may be assumed that a first clip has been deployed and attached to a body tissue, such as a mitral valve leaflet (e.g., FIG. 6A). As illustrated by FIG. 8A, second clip 800 (such as clip 235) has a c-shaped clip 815 and is coupled to a clip connector 820 (such as clip connector 240). A second lock 850 (such as lock 250) is disposed near clip connector 820 and coupled to clip connector 820 by attachment member 822. A lumen (not shown) may be formed within lock 850 to receive chord 825 (such as chord 225) extending from a first clip. As illustrated by FIG. 8B, chord 825 is inserted from a proximal end 852 of lock 850 and tracked through a lumen of the lock 850 past a distal end 854.

Figure 9A:
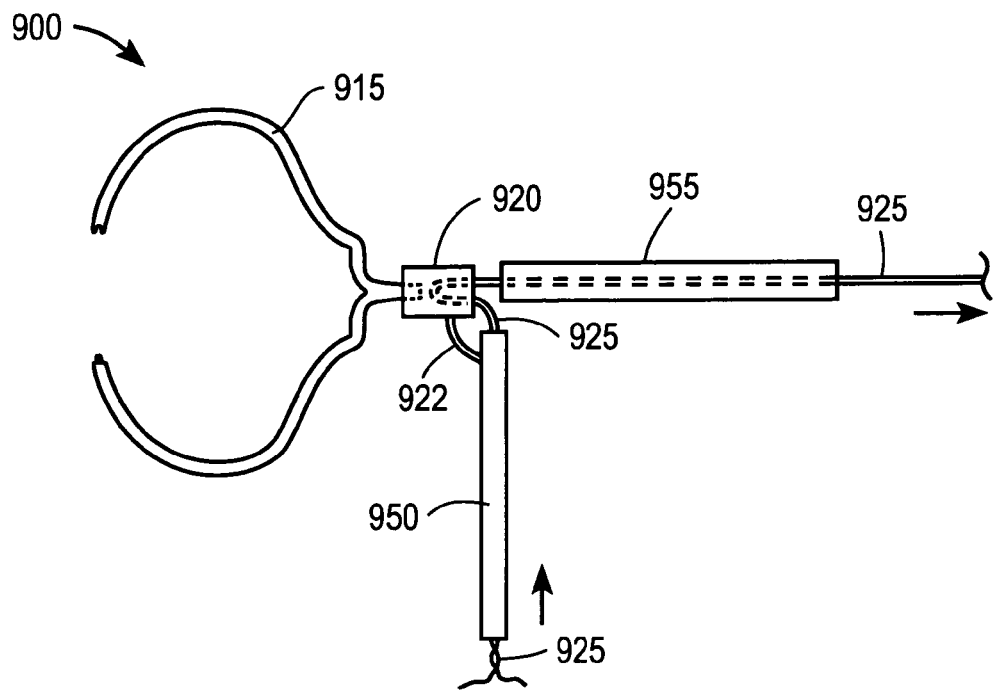
FIG. 9A illustrates one embodiment of tracking a chord from a second lock through the second clip.
Figure 9B:
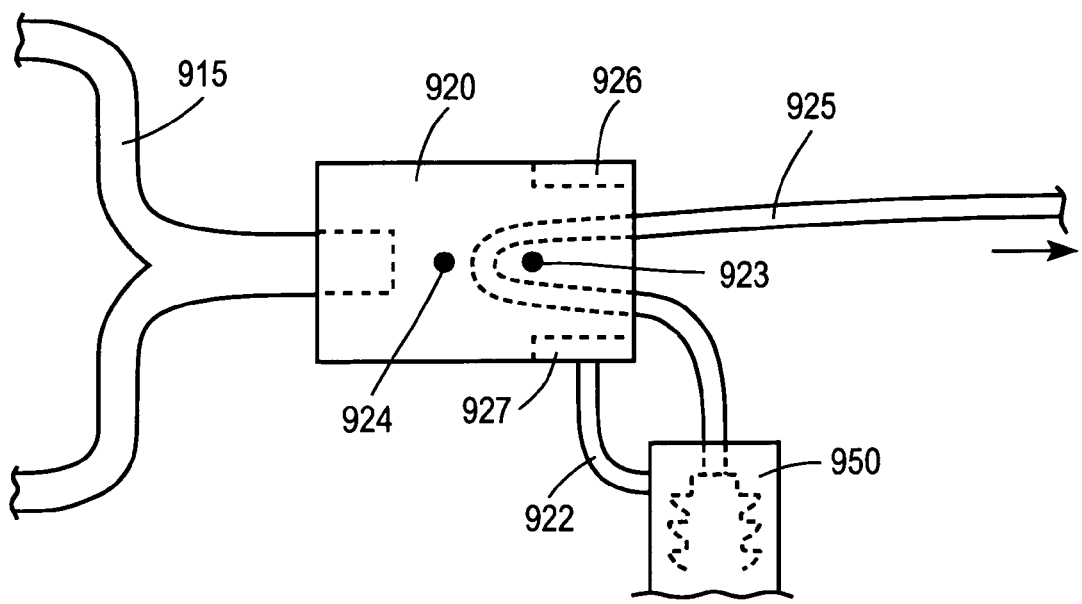
FIG. 9B illustrates one embodiment of an enlarged view of tracking a chord from a second lock through the second clip.

FIGS. 9A-9B illustrate enlarged views of a clip connector portion of clip 900. Chord 925 is tracked through lock 950, in and out of clip connector 920, and through an extending mandrel 955 in the direction of the arrows and indicated. The overall path of chord 925 may be representative of the path of chord 750 as discussed above with respect to FIG. 7B. FIG. 9A illustrates how chord 925 couples the various elements of a two clip medical device. Chord 925 is tracked through a lumen within lock 950, through slots formed within clip connector 920 (which is coupled to clip 915) and through a lumen formed within mandrel 955. Mandrel 955 may be used to extend clip 915 from a sheath (e.g., sheath 260) for attaching to a mitral valve leaflet. FIG. 9B illustrates an even larger view of the clip connector 920 region to show the path of chord 925 passing through it from lock 950. One or more dividers 923, 924 may be disposed within clip connector 920 to direct the path of chord 925 in and out of clip connector 920. Clip connector 920 may also be fitted with alignment members 926, 927 to engage mandrel 955 when used to extend clip 915 from its sheath. In one embodiment, chord 925 may be tracked through second lock 950 and clip connector 920 after a first clip has been deployed. Thus, the integration of chord 925 to a second clip assembly may be accomplished externally (i.e., outside of a patient). Then, second clip 915 and second lock may be placed within a sheath (e.g., sheath 260) and percutaneously advanced down a guiding catheter (e.g., catheter 710B) for deployment. In an alternative embodiment, chord 925 may be tracked from second lock 950 to mandrel 955 without passing through clip connector 920. Because attachment 922 couples second lock 950 to clip connector 920, chord 925 does not need to be integrated within clip connector 920.

Figure 10A:
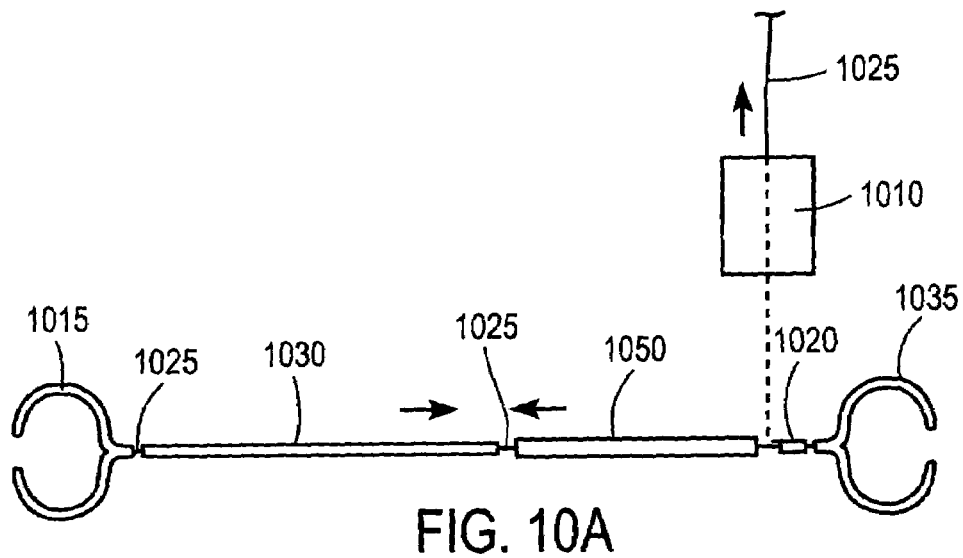
FIG. 10A illustrates one embodiment of a first lock and a second lock being pulled towards each other.
Figure 10B:
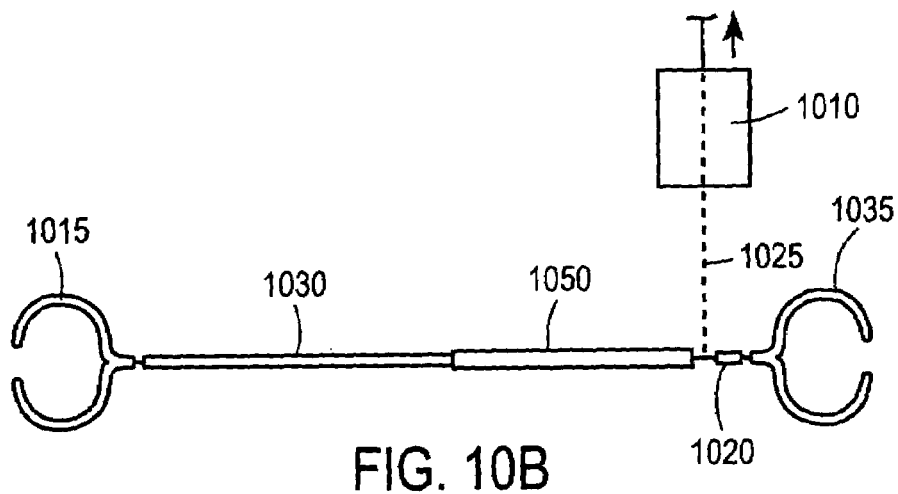
FIG. 10B illustrates one embodiment of a first lock and a second lock being locked with each other.

FIGS. 10A-10B illustrate the action of the locks from each clip engaging each other when a chord that tethers both clips is pulled. FIG. 10A illustrates first lock 1030 disposed near first clip 1015 and a second lock 1035 disposed near second lock 1050. Chord 1025 is coupled to first clip 1015 and tracked within the lumens of first and second locks 1030, 1050 to clip connector 1020. Chord 1025 passed in and out of clip connector 1020 as described above and past a proximal end of catheter 1010. By pulling on chord 1025 in the direction as indicated by the arrow, first clip 1015 is drawn towards second clip 1035. This has the effect of engaging first lock 1030 with second lock 1050. In one embodiment, first lock may be designed to fit within an inner surface of second lock 1050. First clip may be drawn towards second clip to any desired distance afforded by a length of the locks. In one embodiment, first and second locks 1030, 1050 may have substantially similar lengths. FIG. 10B illustrates first and second locks 1030, 1050 secured in a lock position with first lock 1030 fitted within second lock 1050. The design of the first and second locks 1030, 1050 may be such that they may move with respect to each other in just one direction. For example, once first and second locks have engaged each other, they may only move closer together, and not apart from each other. Once a desired distance between first and second clips 1030, 1050 have been achieved, chord 1025 may be severed near clip connector 1020 and removed through catheter 1010.

Figure 11:
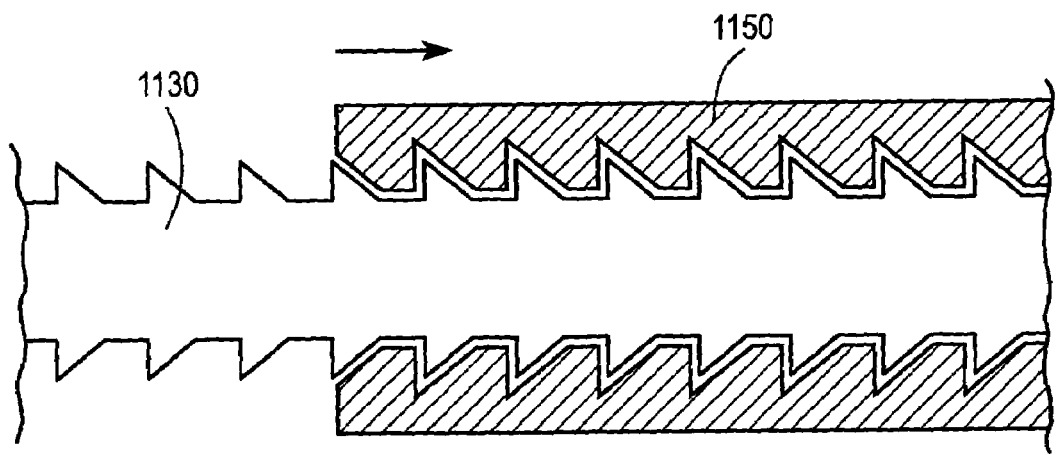
FIG. 11 illustrates one embodiment of a side cross-sectional view of a first lock engaging a second lock.

FIG. 11 illustrates one embodiment of an internal structure of first and second locks 1130, 1150 and the locking mechanics between them. First lock 1130 may have a series of ridges or teeth with a ratchet-like structure (i.e. teeth sloped in one direction only) on its surface that may fit in grooves formed within an inner surface of second lock 1150. Because of the ratchet-like structure of first and second locks 1130, 1150, first lock may move in a direction towards second lock 1150, but may not move in the opposite direction. The first and second locks are one form of an adjustable connector which has an adjustable length. Other embodiments of an adjustable connector include a connector which has a tooth or gear-like protrusion which engages posts on another connector. The posts act as stops preventing disengagement of the tooth once the tooth moves past a post.

Figure 12:
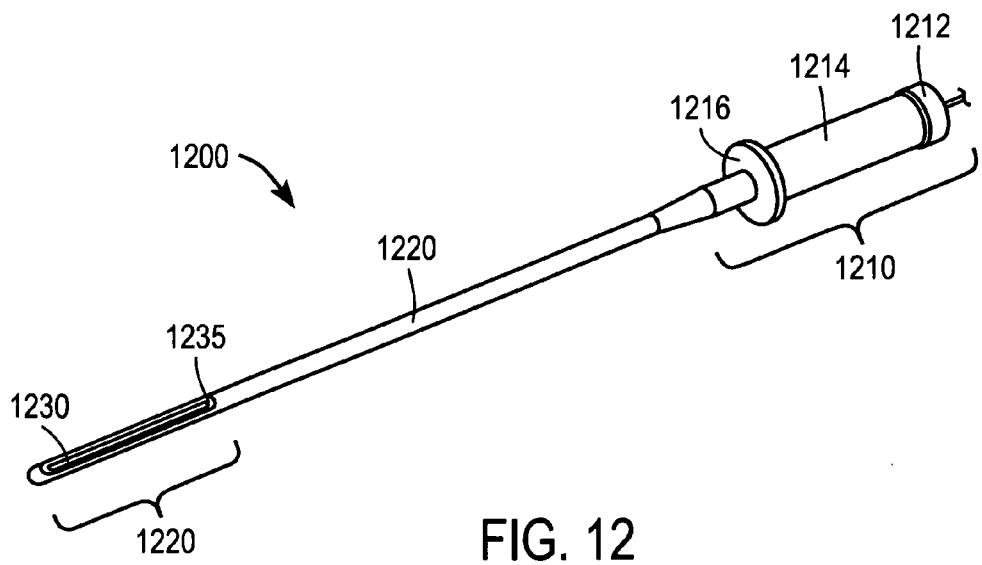
FIG. 12 illustrates one embodiment of a medical device for percutaneous delivery of a heart valve support annulus.

FIG. 12 illustrates one embodiment of a medical device for percutaneous delivery of a heart valve support annulus (e.g., a mitral valve annular ring). The medical device 1200 has a proximal portion 1210 having various control and knob elements for controlling the actions of a distal portion 1220 of medical device 1200. Proximal portion 1210 and distal portion 1220 may be joined by an elongated catheter 1220. A length of catheter portion 1220 may be of any sufficient length to advance to a heart region of patient percutaneously. Proximal portion 1210 includes a deployment button 1212, an attachment knob 1214, and steering knob 1216. Distal portion 1220 includes a slot 1235 by which an annular support 1230 may be released. Distal portion 1220, in one embodiment, is steerable, and further has the capability to form a ring shape (see, for example, FIG. 15A). Distal portion 1220 may be steered by rotating steering knob 1216. Attachment knob 1214 may be used to insert annular support 1230 and guided to the distal portion 1220. Deployment button 1212 may be used to release annular support 1230 from slot 1235. The various methods and mechanics by which annular support 1230 may be deployed from slot 1235 are provided in greater detail below.

Figure 13A:
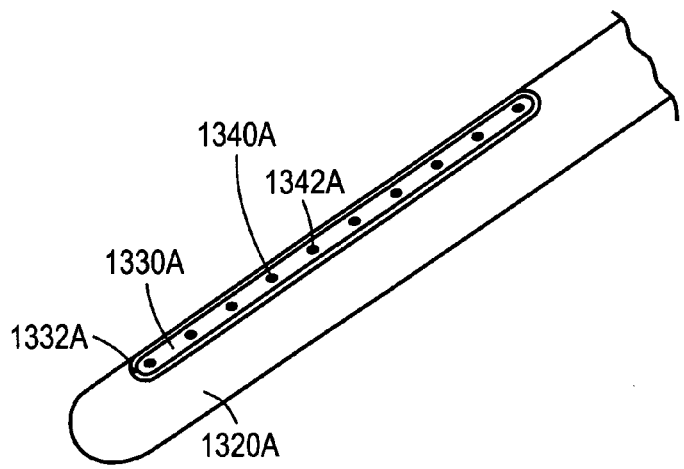
FIGS. 13A-13B illustrate embodiments of a distal portion of a medical device to deliver an annular support to a heart valve.
Figure 13B:
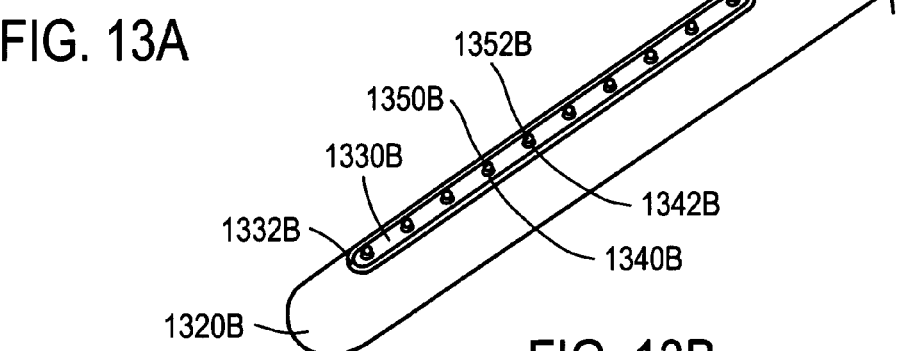

FIGS. 13A-13B illustrate embodiments of a distal portion of a medical device to deliver an annular support to a heart valve (e.g., a mitral valve). In one embodiment, the distal portions shown in FIGS. 13A and 13B may be distal portion 1220 of FIG. 12. FIG. 13A illustrates a support annulus 1330A mounted within an elongated slot 1332A. Support annulus 1330A is shown in a pre-deployment position, being substantially straight. Support annulus also may also have a number of pin holes represented as 1340A, 1342A along a longitudinal length. FIG. 13B illustrates catheter portion 1320B with annular support 1330B mounted within slot 1332B. Pin holes (e.g., 1340B, 1342B) are disposed along annular support 1330. Rivets or pins (represented by 1350B, 1352B) may extend through the pin holes. In one embodiment, rivets 1350B, 1352B may be actuated by a deployment button (e.g., button 1212) disposed near a proximal portion of the medical device. As described in greater detail below, rivets 1350B, 1352 serve to release annular support 1330B from slot 1332B. In one embodiment, distal portion 1320B may be curved or steered into a substantially ring shape, and then released by extending the rivets through the pin holes.

Figure 14:
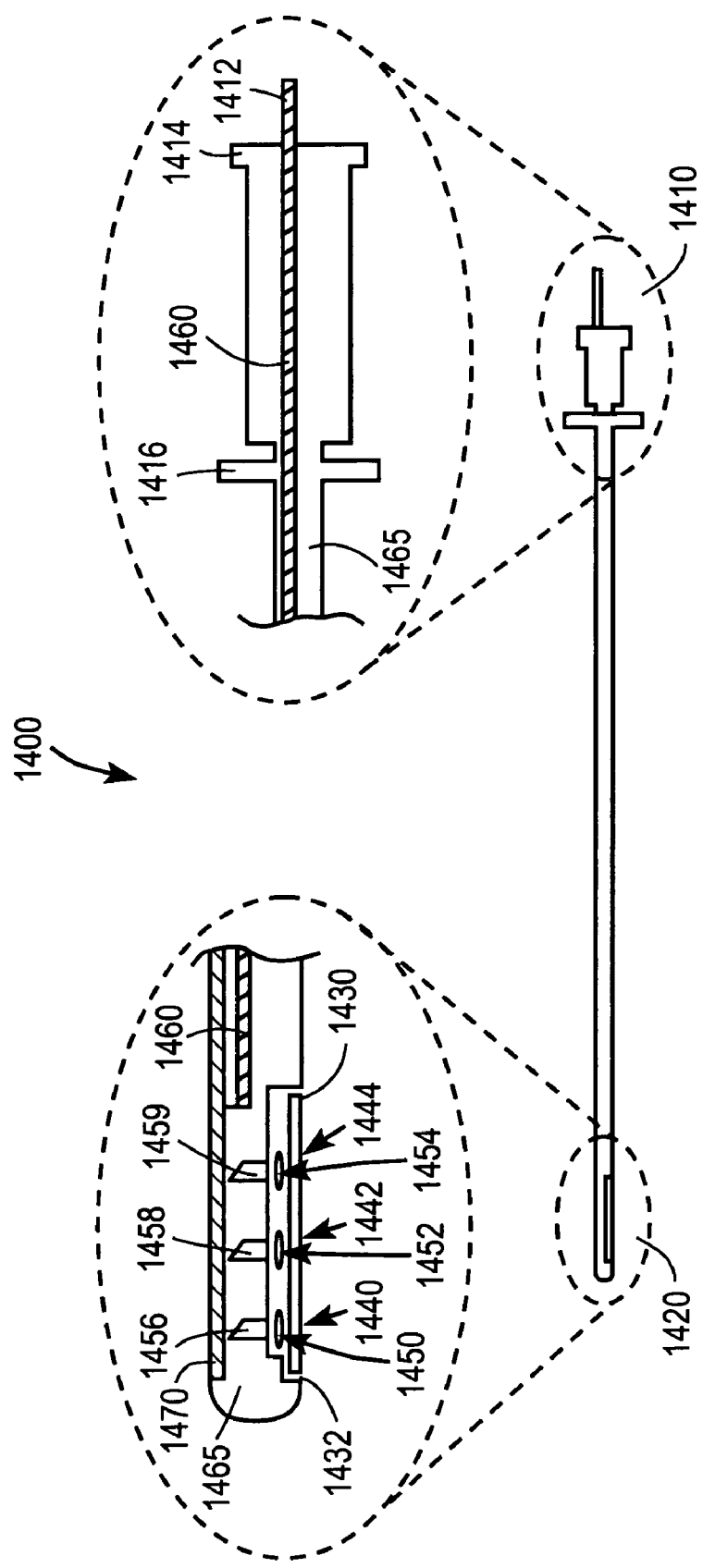
FIG. 14 illustrates a schematic side view of an embodiment of a medical device 1400 that may be used to deliver an annular support to a mitral valve percutaneously.

FIG. 14 illustrates a schematic side view of an embodiment of a medical device 1400 that may be used to deliver an annular support to a mitral valve percutaneously. In one embodiment, the medical device 1400 may be the devices shown in FIGS. 12 and 13A or the devices shown in FIGS. 12 and 13B. Medical device 1400 includes a distal portion 1420 having a size suitable for percutaneous delivery to an atrium and/or a ventricle of a heart. In one embodiment, elongated catheter portion 1420 has a length suitable to advance percutaneously distal portion 1420 to an atrium and/or a ventricle. A proximal portion 1410 of medical device 1400 includes a control mechanism to control various elements of distal portion 1420. An enlarged view of distal portion 1420 is shown as a longitudinal cross-section with annular support 1430 (such as annular supports 1230 or 1330B) mounted within a slot 1432. A lumen 1465 formed within the distal portion 1420 may have one or more rivets (e.g., represented by elements 1450, 1452, and 1454) disposed above holes 1440, 1442, and 1444 of annular support 1430. It will be appreciated that additional holes and rivets may exist on an annular support in order to provide sufficient attachment of the annular support to a mitral valve annulus. The number and position of the rivets depend on the size of the annular support. The holes 1440, 1442, and 1444 are aligned respectively with rivets 1450, 1452, and 1454 as shown in FIG. 14, and the rivets 1450, 1452, and 1454 are aligned respectively with drivers 1456, 1458, and 1459 as shown in FIG. 14. The drivers are used in combination with mandrel 1460, to drive the rivets through the holes in the annular support in order to secure the annular support to a mitral valve annulus. A mandrel 1460 may also be disposed within lumen 1465 of distal portion 1420. Mandrel 1460 may be positioned initially proximal to rivets 1450, 1452, 1454 prior to deployment of support annulus 1430. As described in greater detail below with respect to FIGS. 16A-16B, the advancement of mandrel 1460 towards a distal end of distal portion 1420 pushes the rivets out through holes 1440, 1442, 1444, thereby releasing annular support 1430 from slot 1432 and securing the annular support 1430 to a mitral valve annulus. Mandrel 1460, in one embodiment, may extend all the way back to proximal portion 1410 and be coupled to push button 1412 as shown in FIG. 14.

A lumen 1465 formed within the distal portion 1420 may also have a steering mandrel 1470 disposed along an inner surface. Steering mandrel 1470 may be coupled to steering knob 1416 disposed near the proximal portion 1410 of medical device 1400. Rotating steering knob 1416 may bend or steer mandrel 1470. Mandrel 1470 may be made of a variety of rigid and/or flexible materials used in steerable catheters known in the art. Additional steering mandrels (e.g., 3 disposed at 120° intervals circumferentially around the perimeter of the catheter) may also be used to provide additional control for steering of the distal portion of the catheter of FIG. 14. Proximal portion 1410 may also have an attachment knob 1414 that may be removed to insert and load support annulus 1430, and its corresponding rivets. In one embodiment, medical device 1400 is adapted to be positioned above a mitral valve annulus from the left atrium (by, for example, crossing the septum which separate the atria). When delivered percutaneously, medical device 1400 is provided with sufficient torsional stiffness to allow it to respond in kind at the distal portion 1420 to a torque applied from the proximal portion 1410 of medical device 1400.

Figure 15A:
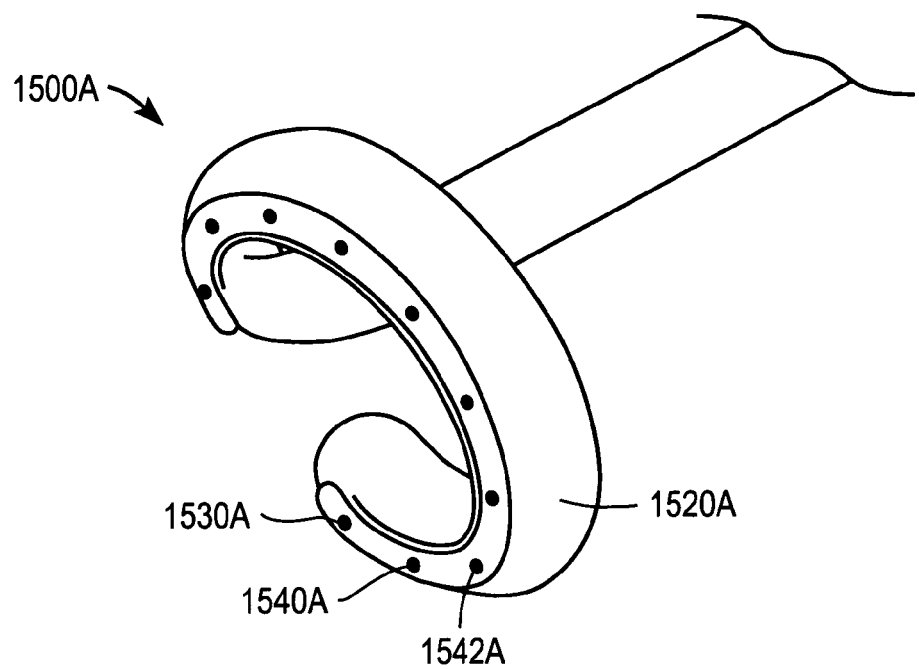
FIGS. 15A-15B illustrate exemplary embodiments of medical devices for releasing an annular support from a distal portion of a steerable catheter.
Figure 15B:
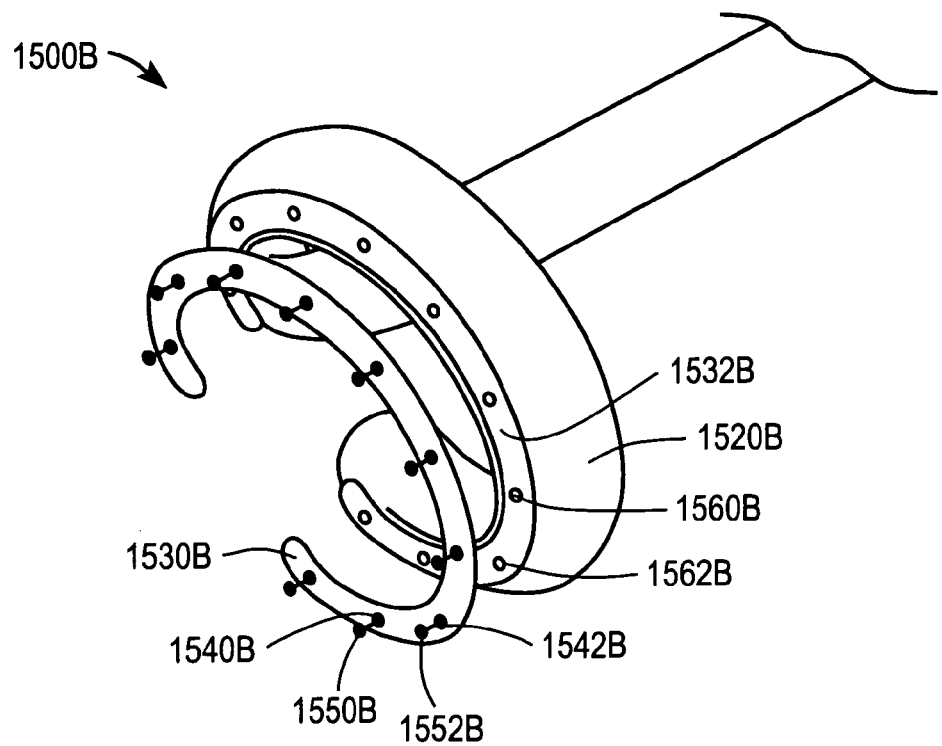

FIGS. 15A-15B illustrate exemplary embodiments of medical devices 1500A, 1500B releasing an annular support from a distal portion of a steerable catheter. In one embodiment, devices 1500A and 1500B may be the devices shown in FIGS. 12 and 13B and 14. FIG. 15A shows distal catheter portion 1520A curved to a substantially circular shape. In one embodiment, a steering knob disposed near proximal portion of the medical device (e.g., steering knob 1216) may be used to curve to the shape shown. As discussed above, a steering mandrel (e.g., 1470) may be disposed within a lumen of distal portion 1520A that is controlled by the steering knob. It may be appreciated by one of skill in the art that distal portion 1520A may be steered to form a variety of shapes, and not limited to the substantially circular shape shown. A support annulus 1530A may be disposed or mounted on a slot (not shown) near distal portion 1520A of medical device 1500A. Support annulus has one or more holes (e.g., 1540A, 1542A) disposed along its length which are used to receive rivets which anchor the support annulus to the mitral valve annulus. Support annulus 1530A may be made of a compliant material that bends and curves according to the shape formed by distal portion 1520A.

FIG. 15B shows distal portion 1520B of medical device 1500 having support annulus 1530B deployed from slot 1532B. In one embodiment, support annulus 1530B may be deployed by extending one or more rivets or pins (e.g., rivets 1550B, 1552B) from holes disposed along slot 1532B (e.g., holes 1560B, 1562B) and through holes disposed on support annulus 1530B (e.g., holes 1540B, 1542B). In one embodiment, rivets 1550B, 1552B may be released as described above with respect to FIG. 14 (and further a shown in FIG. 16 or 17).

Figure 16:
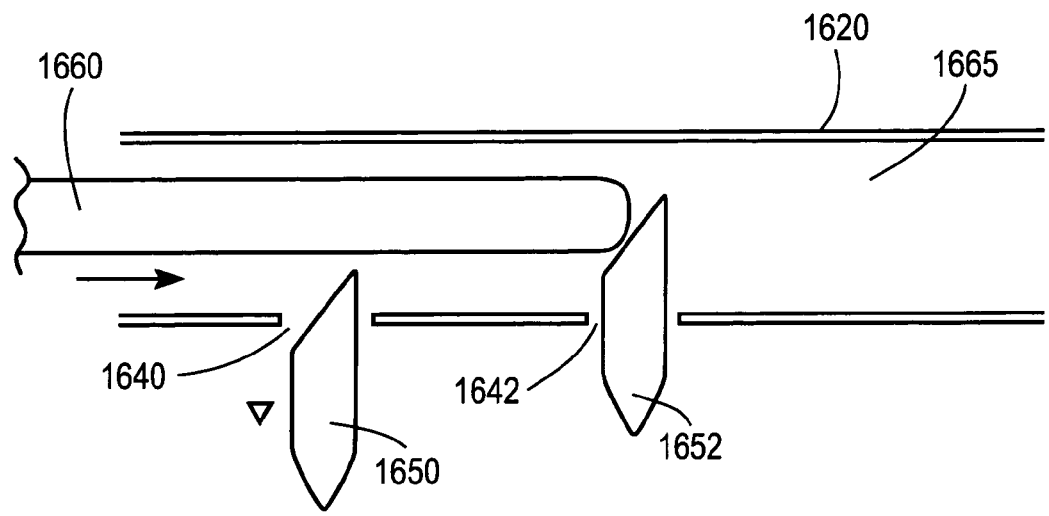
FIG. 16 illustrates one embodiment of a method to deploy rivets from a lumen of a distal portion of a medical device catheter.

FIG. 16 illustrates one embodiment of a method to deploy rivets from a lumen of a distal portion of a medical device catheter (e.g., to deploy a support annulus as described above). Catheter 1620 forms a lumen 1665 having one or more rivets (e.g., 1650, 1652) disposed therein. The rivets may be positioned and aligned over opening or holes (e.g., holes 1640, 1642) in the side of the catheters 620. By advancing a push-rod or mandrel 1660 (such as the mandrel 1460) in the direction of the arrow as indicated, the sloped surface of each rivet that contacts mandrel 1660 drives the rivet through a corresponding hole in the catheter and through a hole (not shown in FIG. 16 but shown in FIG. 14) in the annular support which is being deployed. As illustrated, rivet 1650 has been released through hole 1640, and rivet 1652 is shown just prior to contacting mandrel 1660. In one embodiment, mandrel 1660 may be actuated by a push button (e.g., push button 1412 disposed near a proximal portion of the medical device. In one embodiment, the push button may be part of a control mechanism handle that controls other elements of the distal portion. The rivet may have a larger head which includes the sloped surface, where the head exceeds the size of the hole in the annulus support which is designated to receive the rivet. In the view of FIG. 14, a group of drivers have a sloped surface and are used to drive the corresponding rivets through the holes of the annular support 1430 as shown in FIG. 16. In the case of FIG. 16, the rivets are driven from the mandrel without a group of drivers.

Figure 17:
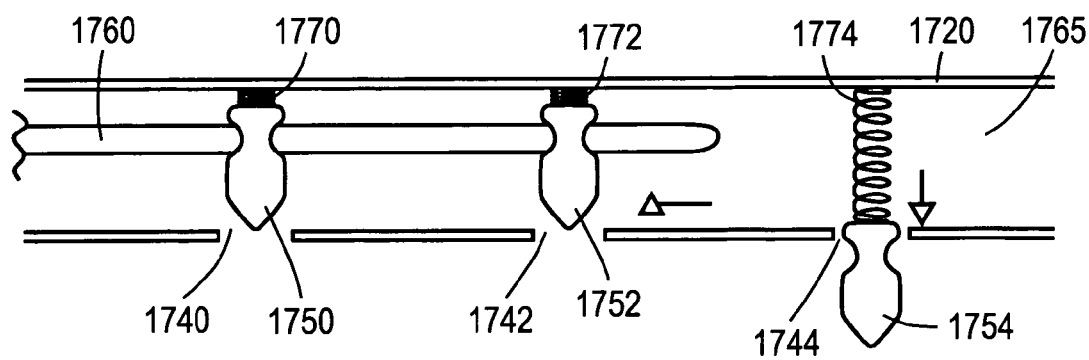
FIG. 17 illustrates an alternative embodiment for driving rivets through an opening of a catheter and through a support annulus.

FIG. 17 illustrates an alternative embodiment for driving rivets through openings of a catheter and through holes in a support annulus. A lumen 1765 formed by catheter 1720 has disposed within it one or more rivets (e.g., rivets 1750, 1752, 1754) and held in place by a mandrel passing through an opening within each rivet. Each rivet may be positioned over an opening or hole formed on catheter 1720 (e.g., holes 1740, 1742, 1744). A compressed spring (e.g., springs 1770, 1772, 1774) provides the driving force to release a rivet when mandrel 1760 is pulled out or removed from a particular rivet (as shown by rivet 1754).

Figure 18:
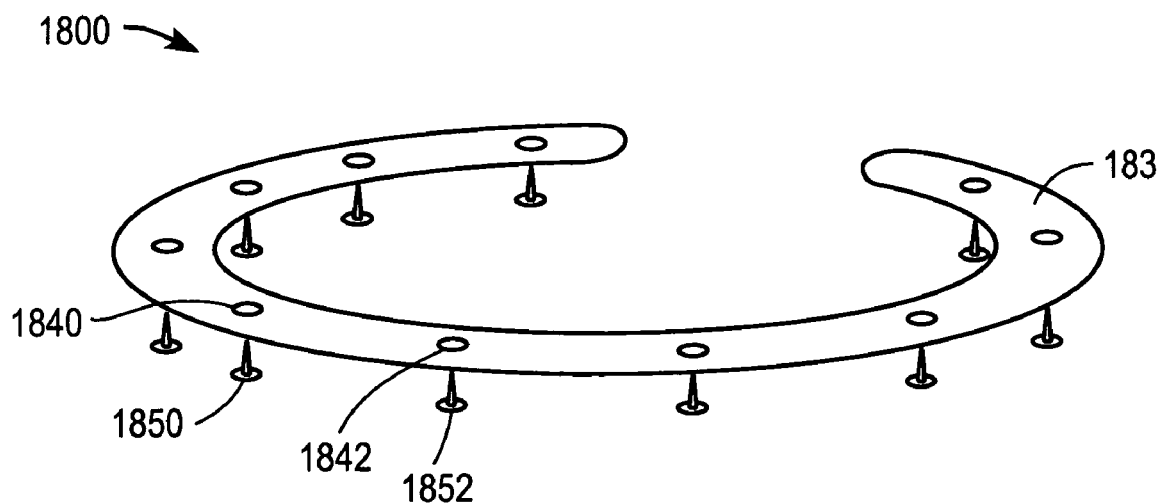
FIG. 18 illustrates one embodiment of a support annulus having a substantially circular shape to conform to a shape of a heart valve such as a mitral valve.

FIG. 18 illustrates one embodiment of a support annulus 1800 having a substantially circular shape to conform to a shape of a heart valve such as a mitral valve. The support annulus 1800 may be any one of the annular supports shown in FIGS. 12, 13A, 13B, 14, 15A and 15B, and these annular supports have a size and a radius of curvature which is designed to reshape the mitral valve to reduce or eliminate mitral valve regurgitation. Support annulus has one or more holes (e.g., holes 1840, 1842) to receive one or more rivets (e.g., 1850, 1852). Support annulus 1800 may be deployed from a distal portion of a catheter as described above, utilizing the rivets to secure the support annulus to the valve tissue.

Figure 19A:
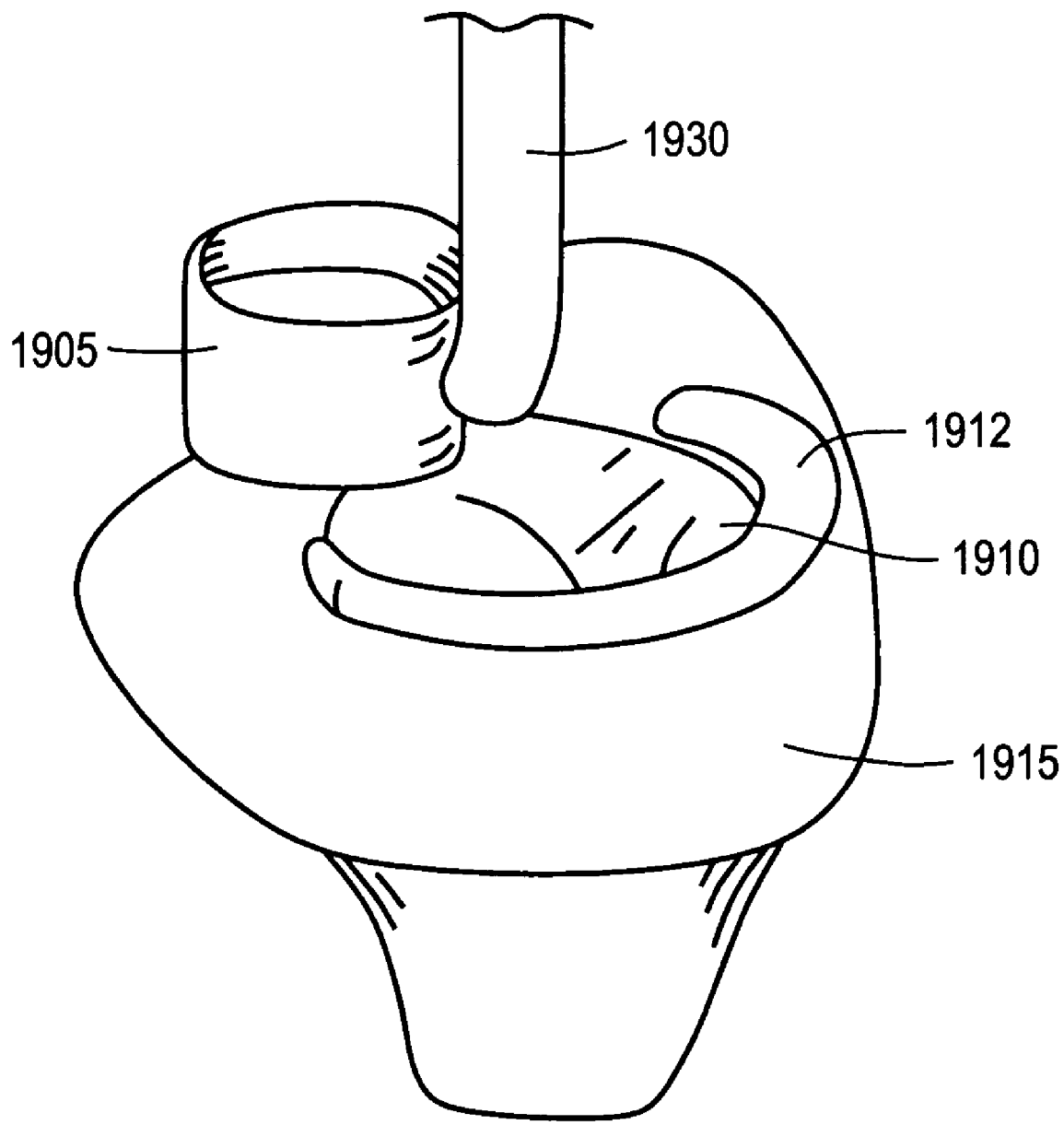
FIGS. 19A-19C illustrate an exemplary method of delivering a support annulus to a mitral valve from an atrium side of the heart.
Figure 19B:
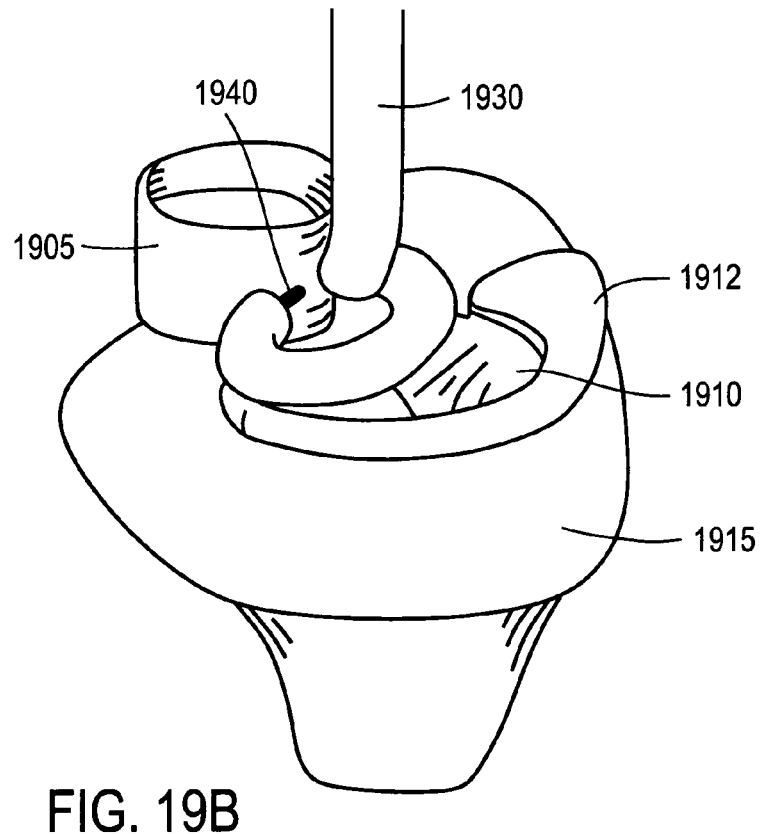
Figure 19C:
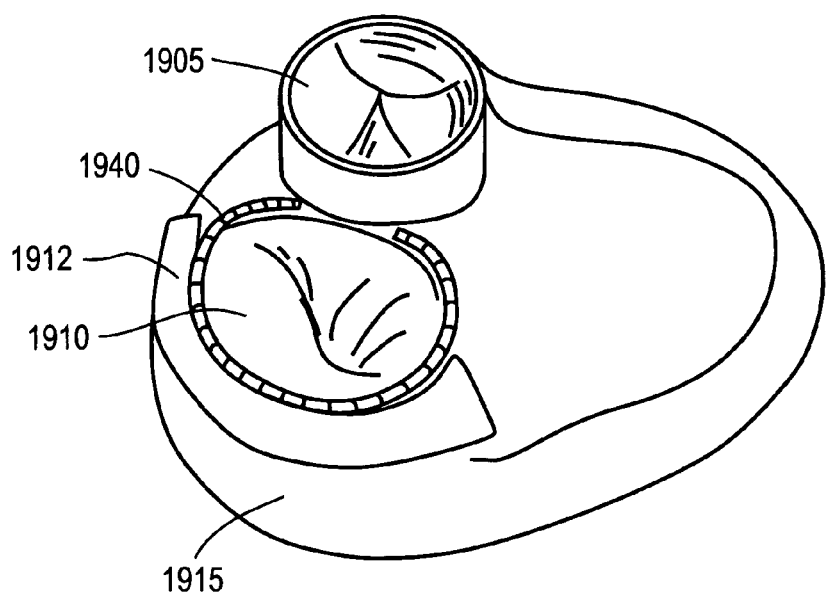

FIGS. 19A-19C illustrate an exemplary method of delivering a support annulus to a mitral valve from an atrium side of the heart. In one embodiment, the support annulus may be delivered percutaneously with a medical device 1400 described above. FIG. 19A shows a simplified representation of a heart with aortic valve 1905, mitral valve 1910, and left ventricle 1915. An annular portion 1912 surrounds mitral valve 1910 as viewed down the left atrium. A distal portion of a percutaneously advanced catheter 1930 is positioned over mitral valve 1910. Catheter 1930 may be advanced percutaneously to the mitral valve by first passing a guide wire (not shown) to the mitral valve region. The guidewire may be advanced in an antegrade manner to the mitral valve region percutaneously, entering, for example, through the femoral vein to the right atrium, and puncturing through the septum between the right and left atria and then entering into the left atrium and passing through and across the mitral valve. An obturator may also be used (similar to those used in the current practice of balloon valvioplasty). Percutaneous methods for advancing a guidewire to the mitral valve region and accessing the left atrium through the septum are known in the art; accordingly, a detailed description is not provided. Various imaging techniques known in the art may also be used to locate the mitral valve leaflets. For example, echo imaging, infrared illumination, x-ray, and magnetic resonance imaging methods may be utilized. These imaging techniques are known in the art; accordingly, a detailed description is not provided. Catheter 1930 is placed over the guide wire and into the body through an introducer (a known device in the art) in a vein. A guide catheter (not shown) may first be placed over the guide wire and advanced through the introducer into a vessel lumen. The guide catheter may also contain its own guide wire component to provide the catheter with the ability to steer its way to the target location. As an alternative to an over-the-wire catheter, a rapid exchange catheter delivery system may be utilized. As such, the catheter may be any of the catheter types used in the art, including but not limited to "rapid exchange" (RX) catheters, "over-the-wire" (OTW) catheters, or a "tip RX" catheters. The guide wire and guide catheter may be advanced through the vein to the vena cava and into the right atrium of the heart.

FIG. 19B illustrates distal portion of catheter 1930 curved to a substantially circular shape to conform to the circular shape of annular portion 1912 of mitral valve 1910. In certain embodiments, the portion of catheter 1930 may be the portions 1220 or 1420 of the catheters shown in FIGS. 12 and 14 respectively. Once positioned in a substantially circular shape over mitral valve 1910, catheter 1930 may release annular support 1940 (such as annular supports 1230 or 1430) for attachment to annular portion 1910. Annular support 1940 may, in one embodiment, be released as described above with respect to FIGS. 15A-15B, using rivets described with respect to FIGS. 16 and 17. FIG. 19C illustrates annular support 1940 secured to annular portion 1912 of mitral valve 1910. Once deployed, annular support 1940 may provide the benefits of improving mitral valve function, including the closing of valve cusps during contraction (e.g., systole) or correcting problems such as prolapse.

Figure 20A:
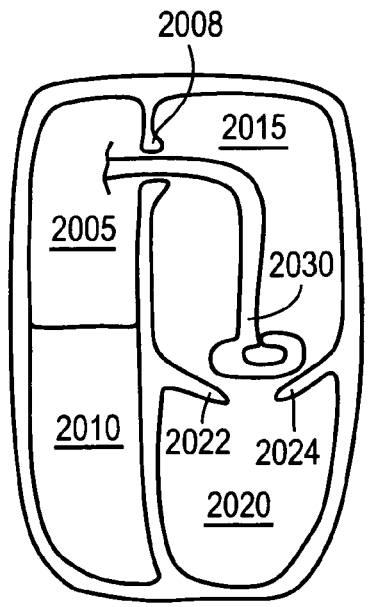
FIGS. 20A-20D illustrate one exemplary method for deploying a dual support annulus.
Figure 20B:
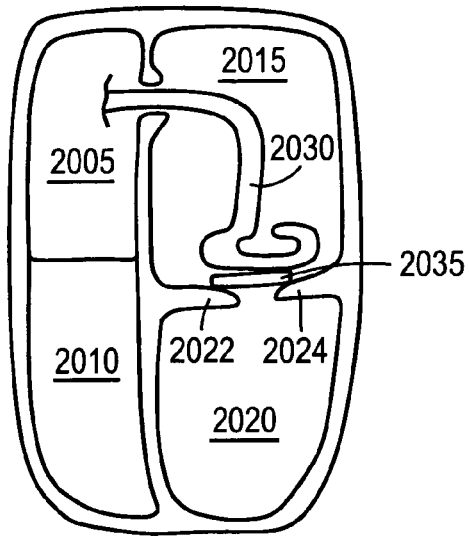
Figure 20C:
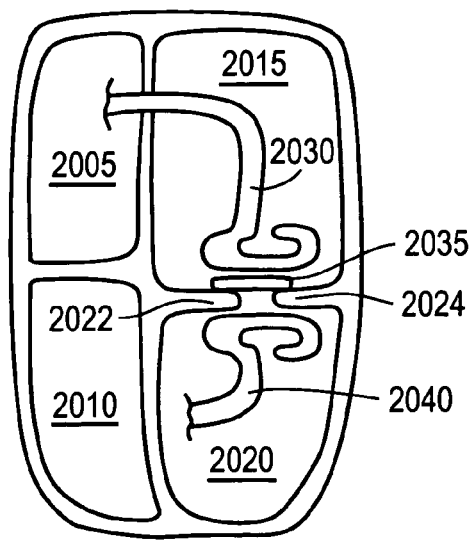
Figure 20D:
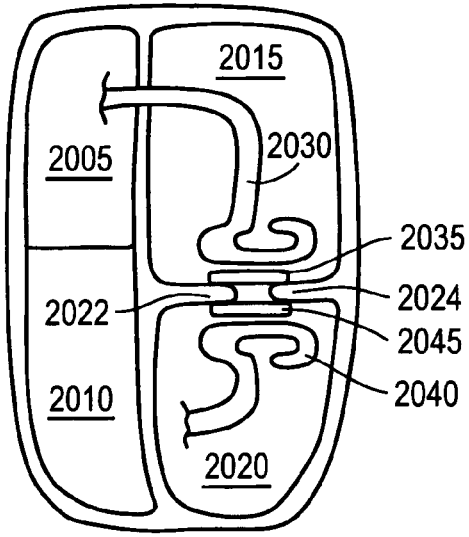
Figure 22:
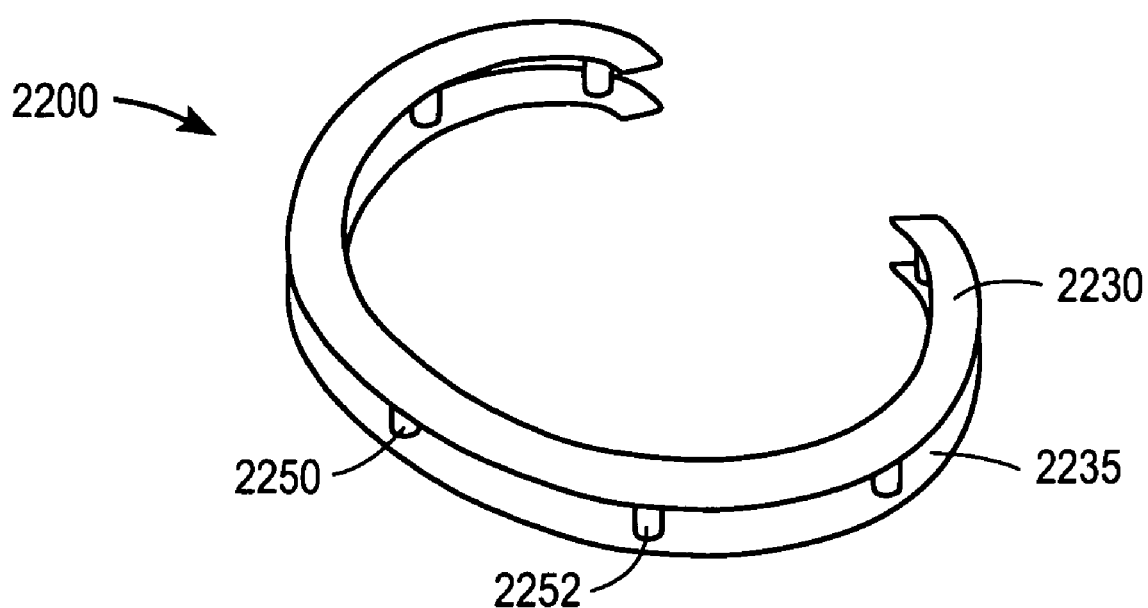
FIG. 22 illustrates an alternative embodiment of a support annulus for deployment over a heart valve.

FIG. 22 illustrates an alternative embodiment of a support annulus for deployment over a heart valve. Support annulus 2200 may have a dual support structure including a first support annulus 2230 and a second support annulus 2235 aligned below first support annulus 2230. First and second support annulus 2230, 2235 may be secured or coupled to each other with one or more rivets (e.g., rivets 2250, 2252). In one embodiment, the first support annulus 2230 is deployed or positioned on the atrium side of the mitral valve and the second support annulus 2235 is deployed on the ventricle side of the mitral valve. Rivets 2250, 2252 may be comparable to those described above with respect to FIG. 18, and may be deployed from a distal portion of a catheter as described with respect to FIGS. 16 and 17. FIGS. 20A-20D illustrate one exemplary method for deploying the dual support annulus 2200 of FIG. 22. FIG. 20A shows a simplified representation of a heart with chambers right atrium 2005, right ventricle 2010, left atrium 2015, and left ventricle 2020. A distal portion 2030 of a medical device (e.g., medical device 1400) that is percutaneously advanced to the left atrium (through the right atrium and then through the septum) is shown. The distal portion 2030 is advanced in an antegrade manner to the mitral valve region percutaneously, entering, for example, through the femoral vein (for example) to the right atrium 2005, and puncturing through the septum 2008 between the right and left atria and then entering into the left atrium 2015 and positioned above the mitral valve leaflets 2022, 2024. Distal portion 2030 may then be conformed to a substantially circular shape (as shown), such as the distal portions shown in FIGS. 15A and 15B. Next, as illustrated by FIG. 20B, first support annulus 2035 may be released from distal portion 2030 and secured to the mitral annulus on the atrium side of the mitral valve. In one embodiment, first support annulus 2035 is released using a pop rivet method described above with respect to FIG. 16 or 17. Next, as illustrated by FIG. 20C, a second catheter distal portion 2040 (for example, a device similar to device 1400 in FIG. 14) is advanced percutaneously to the left ventricle, positioning itself opposite the first support annulus 2035 disposed on the atrium side of the mitral valve leaflets 2022, 2024. Second catheter distal portion 2040 may be advanced to left ventricle 2020 from the aortic arch (not shown) extending from left ventricle 2020. Next, as illustrated by FIG. 20D, a second catheter distal portion 2040 may release and secure a second support annulus 2045 to align with first support annulus 2035. In an alternative embodiment, second support annulus 2045, or the support member disposed on the left ventricle side of the mitral valve may be delivered prior to delivery of the support annulus disposed on the left atrium side of the mitral valve. In another alternative embodiment, catheter portions 2030 and 2040 may be positioned simultaneously on the left atrium and left ventricles sides of the mitral valve such that first support annulus 2035 and second support annulus 2045 may be released about at the same time. In this manner, one or more rivets released from either catheter 2030 or 2040 may pass through the mitral valve to the opposite support annulus and secured therein.

Figure 21:
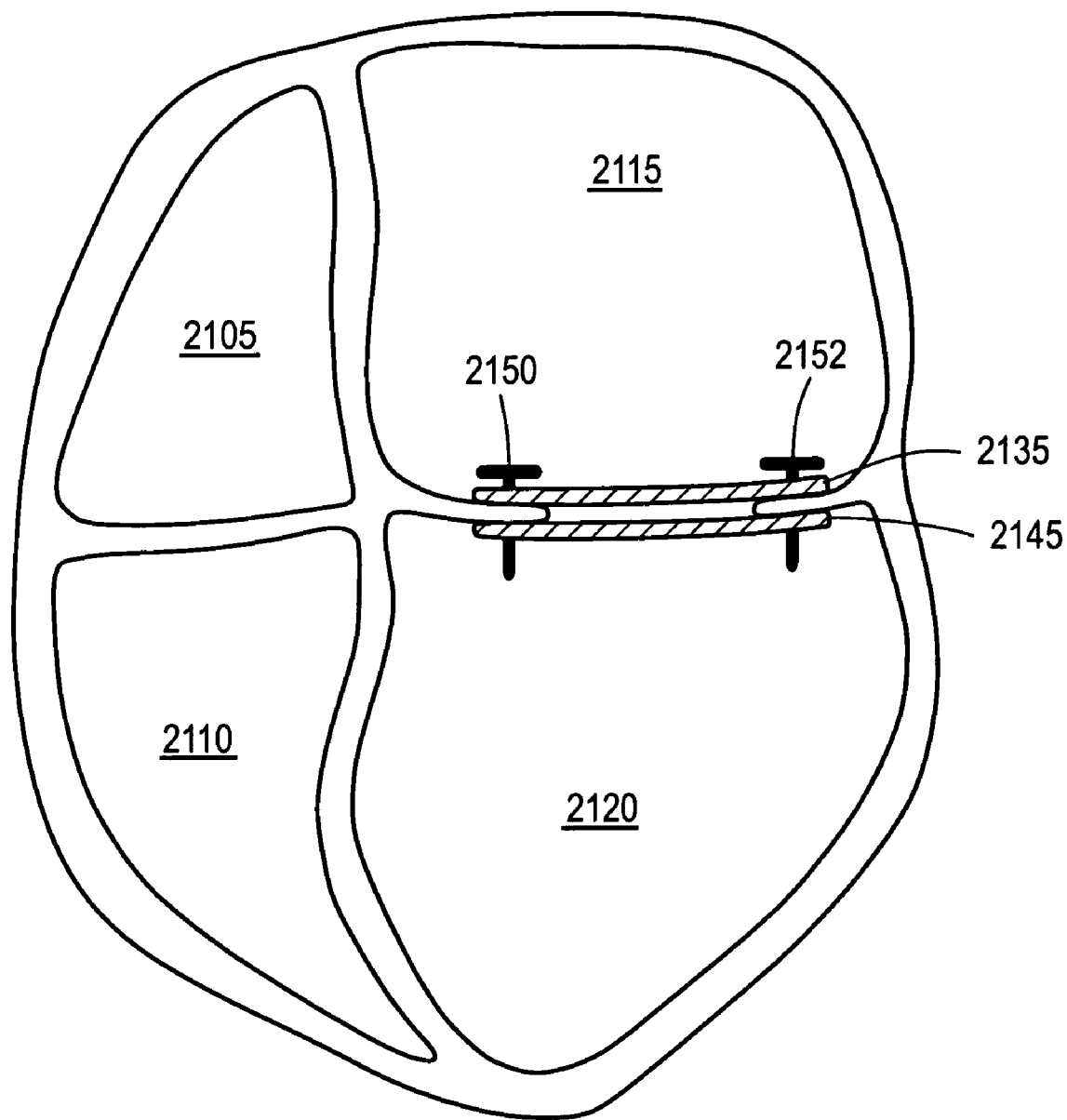
FIG. 21 illustrates another embodiment of a support annulus having a first support annulus and a second support annulus.

FIG. 21 illustrates another embodiment of a support annulus having a first support annulus 2135 disposed on the left atrium 2115 side of the mitral valve and a second support annulus 2145 disposed on the left ventricle side 2120 of the mitral valve. One or more rivets 2150, 2152 may be used to secure first and second support annulus 2135, 2145 to each other and with the mitral valve tissue. Alternatively, one set of rivets may secure the first support annulus and another set of rivets may secure the second support annulus. The use of a dual support annulus as described and shown with respect to FIGS. 20A-20D, 21, and 22 may provide greater support to the mitral valve annulus compared to the single support annulus (e.g., support annulus 1800 of FIG. 18).

Figure 23B:
FIGS. 23A-23B illustrate another embodiment of a support annulus for placement near the annulus of a heart valve.
Figure 23A:
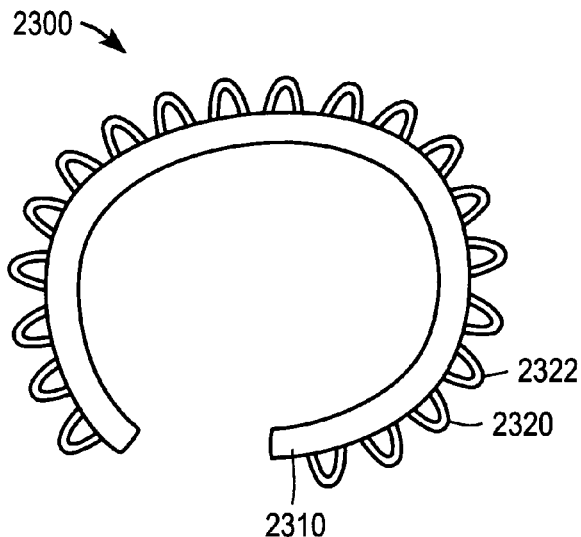

FIG. 23A illustrates another embodiment of a support annulus for placement near the annulus of a heart valve, for example, the mitral valve. As with the other embodiment discussed herein, support annulus 2300 may be delivered percutaneously. Support annulus 2300, in one embodiment, may have a deformable body portion 2310 (e.g., may be flexed to a substantially circular or ring shape) and one or more support struts (e.g., 2320, 2322) disposed around a circumference of body portion 2310. Support struts 2320, 2322 may be shaped as half-loops such that they serve to attach the support annulus to the mitral valve annulus. Support struts 2320, 2322 may be substantially rigid to provide support when placed on the mitral valve, but also having deformable properties to fit inside a guiding catheter. In one embodiment, body portion 2310 and support struts 2320, 2322 may be made of a shape memory material such as nickel titanium. In another embodiment, body portion 2310 and support struts 2320, 2322 may be made a biocompatible material having rigid properties. FIG. 23B illustrates a side view of support annulus 2300 with body portion 2310 having support struts (e.g. 2320, 2322) disposed around an outer circumference of body portion 2310. The number of support struts that may be disposed around body portion 2310 is variable, and as such support annulus 2300 may be designed to have any number of support struts depending on the size of body portion 2310 and the amount of support desired for the mitral valve. In one embodiment, the support struts may be biased toward the bottom of the support annulus so that they may protrude out from a distal portion of a catheter (e.g., catheter 2430 discussed below). As described in greater detail below, support annulus 2300 may be secured to a valve annulus with clips disposed through the support struts. A separate clipping device or catheter may be utilized to attach support annulus 2300 to the valve annulus.

Figure 24A:
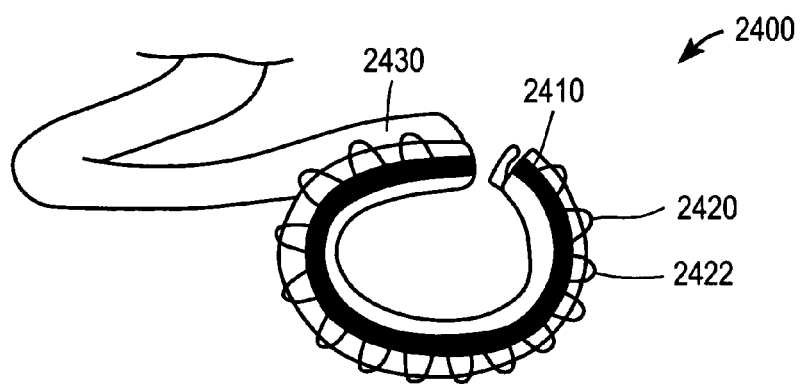
FIG. 24A illustrates a bottom view of a catheter with support annulus that has been disposed near the distal end.
Figure 24B:
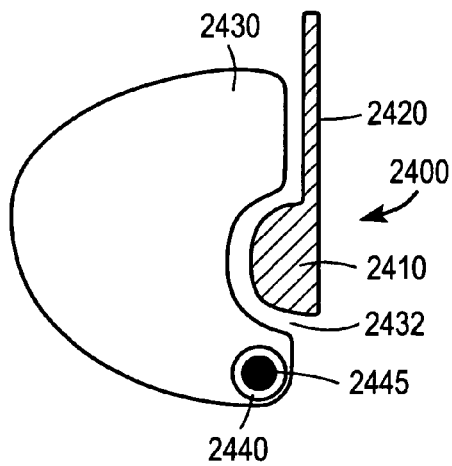
FIG. 24B illustrates a cross-sectional view of a distal portion of a catheter having support annulus disposed within a slot formed within the catheter.

FIG. 24A illustrates a bottom view of a catheter 2430 with support annulus 2400 that has been disposed near the distal end (e.g., by advancing support annulus 2400 through catheter 2430 to a distal end). The catheter 2430 may, in one embodiments resemble catheter 1400 of FIG. 14 but catheter 2430 includes additional features, described below, which are not part of catheter 1400 of FIG. 14. The distal portion of catheter 2430 may have an elongated slot or elongated opening to release support annulus 2400 from catheter 2430. In one embodiment, catheter 2430 may be part of an elongated medical device (e.g., medical device 1400 discussed above) having a control mechanism or handle disposed near a proximal portion. FIG. 24B illustrates a cross-sectional view of a distal portion of catheter 2430 having support annulus 2400 disposed within a slot 2432 formed within catheter 2430. Support annulus 2400 has body portion 2410 with a support strut 2420 extending from body portion 2410 past an outer diameter of catheter 2430. Catheter 2430 also forms a lumen 2440 in which a steering rod or tendon 2445 may be disposed therein. Steering tendon 2445 enables the distal portion of catheter 2430 to form a substantially circular shape when positioned over a mitral valve. In one embodiment, the support annulus 2400 may be the support annulus 2300.

Figure 25:
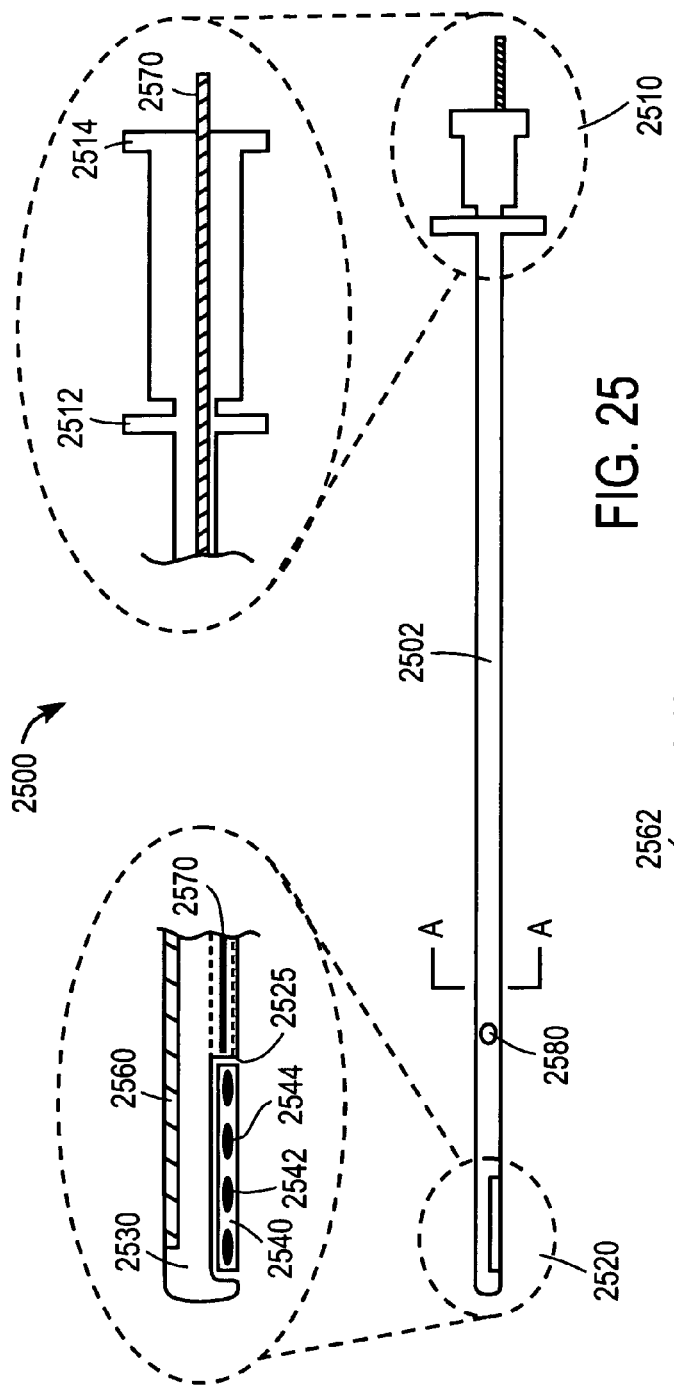
FIG. 25 illustrates a schematic side view of an embodiment of a medical device that may be used to deliver an annular support to a mitral valve percutaneously.

FIG. 25 illustrates a schematic side view of an embodiment of a medical device 2500 that may be used to deliver an annular support to a mitral valve (e.g., annular support 2300) percutaneously. Medical device 2500 includes a distal portion 2520 having a size suitable for percutaneous delivery to an atrium and/or a ventricle of a heart. In one embodiment, elongated catheter portion 2502 has a length suitable to advance distal portion 2520 to an atrium and/or a ventricle. A proximal portion 2510 of medical device 2500 includes a control mechanism or handle to control various elements of distal portion 2520. An enlarged view of distal portion 2520 is shown as a longitudinal cross-section with annular support 2540 mounted or advanced to a slot 2525. Annular support 2540, which in one embodiment may be annular support 2300 of FIG. 23A, has one or more support struts (e.g., 2542, 2544), such as struts 2320 and 2322, disposed along an edge. A mandrel or steering tendon 2560 may also be disposed within medical device 2500 and extending to distal portion 2520 from proximal portion 2510. Steering knob 2512 may be coupled to the steering tendon 2560 and enables distal portion 2520 to be steered and/curved to a desired shape, for example, to a substantially circular shape when positioned over the mitral valve annulus. A push rod or mandrel 2570 may also be disposed within medical device 2500. Mandrel 2570 may be used to advance support annulus 2540 when loaded from the proximal portion 2510 of medical device 2500. Elongated catheter portion also includes an opening 2580 formed proximal to slot 2525. As described in greater detail below, a separate catheter or attaching device may be extended from opening 2580 to clip or secure support struts 2542, 2544 to the mitral valve annulus.

Figure 25A:
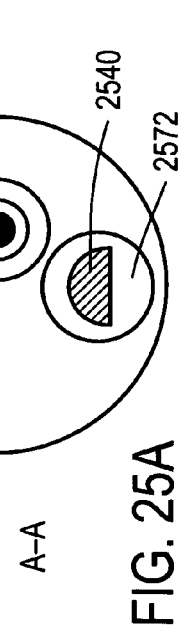
FIG. 25A illustrates a cross-sectional view of medical device taken along line A-A.

FIG. 25A illustrates a cross-sectional view of medical device 2500 taken along line A-A. One or more lumens are formed within catheter portion 2502 including lumen 2562 that has steering tendon/rod 2560 disposed therein. Lumen 2572 may be used to advance support annulus 2540 from proximal portion 2510 to slot 2525 near distal portion 2520. Elongated catheter 2502 may also have lumen 2585 in which an attachment or clipping device/catheter 2590 may be advanced therein. Lumen 2585 extends to opening 2580.

Proximal portion 2510 may have one or more control/steering knobs coupled to parts of distal portion 2520. For example, steering knob 2512 may be coupled to steering tendon 2560 to shape or flex distal catheter portion 2530. A second control knob 2514 may be used to control or guide a clipping device (e.g., represented by 2590 in the cross-sectional view). Additionally, a push rod or mandrel may extend from proximal portion 2510 to guide/advance support annulus to slot 2525 of distal portion 2520.

Figure 26A:
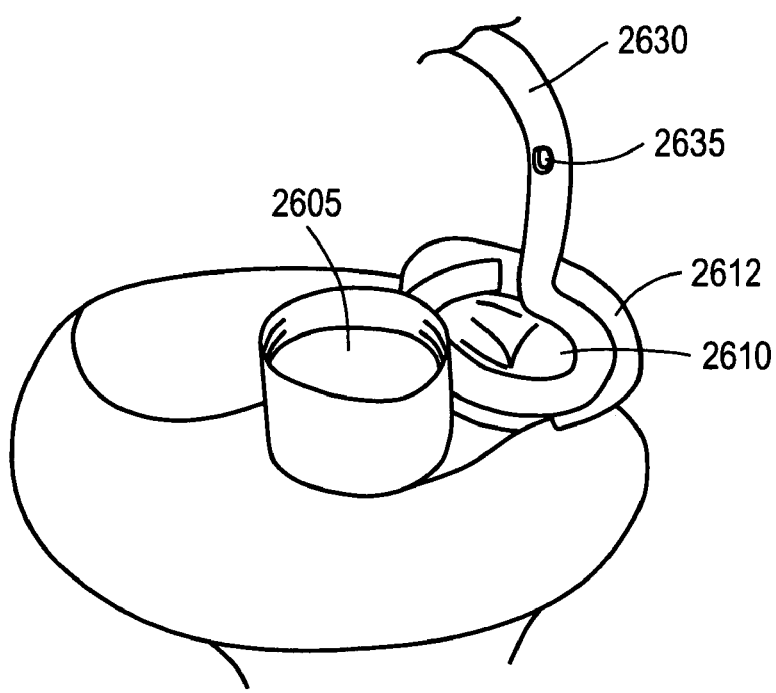
FIGS. 26A-26D illustrate an exemplary method of delivering a support annulus to a mitral valve from the left atrium side of the heart.

FIGS. 26A-26D illustrate an exemplary method of delivering a support annulus (e.g., support annulus 2300 or support annulus 2540) to a mitral valve from the left atrium side of the heart. In one embodiment, the support annulus may be delivered percutaneously with medical device 2500 described above. FIG. 26A shows a simplified representation of a heart with aortic valve 2605, mitral valve 2610, and mitral valve annulus 2612. A distal portion of a percutaneously advanced catheter 2630, which in one embodiment may be the medical device 2500 shown in FIG. 25, is positioned over mitral valve 2610. The distal portion is steered to form a substantially circular shape over mitral valve annulus 2612. Catheter portion 2630 also has hole or opening 2635 (e.g., opening 2580 in FIG. 25) disposed in a substantially straight portion over the circular distal portion. Catheter 2630 may be advanced percutaneously to mitral valve 2610 by first passing a guide wire (not shown) to the mitral valve region. The guidewire may be advanced in an antegrade manner to the mitral valve region percutaneously, entering, for example, through the femoral vein to the right atrium, and puncturing through the septum between the right and left atria and then entering into the left atrium and passing through and across the mitral valve.

Figure 26B:
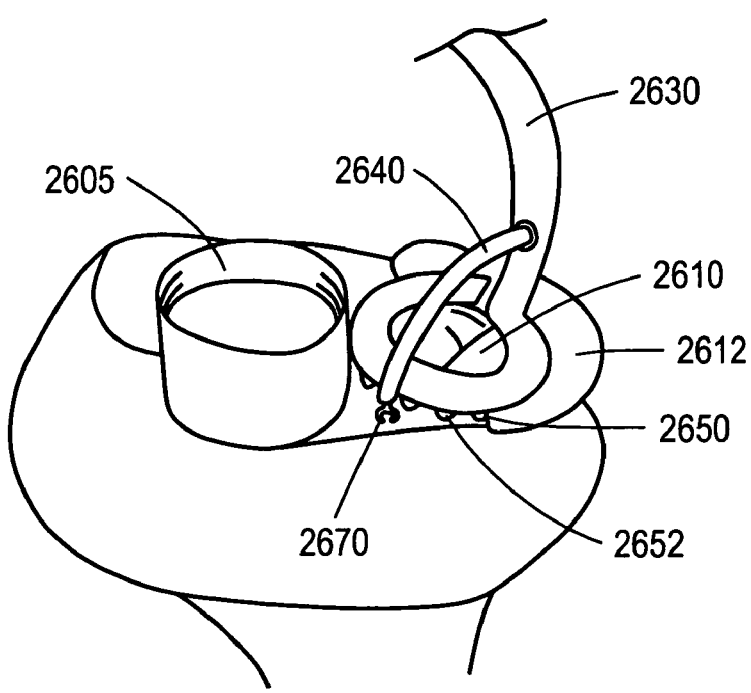
Figure 26C:
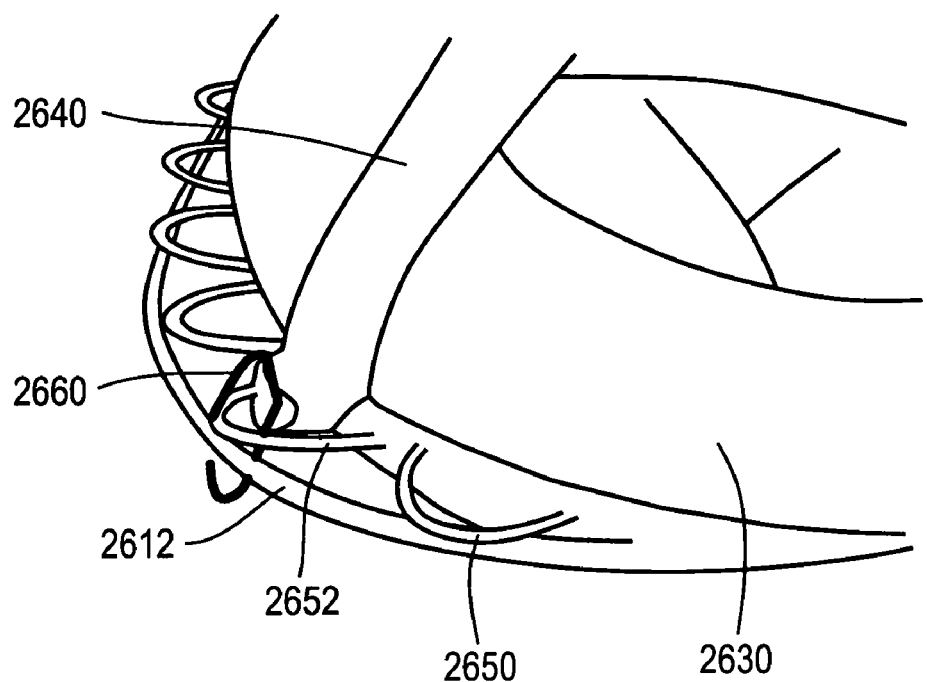
Figure 26D:
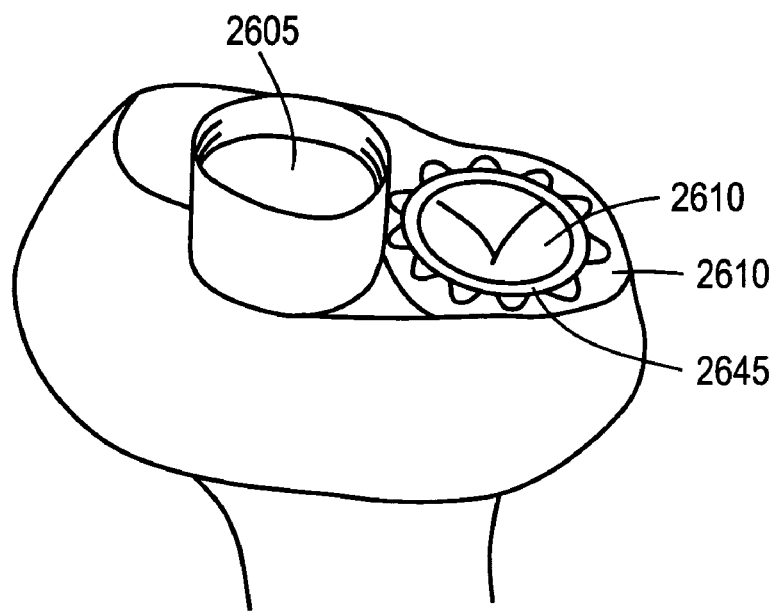

Next, as illustrated by FIG. 26B, an attachment device or catheter 2640 may be extended from opening 2635 to each of the support struts (e.g., 2650, 2652) near the distal portion of catheter 2630. Attachment device 2640 may be used to clip each of the support struts to the tissue of the mitral valve annulus 2612. FIG. 26C illustrates an enlarged view a distal portion of catheter 2630 positioned near mitral valve annulus 2612. Support struts (e.g., strut 2652) is shown being attached to valve annulus 2612 with clip 2660 extending from device 2640. As discussed above, device 2640 extends from opening 2635 of catheter 2630. Clip 2660, having a c-shape in one embodiment, loops from an inner portion of support strut 2652 to an outer portion. The ends of clip 2660 penetrate through the annular tissue and lock with each other. In one embodiment, the mechanism by which clip 2660 attaches may be comparable to that described above with respect to FIGS. 5A-5D. For example, clip 2660 may be self-expanding when extended from device 2640, and the ends of clip 2660 pressed towards each other by advancing a sheath formed by device 2640. Device 2640 may be used to clip each support strut extending from the distal portion of catheter 2630. FIG. 26D illustrates support annulus 2645 deployed and secured over mitral valve 2610. The support struts extending from an outer circumference of support annulus 2645 have been secured to the valve annulus with the clipping method described above. The support annulus 2645, in one embodiment, has a size and shape (e.g., curvature), which is designed to reshape the mitral valve in order to reduce mitral valve regurgitation.

Figure 27:
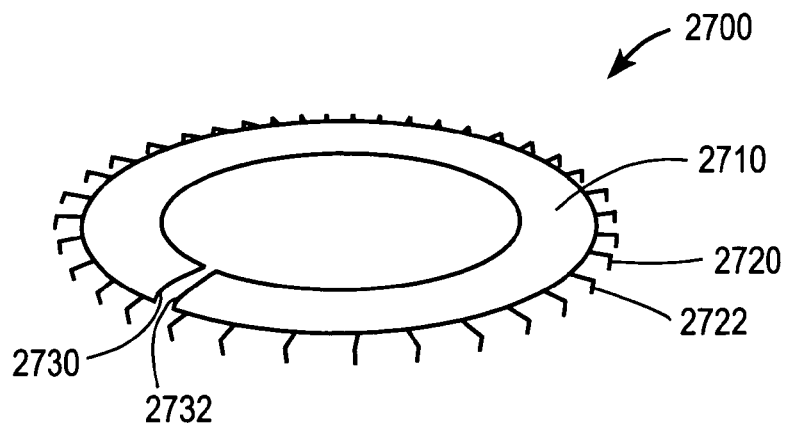
FIG. 27 illustrates another embodiment of a support annulus sized to be suitable to modify a heart valve.

FIG. 27 illustrates another embodiment of a support annulus sized to be suitable to modify a heart valve, such as to improve the closing of the valve. Support annulus 2700 includes body portion 2710 and one or more hooks (e.g., hooks 2720, 2722) disposed around an outer circumference of body 2710 to assist in anchoring support annulus 2700 to an atrium wall or an valve annulus. In one embodiment, support annulus 2700 may have a tubular structure having first end 2730 and second end 2732. First end 2730 and second end 2732 may be connected to define the annular shape. Support annulus 2700 has a dimension suitable, in one embodiment, for being seated in a heart valve annulus, such as a mitral valve annulus. Representatively, support annulus 2700 may have a diameter on the order of 19 to 31 mm. In one embodiment, support annulus 2700 is made of a material suitable to stabilize the size and geometry of the mitral valve annulus to inhibit progressive valvular degradation, and to provide a stable platform on which to attach to the valve annulus. In one embodiment, a representative diameter is on the order of 19 to 31 centimeters.

Figure 28A:
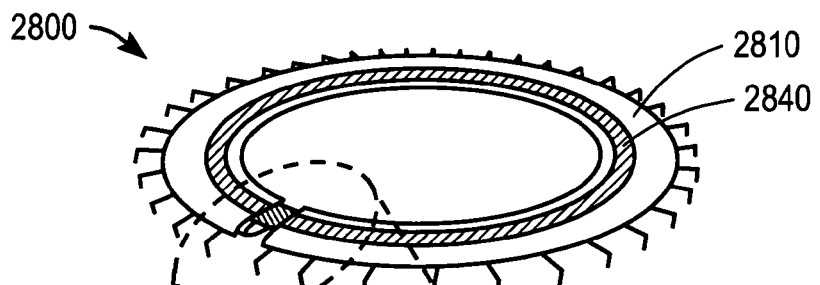
FIGS. 28A-28B illustrate another view of a support annulus.
Figure 28B:
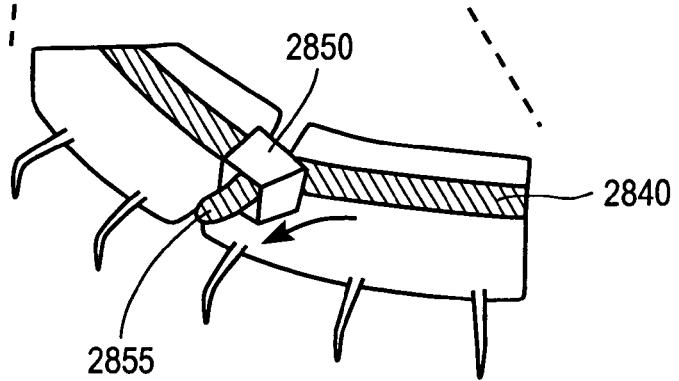

FIGS. 28A and 28B illustrate another view of a support annulus (e.g., support annulus 2700), specifically a top, perspective cross-sectional view. From this view, support annulus 2800 is shown as a tubular structure including inner body 2840. Inner body 2840 includes housing 2850 at one end and second end 2855, designed to be connected to one another to define an annular body within support annulus 2800. In one embodiment, a diameter of inner body 2840 may be adjustable. The connection between housing 2850 and second end 2855 may be a zip tie (e.g., cable tie-like) lock fitting. The fitting of second end 2855 with housing 3520 is adjustable by pulling a length of inner body 2840 through housing 2850 by second end 2855.

Figure 29:
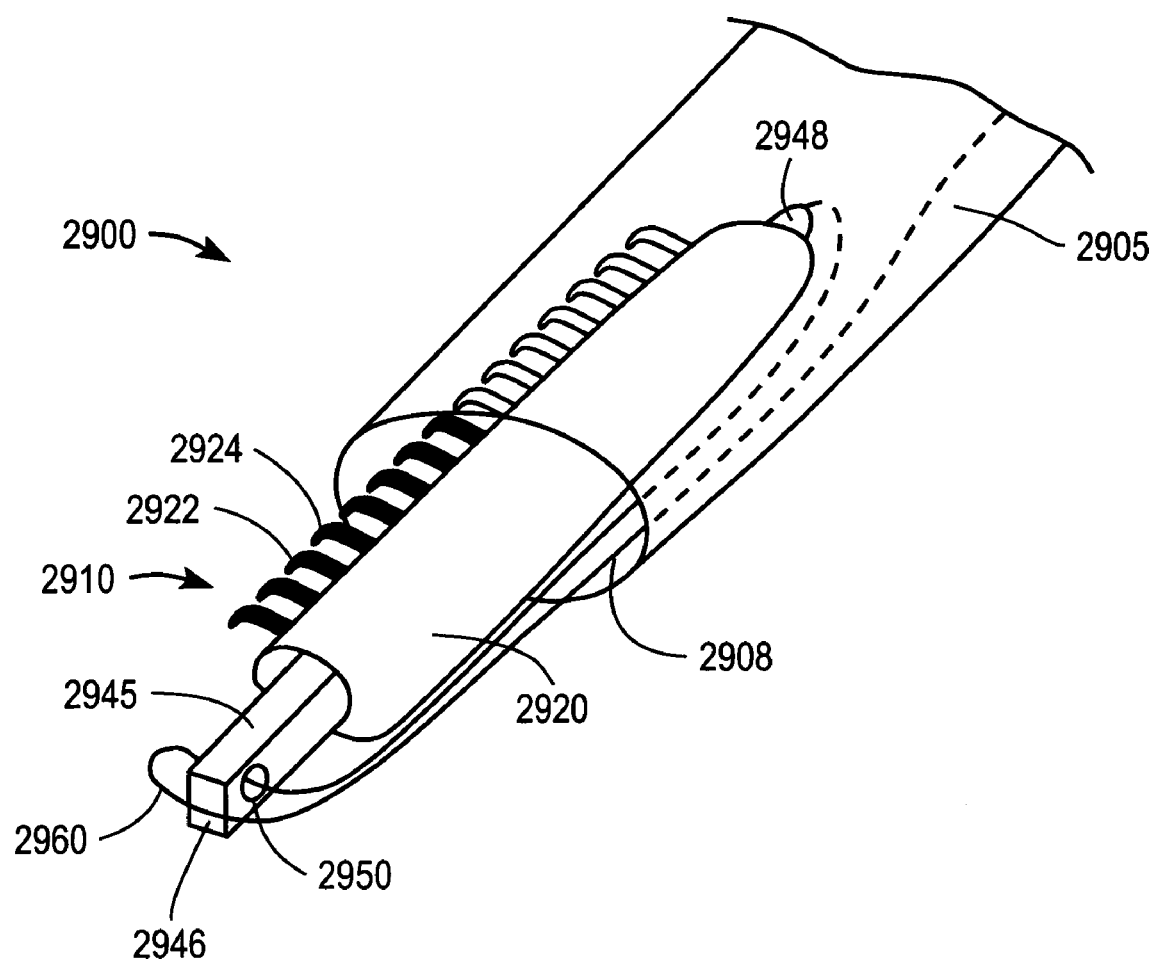
FIG. 29 illustrates a distal portion of a delivery system having a support annulus linearly disposed within a catheter.

In one embodiment, support annulus 2700 may be introduced percutaneously. To introduce support annulus 2700 to modify a mitral valve, support annulus 2700 may be introduced transeptally or through the aortic arch into the left ventricle and across the mitral valve. One advantage to the embodiment shown is that support annulus 2700 may be conformed to a desired shape and geometry of a valve annulus. Representatively, support annulus 2700 may be introduced through a catheter as a linear structure and modified to an annular shape about a heart valve. FIG. 29 shows a distal portion of a delivery system 2900 having a support annulus 2910 linearly disposed within a catheter 2905. In one embodiment, the support annulus 2910 is the support annulus 2700. FIG. 29 also shows support annulus 2910 housed in catheter 2905 as a linearly extending tube 2920 with hooks or barbs (e.g., hooks 2922, 2924) on one side of tube 2920. Catheter 2905 forms a lumen 2908 therethrough. Lumen 2908 has a diameter sufficient to encompass support annulus 2910 including tube 2920 and hooks 2922, 2924 (which may be hooks 2720 and 2722). Looped through opening 2950 is wire 2960. One end of wire 2960 extends from a first end 2946 to a second end 2948 near an end of catheter tube 2920, allowing an operator to manipulate inner body 2945, for example, to place second end 2948 within opening 2950 near first end 2946 to form an annular structure. Representatively, once second end 2948 is placed through opening 2950 and inner body 2945 is adjusted to be a desired diameter, wire 2960 may be detached from second end 3530 such as by applying a sufficient torque or pull force.

Figure 30:
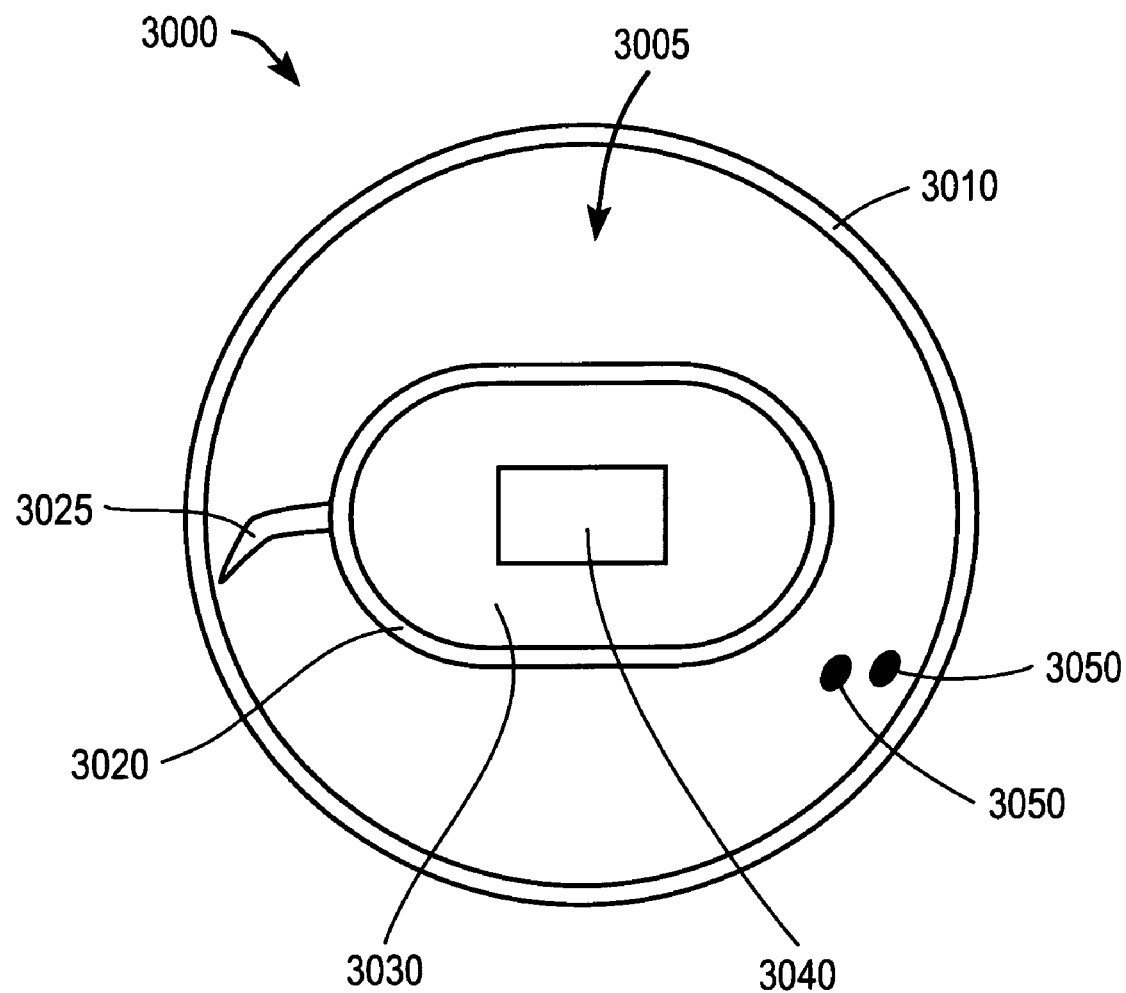
FIG. 30 illustrates a cross-sectional view of the distal portion of support annulus delivery system.

FIG. 30 illustrates a cross-sectional view 3000 of the distal portion of support annulus delivery system of catheter 2900. Catheter 3010 forms a lumen 3005 in which support annulus 3020 is disposed therein. Hook 3025 is shown extending from one side of support annulus 3020 which, in one embodiment, is the same as support annulus 2700. Support annulus 3020 also forms a lumen 3030 in which inner body 3040 is disposed. Wire 3050 is shown disposed within lumen 3005 with one portion extending from a first end to a second end of inner body 3040, and another portion extending all the way to a proximal portion (e.g., to the operator).

Figure 31:
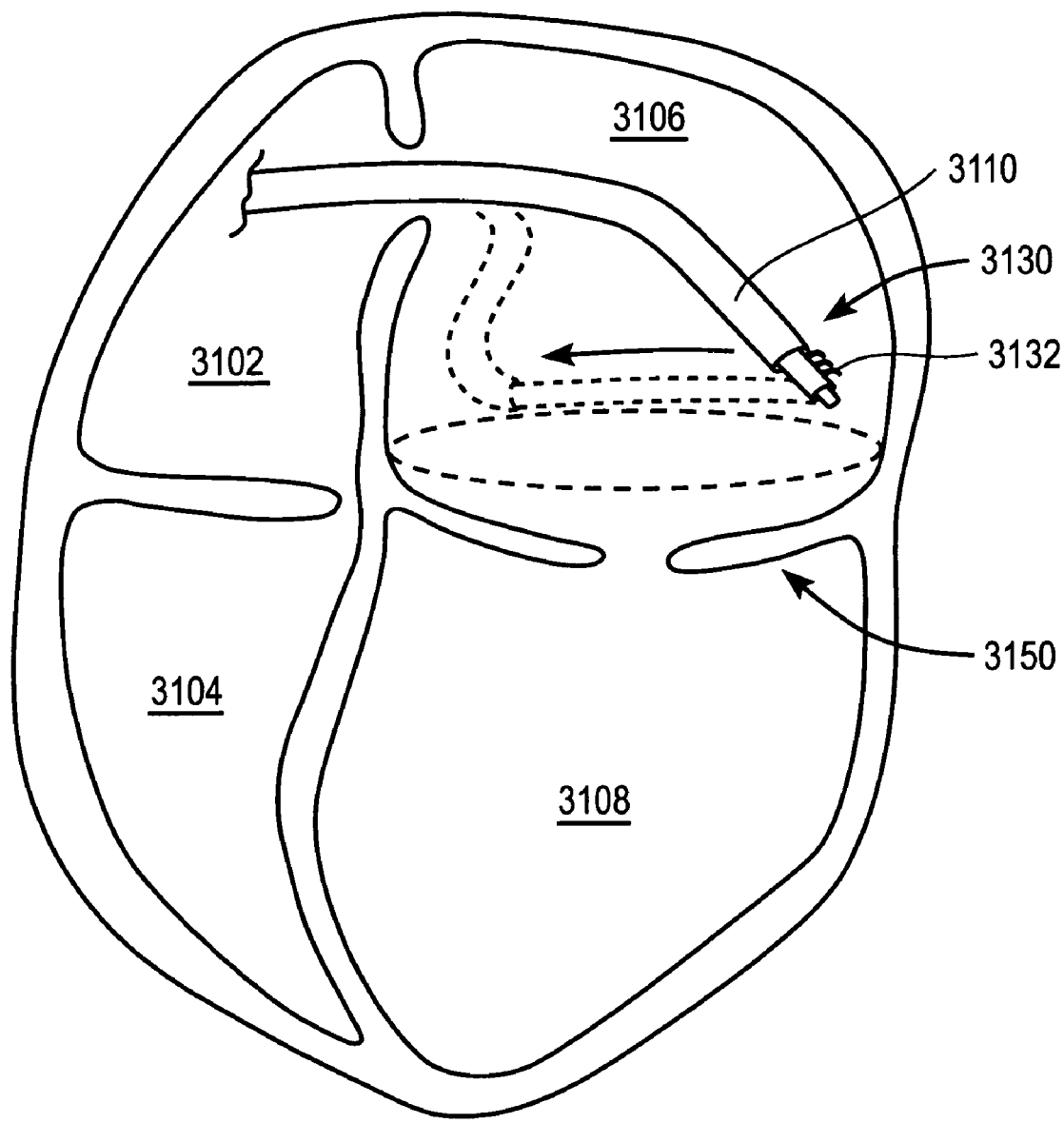
FIG. 31 illustrates a support annulus introduced into a left atrium transeptally through a catheter.

FIG. 31 illustrates support annulus 3130 introduced into a left atrium 3106 transeptally through catheter 3110. In one embodiment, the support annulus 3130 is the support annulus 2700. In one embodiment, support annulus 3130, once introduced, is advanced out of catheter 3110 incrementally to expose each hook (e.g., hook 3132) from support annulus 3130). FIG. 31 also illustrates the incremental advancement of support annulus 3130 from catheter 3110 and around mitral valve annulus 3150. As illustrated, the hooks (e.g., 3132) are positioned so that as support annulus 3130 is advanced from catheter 3110, the hooks are adjacent to the tissue around mitral valve annulus 3150. Imaging techniques may be utilized to properly orient support annulus 3130. For example, echo imaging, infrared illumination, x-ray, and magnetic resonance imaging methods may be utilized. Accordingly, the hooks are anchored incrementally into the tissue of mitral valve annulus 3150 as support annulus 3130 is advanced around mitral valve annulus 3150. In one embodiment, once a substantially circular shape has been formed by support annulus 3130 around valve annulus 3150, a first end may be tied to a second end of an inner body (disposed within support annulus 3130) as described above with respect to FIGS. 28A-B, and 29).

Figure 32A:
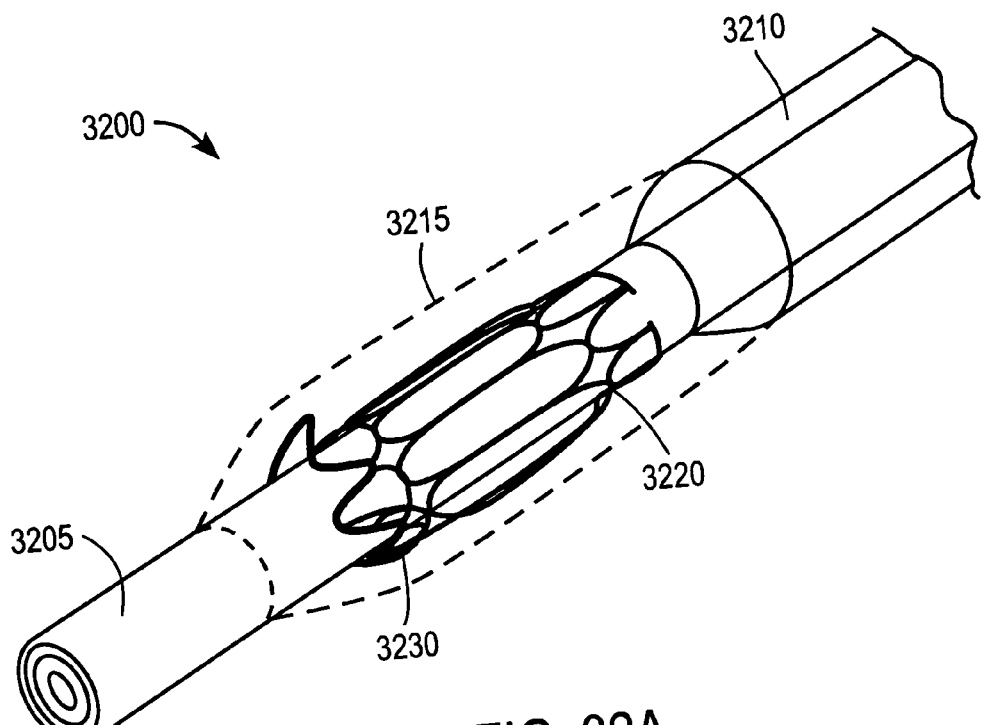
FIGS. 32A and 32B illustrate one embodiment of a support annulus having a crimped position and an expanded, deployment position.
Figure 32B:
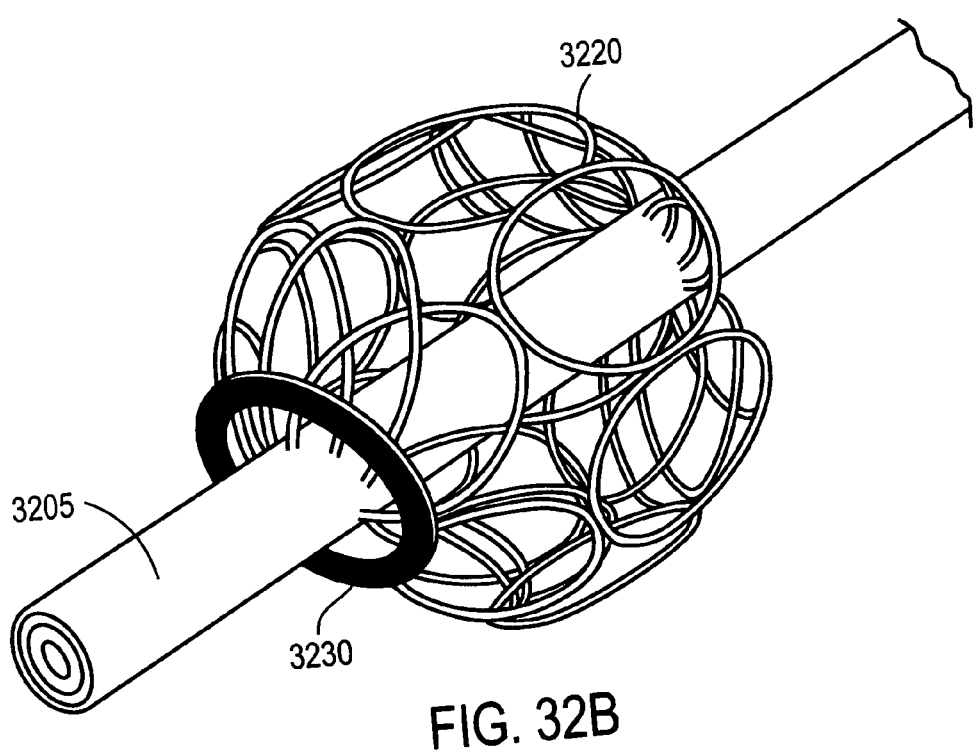

In another embodiment of a support annulus which is designed for percutaneous delivery, the support annulus may be made as a complete ring of metal, polymer of elastomer. The support annulus may be folded or crimped on a delivery system (e.g., catheter) to reduce its diameter for percutaneous advancement to the mitral valve. The delivery system or medical device may be, in one embodiment, a catheter containing an expandable cage and protective sheath disposed near the distal portion of the catheter. The support annulus may be loaded and crimped near the distal portion and coupled to the expandable cage, with the protective sheath drawn over the support annulus to prevent movement during delivery. FIGS. 32A and 32B illustrate one embodiment of a support annulus having a crimped position (FIG. 32A) and an expanded, deployment position (FIG. 32B). FIG. 32A shows medical device 3200 having a distal catheter portion 3210 with a guidewire 3205 disposed in a lumen therein. Distal portion of catheter 3210 extends to form a sheath 3215 which houses crimped support annulus 3230 that is coupled to expandable cage 3220. Support annulus 3230 and expandable cage 3220 is sized to fit easily within a space between guidewire 3205 and sheath 3215 as well as for advancement down catheter 3210. FIG. 32B shows support annulus 3230 and expandable cage 3220 in expanded positions with sheath 3215 removed. Support annulus 3230 has expanded to form a substantially complete circular ring. In one embodiment, support annulus may be evenly spaced around guidewire 3205. In another embodiment, the support annulus 3230 may form a partial ring having a substantially circular shape. In the expanded position, expandable cage 3220 may fit within the left atrium to position support annulus 3230 over the mitral valve annulus.

Figure 33A:
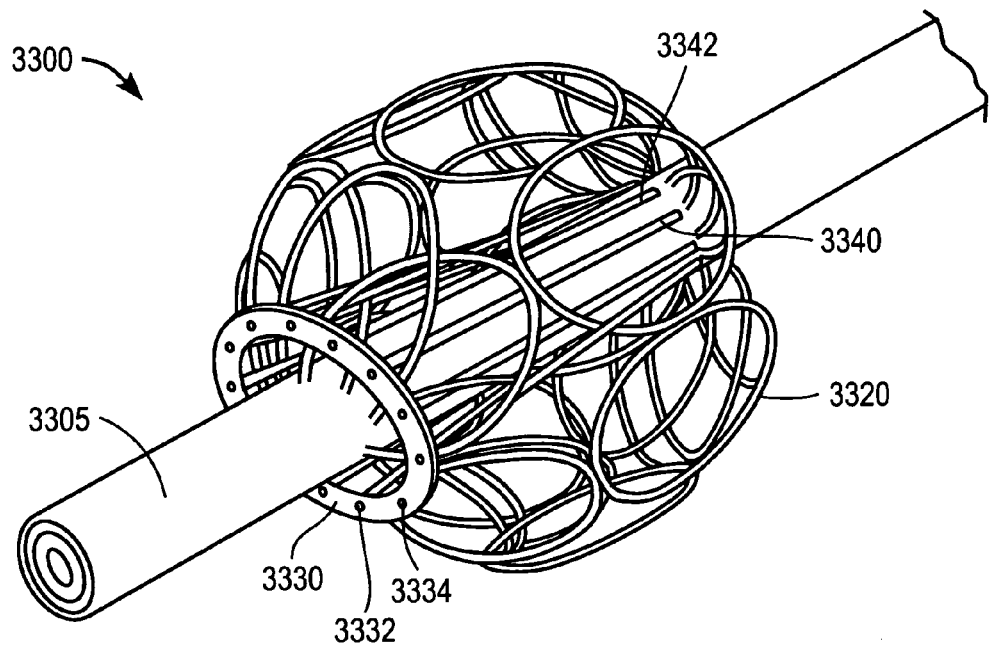
FIGS. 33A and 33B illustrate another embodiment of an expandable support annulus for deployment.
Figure 33B:
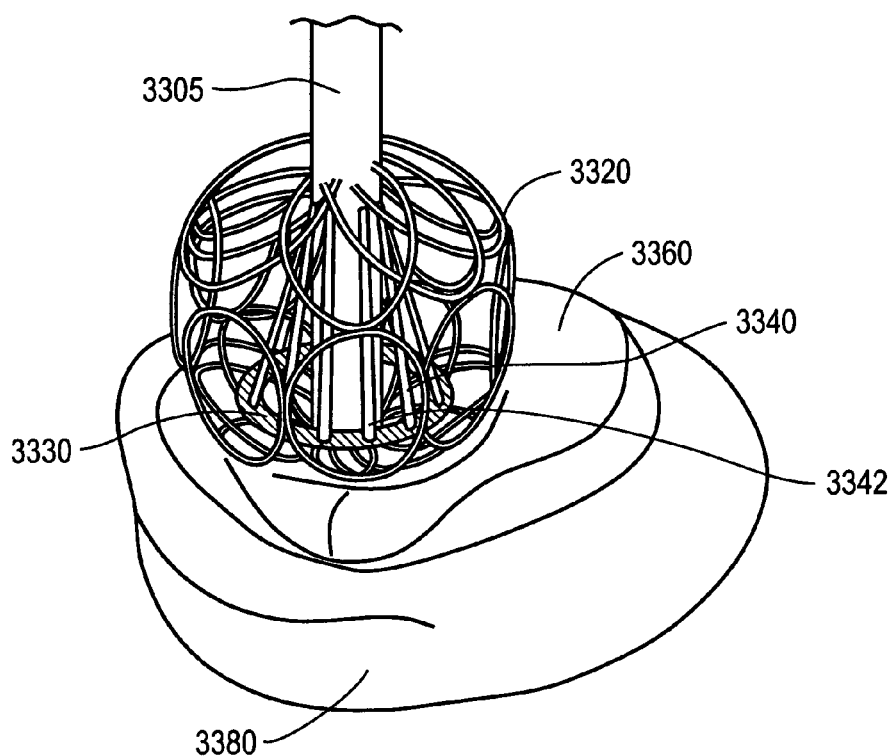

FIGS. 33A and 33B illustrate another embodiment of an expandable support annulus for deployment over a mitral valve annulus. The embodiments of FIGS. 33A and 33B may be the same as the embodiments shown in FIGS. 32A and 32B. FIG. 33A shows support annulus 3330, in an expanded state, as part of a medical device or catheter delivery system 3300 that includes a guidewire 3305 and an expandable cage 3320 coupled to support annulus 3330. Medical device 3300 may also have one or more shafts (e.g., 3340, 3342) extending along guidewire 3305 towards and in contact with support annulus 3330. In one embodiment, the distal end of shafts 3340, 3342 may be aligned with holes or openings 3332, 3334 on support annulus 3330. Shafts 3340, 3342 may release an attachment such as a helical tack or other comparable attachment through holes 3332, 3334 to secure support annulus 3330 to the valve annulus. FIG. 33B illustrates an alternative view of medical device 3300 positioned over mitral valve 3360 looking down from the left atrium of heart 3380. For clarity and to avoid confusion, heart 3380 is illustrated in a simplified form. Shafts extend along a surface guidewire 3305 and spread out towards a circumference of support annulus 3330, which has been expanded by expandable cage 3320. As described in greater detail below, the shafts (e.g., shafts 3340, 3342) may release attachments to secure support annulus 3330 to the annulus of mitral valve 3360.

Figure 34:
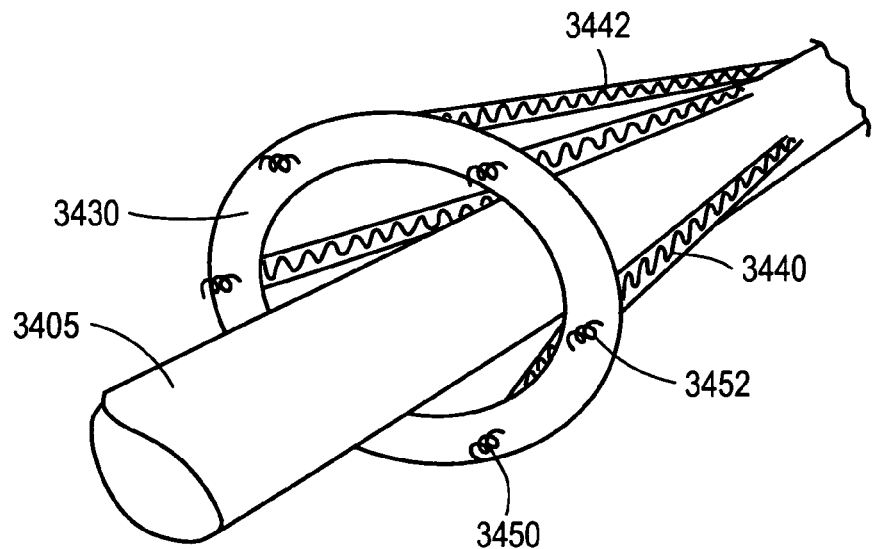
FIG. 34 illustrates a bottom view of expandable support annulus having one or more shafts.
Figure 35A:
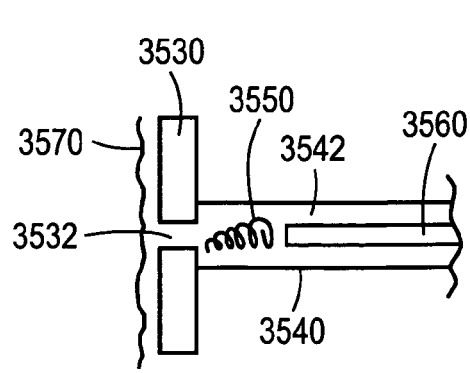
FIGS. 35A-35B illustrate one embodiment of an attachment mechanism for securing an expandable support annulus to a valve annulus.
Figure 35B:
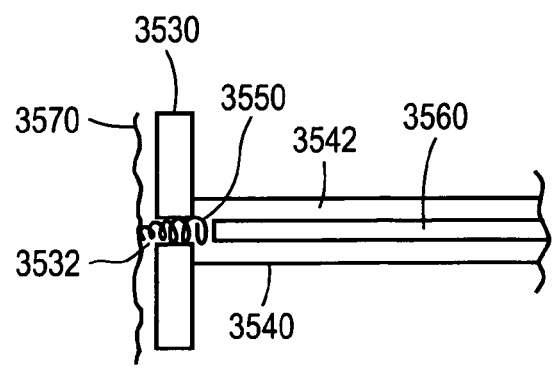

FIG. 34 illustrates a bottom view of expandable support annulus 3430 having one or more shafts (e.g., shafts 3440, 3442) attached around a circumference of support annulus 3430. The embodiments shown in FIG. 34 may be the same as the embodiments shown in FIGS. 33A and 33B (and also FIGS. 32A and 32B). Although an expandable cage is not shown (e.g., expandable cage 3320), it may be understood that support annulus 3430 has been expanded by an expandable cage coupled to support annulus 3430. On a bottom side of support annulus 3430, one or more helical attachments (e.g., attachments 3450, 3452) are illustrated extending through support annulus 3430. In one embodiment, the helical attachments penetrate a valve tissue to secure support annulus to the valve tissue. FIGS. 35A-B illustrate one embodiment of an attachment mechanism for securing an expandable support annulus to a valve annulus (e.g., a mitral valve annulus). FIG. 35A shows a cross-sectional side view of support annulus 3530 (such as annulus 3430) positioned near a valve tissue 3570. A shaft 3540 having a lumen formed therein has a helical attachment 3550 and a mandrel 3560 positioned behind helical attachment 3550. Prior to being released, helical attachment 3550 may be advanced to opening 3532 of support annulus 3530 with mandrel 3560. FIG. 35B shows helical attachment 3550 released through opening 3532 of support annulus 3530 by pushing mandrel 3560 forward. In one embodiment, mandrel 3560 may be controlled by a control mechanism or handle disposed near a proximal portion of the delivery system (e.g., control portion 2510 of FIG. 25).

Figure 36A:
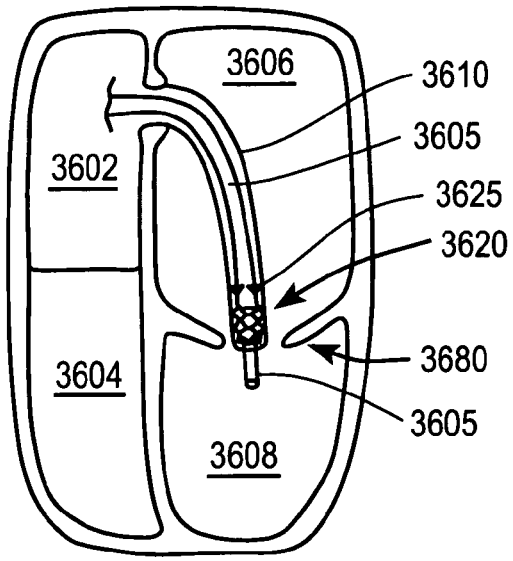
FIGS. 36A-36D illustrate one exemplary method of deploying an expandable support annulus to a mitral valve annulus percutaneously.
Figure 36B:
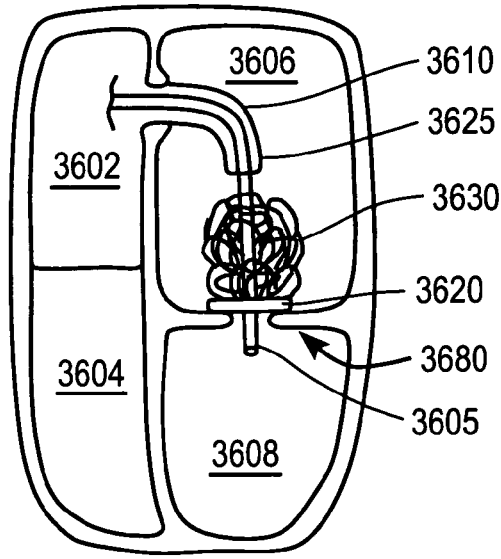

FIGS. 36A-D illustrate one exemplary method of deploying an expandable support annulus to a mitral valve annulus percutaneously. A simplified representation of a heart is shown with right atrium 3602, right ventricle 3604, left atrium 3606, and left ventricle 3608. As shown by FIG. 36A, the medical device including a delivery system for an expandable support annulus as described (e.g., device 3300) may enter the right atrium 3602 and pass through the atrial septum to the left atrium 3606 by standard valvuoplasty methods. Next, a guide wire 3605 may be passed across the mitral valve 3680. The delivery system including catheter 3610 having guidewire 3605 disposed therein also has a sheath portion 3625 near a distal portion of catheter 3610. Sheath portion 3625 crimps or compresses an expandable cage coupled to an expandable support annulus. Next, FIG. 36B shows sheath portion 3625 of catheter 3610 pulled back to allow cage 3630 to expand within left atrium 3606. The expansion of cage 3630 also expands support annulus 3620 that is coupled to cage 3630. The cage 3630 holds the support annulus 3620 against the mitral valve annulus 3680 during the attachment process, as well as allowing blood flow to continue as the heart beats normally. In one embodiment, the support annulus 3620 may be attached to the valve annulus 3680 by helical attachments described above (e.g., helical attachments 3450, 3452). The helical attachments may be provided by one or more shafts (not shown) that may be part of the delivery system. The shafts and helical attachments may be loaded with support annulus 3620 immediately after the support annulus 3620 is crimped onto the catheter 3610 or after the expansion of the support annulus 3620 and cage 3630. In an alternative embodiment, the attachment devices may also be delivered by a separate attachment device delivery system. For example, cage 3630 may over expand support annulus 3620 prior to attachment with valve 3680 and allow support annulus 3620 to compress around the valve annular circumference after it is attached to valve annulus 3680 (and detached from cage 3630).

Figure 36C:
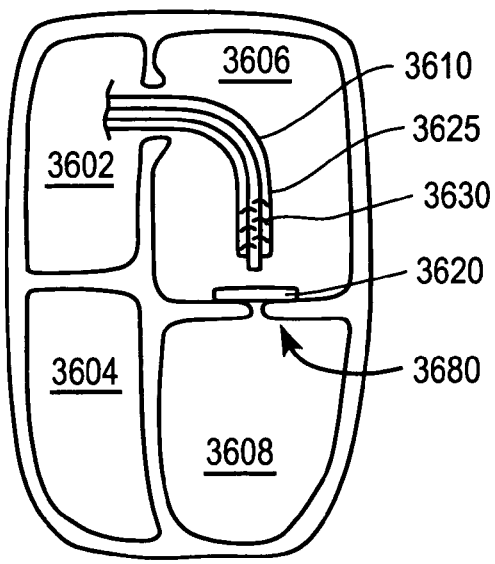
Figure 36D:
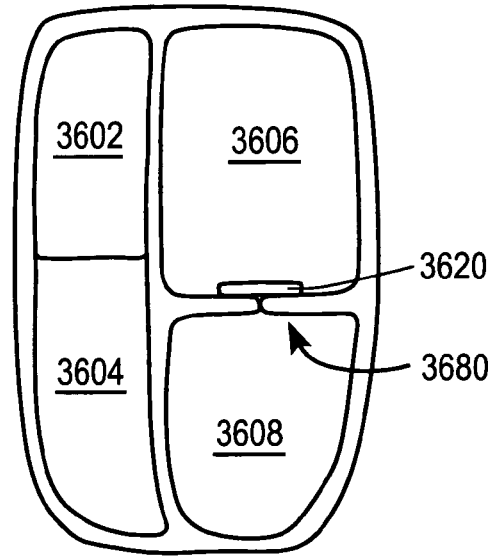

FIG. 36C shows sheath portion 3630 of catheter 3610 pulled back over cage 3625 to compress cage 3625 within sheath 3630. At this point, support annulus 3620 has been detached from cage 3625 and secured to valve annulus 3680. In one embodiment, cage 3625 needs to be crimped again so that it may be removed back across the septum from the left atrium to the right atrium and ultimately removed from the patient. FIG. 36D shows expandable support annulus 3620 secured to valve annulus 3680 with the catheter delivery system completely removed from the heart. As discussed above, this embodiment provides the advantage of percutaneously deploying a support annulus to a heart valve such as the mitral valve annulus without the complications and invasiveness of open heart surgery.

In one embodiment, a support annulus (e.g., support annulus 2200, 2300, 2700) or clips (e.g., clips 315, 335) percutaneously placed near a mitral valve region, or a device placed in the coronary sinus to treat the mitral valve, may be used to deliver or release a drug or therapeutic agent to treat mitral valve regurgitation. Various drugs are known in the art for treating mitral valve regurgitation. For example, administering nitroprusside (a vascular smooth muscle relaxant) may effectively diminish the amount of mitral regurgitation, thereby increasing forward output by the left ventricle and reducing pulmonary congestion. Inotropic agents such as dobutamine may also be administered to increase the force of contraction of the myocardium. In one embodiment, a percutaneous medical device to treat mitral valve regurgitation, such as a support annulus for resizing a mitral valve annulus, clips to ligate the mitral valve leaflets, or a device placed in the coronary sinus near the mitral valve region, may be coated with these exemplary drugs for delivery near the mitral valve region. The drugs may have timed-release features to be released slowly over a certain period of time. The drug eluting support annulus or other devices may also have the drug or agent dispersed on the surface of the support annulus or other devices, or co-dissolved in a matrix solution to be dispersed on the support annulus. Methods to coat the support annulus with a therapeutic drug include dip coating, spin coating, spray coating, or other coating methods commonly practiced in the art.

In some cases, patients with defective heart valves may have concomitant coronary artery disease (CAD). As such, it may be advantageous for a support annulus to deliver a drug to treat occlusions in the artery or other related CAD such as vulnerable plaque. The drug to treat CAD may be delivered alone or in combination with drugs to treat mitral valve regurgitation. Drugs to treat CAD include, but are not limited to, statins, lipid lowering agents, antioxidants, extracellular matrix synthesis promoters, inhibitors of plaque inflammation and extracellular degradation, estradiol drug classes and its derivatives.

In one embodiment, the drugs to treat CAD may be coated on a support annulus or other device using methods such as dip coating, spin coating, spray coating or other coating methods known in the art. The drug may alternatively be encapsulated in microparticles or nanoparticles and dispersed in a coating on the support annulus or other device. A diffusion limiting top-coat may optionally be applied to the above coatings. The active agents may optionally be loaded on a support annulus or other device together either by adding them together to the solution of the matrix polymer before coating, or by coating different layers, each containing a different agent or combination of agents. The drug eluting support annulus or other device may alternatively have an active agent or a combination of agents dispersed in a bioerodible annulus forming polymer.

In the foregoing specification, a medical device has been described with reference to specific exemplary embodiments thereof. It will, however, be evident that various modifications and changes may be made thereto without departing from the broader spirit and scope of the medical device as set forth in the appended claims. The specification and figures are, accordingly, to be regarded in an illustrative rather than a restrictive sense.

What is claimed is:

1. A medical device, comprising:
a first cardiac tissue fastener having a first lock at a proximal end of the first cardiac tissue fastener, the first cardiac tissue fastener configured to be compressed by a first sheath, wherein the first sheath includes at least one aligner on an inner lumen therein;
a second cardiac tissue fastener having a second lock at a proximal end of the second cardiac tissue fastener, the second cardiac tissue fastener configured to be compressed by a second sheath, wherein the second sheath includes at least one aligner on an inner lumen therein; and
a chord coupled to the first cardiac tissue fastener and the second cardiac tissue fastener, wherein a pulling of the chord slidably engages the first lock to the second lock in a telescoping manner to adjust a distance between the first cardiac tissue fastener and the second cardiac tissue fastener,
wherein when the first cardiac tissue fastener is extended from the first sheath, the first cardiac tissue fastener is released and the first sheath facilitates locking of the first cardiac tissue fastener in place by sliding over a portion of the first cardiac tissue fastener, and wherein when the second cardiac tissue fastener is extended from the second sheath, the second cardiac tissue fastener is released and the second sheath facilitates locking of the second cardiac tissue fastener in place by sliding over a portion of the second cardiac tissue fastener.

2. The medical device of claim 1, wherein the first cardiac tissue fastener and the second cardiac tissue fastener are adapted for percutaneous insertion to a cardiac region.

3. The medical device of claim 2, wherein the cardiac region comprises a mitral valve.

4. The medical device of claim 1 wherein the first and second cardiac tissue fasteners comprise a c-shaped clip.

5. The medical device of claim 1 wherein the first and second cardiac tissue fasteners are made of a shape memory metal.

6. The medical device of claim 2, further comprising a catheter to house the first and second cardiac tissue fasteners.

7. The medical device of claim 2, further comprising a control mechanism to control the first and second cardiac tissue fasteners.

8. The medical device of claim 2, wherein the first lock comprises a male-type lock and the second lock comprises a female-type lock.

9. The medical device of claim 8, wherein the first lock comprises an elongated member having a plurality of ridges on an outer surface.

10. The medical device of claim 8, wherein the second lock comprises an elongated member having an inner surface that is compatible with the outer surface of the first lock.

11. The medical device of claim 1, wherein the chord is trackable within the first lock and the second lock.

12. A medical device, comprising:
a first fastener assembly, comprising:
a first fastener;
a first lock connected to a proximal end of the first fastener; and
a first housing that contains the first fastener, the first fastener configured to be compressed by the first housing, wherein the first housing includes at least one aligner in a first lumen therein;
a second fastener assembly, comprising:
a second fastener;
a second lock connected to a proximal end of the second fastener; and
a second housing that contains the second fastener, the second fastener configured to be compressed by the second housing, wherein the second housing includes at least one aligner in a second lumen therein; and
a chord coupled to the first fastener and the second fastener, the chord trackable through the first lock and the second lock, wherein a pulling of the chord enables a distance between the first fastener and the second fastener to be adjusted percutaneously by slidable engagement of the first lock with the second lock in a telescoping manner,
wherein when the first fastener is extended from the first housing, the first fastener is released and the first housing facilitates locking of the first fastener in place by sliding over the proximal end of the first fastener, and wherein when the second fastener is extended from the second housing, the second fastener is released and the second housing facilitates locking of the second fastener in place by sliding over the proximal end of the second fastener.

13. The medical device of claim 12, wherein the first lumen of the first housing is adapted to receive a first mandrel to release the first fastener.

14. The medical device of claim 13, wherein the second lumen of the second housing is adapted to receive a second mandrel to release the second fastener.

15. The medical device of claim 12, wherein the first lock comprises a male-type lock and the second lock comprises a female-type lock to engage compatibly.

16. The medical device of claim 15, wherein the first and second fasteners are c-shaped.

17. The medical device of claim 16, wherein the first and second fasteners are adapted to grasp a mitral valve leaflet.

18. The medical device of claim 16, wherein the first and second fasteners are adapted to grasp a cardiac tissue.

19. The apparatus of claim 1, further comprising at least one aligner within a first lumen of the first sheath and at least one aligner within a second lumen of the second sheath, wherein the aligners are configured for engaging and orienting the first and second cardiac tissue fasteners.

* * * * *